US009476063B2

(12) United States Patent
Stayton et al.

(10) Patent No.: US 9,476,063 B2
(45) **Date of Patent: *Oct. 25, 2016**

(54) DIBLOCK COPOLYMERS AND POLYNUCLEOTIDE COMPLEXES THEREOF FOR DELIVERY INTO CELLS

(75) Inventors: Patrick S. Stayton, Seattle, WA (US); Allan S. Hoffman, Seattle, WA (US); Anthony J. Convertine, Seattle, WA (US); Danielle Benoit, Rochester, NY (US); Craig L. Duvall, Nashville, TN (US); Paul H. Johnson, Snohomish, WA (US); Anna S. Gall, Woodinville, WA (US)

(73) Assignees: University of Washington, Seattle, WA (US); PhaseRx, Inc., Seattle, WA (US)

( * ) Notice: Subject to any disclaimer, the term of this patent is extended or adjusted under 35 U.S.C. 154(b) by 153 days.

This patent is subject to a terminal disclaimer.

(21) Appl. No.: 12/992,517

(22) PCT Filed: May 13, 2009

(86) PCT No.: PCT/US2009/043847

§ 371 (c)(1), (2), (4) Date: Feb. 9, 2011

(87) PCT Pub. No.: WO2009/140427

PCT Pub. Date: Nov. 19, 2009

(65) Prior Publication Data

US 2011/0143434 A1 Jun. 16, 2011

Related U.S. Application Data

(60) Provisional application No. 61/120,769, filed on Dec. 8, 2008, provisional application No. 61/091,294, filed on Aug. 22, 2008, provisional application No. 61/052,914, filed on May 13, 2008, provisional application No. 61/140,774, filed on Dec. 24, 2008, provisional application No. 61/171,377, filed on Apr. 21, 2009, provisional application No. 61/112,048, filed on Nov. 6, 2008, provisional application No. 61/140,779, filed on Dec. 24, 2008, provisional application No. 61/112,054, filed on Nov. 6, 2008, provisional application No. 61/052,908, filed on May 13, 2008.

(51) Int. Cl.

| | |
|---|---|
| ***C08F 293/00*** | (2006.01) |
| ***C12N 5/071*** | (2010.01) |
| ***C12N 15/87*** | (2006.01) |
| ***C12N 15/11*** | (2006.01) |

(52) U.S. Cl.

CPC ............. *C12N 15/87* (2013.01); *C08F 293/00* (2013.01); *C08F 293/005* (2013.01); *C12N 15/111* (2013.01); *C07K 2319/10* (2013.01); *C12N 2310/14* (2013.01); *C12N 2310/315* (2013.01); *C12N 2320/32* (2013.01)

(58) Field of Classification Search

CPC .. A61K 31/7084; A61K 38/00; A61K 38/02; A61K 47/32; A61K 47/48; A61K 47/48007; A61K 47/48092; A61K 47/48238; C08F 293/00; C08F 293/005

USPC ........... 514/1.1, 44 R, 44 A, 772.1; 525/280, 525/294, 54.2

See application file for complete search history.

(56) References Cited

U.S. PATENT DOCUMENTS

| | | | | |
|---|---|---|---|---|
| 4,699,784 | A | 10/1987 | Shih | |
| 5,057,313 | A | 10/1991 | Shih | |
| 6,306,994 | B1 * | 10/2001 | Donald et al. | 526/317.1 |
| 6,359,054 | B1 | 3/2002 | Lemieux | |
| 6,383,811 | B2 | 5/2002 | Wolff | |
| 6,410,057 | B1 | 6/2002 | Kweon-Choi | |
| 6,780,428 | B2 | 8/2004 | Ranger | |
| 6,835,393 | B2 | 12/2004 | Hoffman | |
| 6,919,091 | B2 | 7/2005 | Trubetskoy | |
| 6,939,564 | B2 | 9/2005 | Ranger | |
| 7,033,607 | B2 | 4/2006 | Trubetskoy | |
| 7,094,810 | B2 | 8/2006 | Sant | |
| 7,098,032 | B2 | 8/2006 | Trubetskoy | |

(Continued)

FOREIGN PATENT DOCUMENTS

| | | |
|---|---|---|
| EP | 0 321 233 A1 | 6/1989 |
| EP | 2 180 004 A1 | 4/2010 |

(Continued)

OTHER PUBLICATIONS

Lowe et al. (Chemical Communications, Issue 11, pp. 1035-1036, Published in 1997).*

Gotzamanis et al. (Macromolecular Rapid Communications, 27, published 2006, pp. 1757-1763).*

Benoit, D.S.W., et al., "Resensitizing Multidrug Resistant Cells to Doxorubicin Through plk1 Knockdown Using a Novel pH-Responsive Micelle siRNA Delivery System," Abstracts of Society for Biomaterials Meeting, Apr. 22, 2009, 1 page.

(Continued)

*Primary Examiner* — Alma Pipic

(74) *Attorney, Agent, or Firm* — Christensen O'Connor Johnson Kindness

(57) ABSTRACT

Described herein are copolymers, and methods of making and utilizing such copolymers. Such copolymers have at least two blocks: a first block that has at least one unit that is hydrophilic at physiologic pH, and a second block that has hydrophobic groups. This second block further has at least one unit with a group that is anionic at about physiologic pH. The described copolymers are disruptive of a cellular membrane, including an extracellular membrane, an intracellular membrane, a vesicle, an organelle, an endosome, a liposome, or a red blood cell. Preferably, in certain instances, the copolymer disrupts the membrane and enters the intracellular environment. In specific examples, the copolymer is endosomolytic.

32 Claims, 21 Drawing Sheets

(56) References Cited

U.S. PATENT DOCUMENTS

| | | | | |
|---|---|---|---|---|
| 7,217,776 | B1 | 5/2007 | Mallapragada | |
| 7,374,778 | B2 | 5/2008 | Hoffman | |
| 7,510,731 | B2 | 3/2009 | Ranger | |
| 7,524,680 | B2 | 4/2009 | Wolff | |
| 7,718,193 | B2 | 5/2010 | Stayton | |
| 7,737,108 | B1 | 6/2010 | Hoffman | |
| 8,367,113 | B2 | 2/2013 | Gu | |
| 9,220,791 | B2 * | 12/2015 | Stayton | A61K 47/48176 |
| 2001/0007666 | A1 | 7/2001 | Hoffman | |
| 2003/0134420 | A1 | 7/2003 | Lollo | |
| 2003/0191081 | A1 | 10/2003 | Lemieux | |
| 2003/0211167 | A1 | 11/2003 | Gustavsson | |
| 2004/0054127 | A1 | 3/2004 | Jin | |
| 2004/0072784 | A1 | 4/2004 | Sant | |
| 2004/0151775 | A1 | 8/2004 | Rozema | |
| 2004/0162235 | A1 | 8/2004 | Trubetskoy | |
| 2005/0070721 | A1 | 3/2005 | Bae | |
| 2005/0220880 | A1 | 10/2005 | Lewis | |
| 2005/0260276 | A1 | 11/2005 | Yang | |
| 2006/0030685 | A1 | 2/2006 | Boupat | |
| 2006/0134221 | A1 | 6/2006 | Geall | |
| 2006/0165810 | A1 | 7/2006 | Discher | |
| 2006/0171980 | A1 | 8/2006 | Helmus | |
| 2006/0217285 | A1 | 9/2006 | Destarac | |
| 2006/0235161 | A1 | 10/2006 | Heller | |
| 2007/0003609 | A1 | 1/2007 | Collin-Djangone | |
| 2007/0010632 | A1 | 1/2007 | Kaplan | |
| 2007/0037891 | A1 | 2/2007 | Esfand | |
| 2007/0059271 | A1 | 3/2007 | Kataoka | |
| 2007/0110709 | A1 | 5/2007 | Ranger | |
| 2007/0134188 | A1 | 6/2007 | Collin-Djangone | |
| 2007/0224241 | A1 | 9/2007 | Stayton | |
| 2008/0069902 | A1 | 3/2008 | Zhao | |
| 2008/0081075 | A1 | 4/2008 | Hsiue | |
| 2008/0171067 | A1 | 7/2008 | Govindan | |
| 2008/0243049 | A1 | 10/2008 | Hardy | |
| 2009/0036625 | A1 | 2/2009 | Chang | |
| 2010/0150952 | A1 | 6/2010 | Stayton | |
| 2011/0123636 | A1 | 5/2011 | Stayton | |
| 2011/0143435 | A1 | 6/2011 | Stayton | |
| 2011/0281354 | A1 | 11/2011 | Stayton | |
| 2011/0281934 | A1 | 11/2011 | Johnson | |
| 2011/0286957 | A1 | 11/2011 | Prieve | |
| 2012/0021514 | A1 | 1/2012 | Johnson | |

FOREIGN PATENT DOCUMENTS

| | | | |
|---|---|---|---|
| FR | 2 767 829 | A1 | 3/1999 |
| WO | 99/29303 | A1 | 6/1999 |
| WO | 01/87227 | A2 | 11/2001 |
| WO | 03/087188 | A1 | 10/2003 |
| WO | 2005/108614 | A2 | 11/2005 |
| WO | 2006016166 | A1 | 2/2006 |
| WO | 2007/008300 | A2 | 1/2007 |
| WO | 2007/109584 | A1 | 9/2007 |
| WO | 2008/004978 | A1 | 1/2008 |
| WO | 2008/022309 | A2 | 2/2008 |
| WO | 2008/071009 | A1 | 6/2008 |
| WO | 2008/085556 | A2 | 7/2008 |
| WO | 2008/148174 | A1 | 12/2008 |
| WO | 2008/153940 | A1 | 12/2008 |
| WO | 2009/009025 | A1 | 1/2009 |
| WO | 2009/021728 | A2 | 2/2009 |
| WO | 2009/140421 | A2 | 11/2009 |
| WO | 2009/140423 | A2 | 11/2009 |
| WO | 2009/140427 | A2 | 11/2009 |
| WO | 2009/140429 | A2 | 11/2009 |
| WO | 2009/140432 | A2 | 11/2009 |
| WO | 2010/021770 | A1 | 2/2010 |
| WO | 2010/053596 | A1 | 5/2010 |
| WO | 2010/053597 | A2 | 5/2010 |
| WO | 2010/054266 | A2 | 5/2010 |
| WO | 2010/077678 | A2 | 7/2010 |

OTHER PUBLICATIONS

Bulmus, V., et al., "A New pH-Responsive and Glutathione-Reactive, Endosomal Membrane-Disruptive Polymeric Carrier for Intracellular Delivery of Biomolecular Drugs," Journal of Controlled Release 93(2):105-120, Dec. 2003.

Convertine, A.J., et al., "Development of a Novel Endosomolytic Diblock Copolymer for siRNA Delivery," Journal of Controlled Release 133(3):221-229, Feb. 2009.

Dufresne, M.-H., et al., "Characterization of Polyion Complex Micelles Designed to Address the Challenges of Oligonucleotide Delivery," Pharmaceutical Research 25(9):2083-2093, Sep. 2008.

Duvall, C.L., et al., "Polymer Enhanced Intracellular Delivery of a Pro-Apoptotic Peptide for Cancer Therapy," Abstracts of Society for Biomaterials Meeting, Apr. 22, 2009, 1 page.

El-Sayed, M.E.H., et al., "Smart Polymeric Carriers for Enhanced Intracellular Delivery of Therapeutic Macromolecules," Expert Opinion on Biological Therapy 5(1):23-32, Jan. 2005.

El-Sayed, M.E.H., et al., "Rational Design of Composition and Activity Correlations for pH-Sensitive and Glutathione-Reactive Polymer Therapeutics," Journal of Controlled Release 101(1-3):47-58, Jan. 2005.

Funhoff, A.M., et al., "Endosomal Escape of Polymeric Gene Delivery Complexes Is Not Always Enhanced by Polymers Buffering at Low pH," Biomacromolecules 5(1):32-39, Jan.-Feb. 2004.

Gaucher, G., et al., "Block Copolymer Micelles: Preparation, Characterization and Application in Drug Delivery," Journal of Controlled Release 109(1-3):169-188, Dec. 2005.

Henry, S.M., et al., "pH-Responsive Poly(styrene-alt-maleic anhydride) Alkylamide Copolymers for Intracellular Drug Delivery," Biomacromolecules 7(8):2407-2414, Aug. 2006.

Heredia, K.L., et al., "Reversible siRNA-Polymer Conjugates by RAFT Polymerization," Chemical Communications 28(28):3245-3247, Jul. 2008.

Inoue, T., et al., "An AB Block Copolymer of Oligo(methyl methacrylate) and Poly(acrylic acid) for Micellar Delivery of Hydrophobic Drugs," Journal of Controlled Release 51(2-3):221-229, Feb. 1998.

Jensen, K.D., et al., "Antisense Oligonucleotides Delivered to the Lysosome Escape and Actively Inhibit the Hepatitis B Virus," Bioconjucate Chemistry 13(5):975-984, Sep.-Oct. 2002.

Kataoka, K., et al., "Smart Polymeric Micelles as Nanocarriers for Oligonucleotides and siRNA Delivery," Nucleic Acids Symposium Series 49(1):17-18, Sep. 2005.

Kulkarni, S., et al, "Controlling the Aggregation of Conjugates of Streptavidin With Smart Block Copolymers Prepared via the RAFT Copolymerization Technique," Biomacromolecules 7(10):2736-2741, Oct. 2006.

Murthy, N., et al., "Bioinspired pH-Responsive Polymers for the Intracellular Delivery of Biomolecular Drugs," Bioconjugate Chemistry 14(2):412-419, Mar.-Apr. 2003.

Murthy, N., et al., "The Design and Synthesis of Polymers for Eukaryotic Membrane Disruption," Journal of Controlled Release 61(1-2):137-143, Aug. 1999.

Peppas, N.A., "Is There a Future in Glucose-Sensitive, Responsive Insulin Delivery Systems?" Drug Delivery Science and Technology 14(4):247-256, Sep. 2004.

Read, M.L., et al., "Physicochemical and Biological Characterisation of an Antisense Oligonucleotide Targeted Against the bcl-2 mRNA Complexed With Cationic-Hydrophilic Copolymers," European Journal of Pharmaceutical Sciences 10(3):169-177, May 2000.

Segura, T., and J.A. Hubbell, "Synthesis and In Vitro Characterization of an ABC Triblock Copolymer for siRNA Delivery," Bioconjugate Chemistry 18(3):736-745, May 2007.

Stayton, P.S., and A.S. Hoffman, "'Smart' pH-Responsive Carriers for Intracellular Delivery of Biomolecular Drugs," in V. Torchilin (ed.), "Fundamental Biomedical Technologies: Multifunctional Pharmaceutical Nanocarriers," Springer Science+Business Media, LLC, New York, May 2008, vol. 4, pp. 143-159.

Stayton, P.S., et al., "Intelligent Biohybrid Materials for Therapeutic and Imaging Agent Delivery," Proceedings of the IEEE 93(4):726-736, Apr. 2005.

(56) References Cited

OTHER PUBLICATIONS

Torchilin, V.P., "Micellar Nanocarriers: Pharmaceutical Perspectives," Pharmaceutical Research 24(1):1-16, Jan. 2007.
Wang, L., et al., "Delivery of Antisense Oligonucleotides Using HPMA Polymer: Synthesis of a Thiol Polymer and Its Conjugation to Water-Soluble Molecules," Bioconjugate Chemistry 9(6):749-757, Nov.-Dec. 1998.
Yamamoto, S.-I., et al., "Temperature- and pH-Responsive Dense Copolymer Brushes Prepared by ATRP," Macromolecules 41(19):7013-7020, Oct. 2008.
Yessine, M.-A., et al., "Proton-Actuated Membrane-Destabilizing Polyion Complex Micelles," Bioconjugate Chemistry 18(3):1010-1014, May-Jun. 2007.
International Search Report and Written Opinion mailed Jan. 13, 2010, in corresponding International Application No. PCT/US2009/043847, filed May 13, 2009, 15 pages.
Fishbein, I., et al., "Local Delivery of Gene Vectors From Bare-Metal Stents by Use of a Biodegradable Synthetic Complex Inihibits In-Stent Restenosis in Rat Carotid Arteries," Circulation 117(16):2096-2103, Apr. 2008.
Invitiation to Pay Additional Fees and Partial International Search Report mailed Apr. 26, 2011, issued in corresponding International Application No. PCT/US2010/056993, filed Nov. 17, 2010, 6 pages.
Varghese, O.P., et al., "In Situ Cross-Linkable High Molecular Weight Hyaluronan-Bisphosphonate Conjugate for Localized Delivery and Cell-Specific Targeting: A Hydrogel Linked Prodrug Approach," Journal of the American Chemical Society 131(25):8781-8783, Jul. 2009.
Intellectual Property Office of Singapore Search and Examination Report mailed Jun. 6, 2012, issued in corresponding Singapore Application No. 201008331-9, filed May 13, 2009, 10 pages.
Cho, Y.W., et al., "Polycation Gene Delivery Systems: Escape From Endosomes to Cytosol," Journal of Pharmacy and Pharmacology 55(6):721-734, Jun. 2003.
International Search Report and Written Opinion mailed Mar. 7, 2011, issued in corresponding International Application No. PCT/US2010/056565, filed Nov. 12, 2010, 12 pages.
Glinel, K., et al., "Responsive Polyelectrolyte Multilayers," Colloids and Surfaces A: Physicochemical and Engineering Aspects 303(1-2):3-13, Aug. 2007.
Extended European Search Report mailed Sep. 27, 2011, issued in corresponding European Application No. 09 74 7510, filed May 13, 2009, 3 pages.
Jeong, J.H., et al., "siRNA Conjugate Delivery Systems," Bioconjugate Chemistry 20(1):5-14, Jan. 2009.
Meyer, M., et al., "Synthesis and Biological Evaluation of a Bioresponsive and Endosomolytic siRNA-Polymer Conjugate," Molecular Pharmaceutics 6(3):752-762, May-Jun. 2009.
Oishi M., et al., "Lactosylated Poly(ethylene glycol)-siRNA Conjugate Through Acid-Labile β-Thiopropionate Linkage to Construct pH-Sensitive Polyion Complex Micelles Achieving Enhanced Gene Silencing in Hepatoma Cells," Journal of the American Chemical Society 127(6):1624-1625, Feb. 2005.
Glinel, Karine, et al., "Responsive Polyelectrolyte Multilayers," Colloids and Surfaces A: Physicochemical and Engineering Aspects 303(1-2):3-13, Aug. 2007.
Extended European Search Report mailed Jun. 28, 2013, issued in corresponding European Application No. 13156237.3, filed May 13, 2009, 3 pages.
Satturwar, P., et al., "pH-Responsive Polymeric Micelles of Poly(ethylene glycol)-b-poly(alkyl(meth)acrylate-co-methacrylic acid): Influence of the Copolymer Composition on Self-Assembling Properties and Release of Candesartan Cilexetil," European Journal of Pharmaceutics and Biopharmaceutics 65(3):379-387, Mar. 2007.
Extended European Search Report mailed Feb. 5, 2014, issued in corresponding European Application No. 09 825 146.5, filed May 13, 2009, 9 pages.
Cheung, C.Y., et al., "A pH-Sensitive Polymer That Enhances Cationic Lipid-Mediated Gene Transfer," Bioconjugate Chemistry 12(6):906-910, Oct. 2001.
Hood, J.D., et al., "Tumor Regression by Targeted Gene Delivery to the Neovasculature," Science, New Series 296 (5577):2404-2407, Jun. 2002.
Jeong, Y.-I., et al., "Cellular Recognition of Paclitaxel-Loaded Polymeric Nanoparticles Composed of Poly(y-benzyl L-glutamate) and Poly(ethylene glycol) Diblock Copolymer Endcapped With Galactose Moiety," International Journal of Pharmaceutics 296(2005):151-161, Apr. 2005.
Joralemon, M.J., et al., "Synthesis, Characterization, and Bioavailability of Mannosylated Shell Cross-Linked Nanoparticles," Biomacromolecules 5(3):903-913, May-Jun. 2004.
Kabanov, A.V., et al., "Pluronic Micelles as a Tool for Low-Molecular Compound Vector Delivery Into a Cell: Effect of *Staphylococcus-aureus* Enterotoxin B on Cell Loading With Micelle Incorporated Fluorescent Dye," Biochemistry International 26(6):1035-1042, May 1992.
Kyriakides, T.R., et al., "pH-Sensitive Polymers That Enhance Intracellular Drug Delivery In Vivo," Journal of Controlled Release 78(1-3):295-303, Jan. 2002.
Le Garrec, D., et al., "Micelles in Anticancer Drug Delivery," American Journal of Drug Delivery 2(1):15-42, Mar. 2004.
Lee, E.S., et al., "Super pH-Sensitive Multifunctional Polymeric Micelle," Nano Letters 5(2):325-329, Feb. 2005.
Nagasaki, Y. et al., "Sugar-Installed Block Copolymer Micelles: Their Preparation and Specific Interaction With Lectin Molecules," Biomacromolecules 2(4):1067-1070, Winter 2001.
Raso, V., "Intracellular Targeting Using Bispecific Antibodies," Methods in Molecular Medicine 25:37-49, Jan. 2000.
Sawant, R.M., et al., "'SMART'" Drug Delivery Systems: Double-Targeted pH-Responsive Pharmaceutical Nanocarriers, Bioconjugate Chemistry 17:943-949, Jun. 2006.
Turk, M.J., et al., "Characterization of a Novel pH-Sensitive Peptide That Enhances Drug Release From Folate-Targeted Liposomes at Endosomal pHs," Biochimica et Biophysica Acta 1559(1):56-68, Feb. 2002.
Wakebayashi, D., et al., "Lactose-Conjugated Polyion Complex Micelles Incorporating Plasmid DNA as a Targetable Gene Vector System: Their Preparation and Gene Transfecting Efficiency Against Cultured HepG2 Cells," Journal of Controlled Release 95(3):653-664, Mar. 2004.
Yasugi, K., et al., "Sugar-Installed Polymer Micelles: Synthesis and Micellization of Poly(ethylene glycol)-Poly(D,L-lactide) Block Copolymers Having Sugar Groups at the PEG Chain End," Macromolecules 32:8024-8032, Nov. 1999.
Yoo, H.S., and T.G. Park, "Folate Receptor Targeted Biodegradable Polymeric Doxorubicin Micelles," Journal of Controlled Release 96(2):273-283, Apr. 2004.
Stayton, P.S., "Bispecific Intracellular Delivery Vehicles," U.S. Appl. No. 14/173,730, filed Feb. 5, 2014.
Agarwal, A., et al., "Dual-Role Self-Assembling Nanoplexes for Efficient Gene Transfection and Sustained Gene Delivery," Biomaterials 29(5):607-617, Feb. 2008.
Alvarez-Lorenzo, C., et al., "Biophysical Characterization of Complexation of DNA with Block Copolymers of Poly(2-dimethylaminoethyl) Methacrylate, Poly(ethylene oxide), and Poly-(propylene oxide)," Langmuir 21(11):5142-5148, May 24, 2005.
Boeckle, S., et al., "Purification of Polyethylenimine Polyplexes Highlights the Role of Free Polycations in Gene Transfer," The Journal of Gene Medicine 6(10):1102-1111, Oct. 2004.
Cheng, Z., et al., "Brush-Type Amphiphilic Diblock Copolymers From 'Living'/Controlled Radical Polymerizations and Their Aggregation Behavior," Langmuir 21(16):7180-7185, Jul. 2005.
Eliyahu, H., et al., "Novel Dextran-Spermine Conjugates as Transfecting Agents: Comparing Water-Soluble and Micellar Polymers," Gene Therapy 12(6):494-503, Mar. 2005.
Final Office Action mailed Nov. 4, 2014, from U.S. Appl. No. 13/127,959, filed Jul. 27, 2011, 24 pages.
Final Office Action mailed Mar. 21, 2014, from U.S. Appl. No. 13/127,962, filed Jul. 26, 2011, 11 pages.
Finne-Wistrand, A., and A.-C. Albertson, "The Use of Polymer Design in Resorbable Colloids," Annual Review of Materials Research 36:369-395, Aug. 2006.

(56) References Cited

OTHER PUBLICATIONS

Gary, D.J., et al., "Polymer-Based siRNA Delivery: Perspectives on the Fundamental and Phenomenological Distinctions from Polymer-Based DNA Delivery," Journal of Controlled Release 121(1-2):64-73, Aug. 16, 2007.
Germershaus, O., et al., "Gene Delivery Using Chitosan, Trimethyl Chitosan or Polyethylenglycol-graft-trimethyl Chitosan Block Copolymers: Establishment of Structure-Activity Relationships In Vitro," Journal of Controlled Release 125(2):145-154, Jan. 22, 2008.
Guo, Y., et al., "Capillary Electrophoresis Analysis of Poly(ethylene glycol) and Ligand-Modified Polylysine Gene Delivery Vectors," Analytical Biochemistry 363(2):204-209, Apr. 15, 2007.
Jiang, T., et al., "Adsorption of Plasmid DNA onto N,N'-(Dimethylamino)ethyl-methacrylate Graft-Polymerized Poly-L-Lactic Acid Film Surface for Promotion of In-Situ Gene Delivery," Biomacromolecules 8(6):1951-1957, Jun. 2007.
Kim, E.-M., et al., "Monitoring the Effect of PEGylation on Polyethylenimine In Vivo Using Nuclear Imaging Technique," Nuclear Medicine and Biology, 31(6):781-784, Aug. 2004.
Kono, K., et al., "Transfection Activity of Polyamidoamine Dendrimers Having Hydrophobic Amino Acid Residues in the Periphery," Bioconjugate Chemistry 16(1):208-214, Jan. 2005.
Kurisawa, M., et al., "Transfection Efficiency Increases by Incorporating Hydrophobic Monomer Units into Polymeric Gene Carriers," Journal of Controlled Release, 68(1):1-8, Jul. 31, 2000.
Lam, J.K.W., et al., "Phosphocoline-Polycation Diblock Copolymers as Synthetic Vectors for Gene Delivery," Journal of Controlled Release 100(2):293-312, Nov. 24, 2004.
Lomas, H., et al., "Biomimetic pH Sensitive Polymersomes for Efficient DNA Encapsulation and Delivery," Advanced Materials 19(23):4238-4243, Dec. 2007.
Neu, M., et al., "Recent Advances in Rational Gene Transfer Vector Design Based on Poly(ethylene imine) and its Derivatives," Journal of Gene Medicine 7(8):992-1009, Aug. 2005.
Office Action mailed Apr. 25, 2014, from U.S. Appl. No. 12/992,536, filed Feb. 25, 2011, 13 pages.
Office Action mailed Apr. 7, 2014, from U.S. Appl. No. 13/127,959, filed Jul. 27, 2011, 15 pages.
Ogris, M., et al., "PEGylated DNA/transferrin-PEI Complexes: Reduced Interaction with Blood Components, Extended Circulation in Blood and Potential for Systemic Gene Delivery," Gene Therapy 6(4):595-605, Apr. 1999.
Oishi, M., et al., "pH-Responsive Oligodeoxynucleotide (ODN)-Poly(Ethylene Glycol) Conjugate Through Acid-Labile β-Thiopropionate Linkage: Preparation and Polyion Complex Micelle Formation," Biomacromolecules 4(5):1426-1432, Aug. 2003.
Oupicky, D., et al., "DNA Delivery Systems Based on Complexes of DNA with Synthetic Polycations and Their Copolymers," Journal of Controlled Release 65(1-2):149-171, Mar. 1, 2000.
Scales, C.W., et al., "Corona-Stabilized Interpolyelectrolyte Complexes of SiRNA with Nonimmunogenic, Hydrophilic/Cationic Block Copolymers Prepared by Aqueous RAFT Polymerization," Macromolecules 39(20):6871-6881, Oct. 3, 2006.
Takeda, N., et al., "Temperature-Responsive Polymeric Carriers Incorporating Hydrophobic Monomers for Effective Transfection in Small Doses," Journal of Controlled Release 95(2):343-355, Mar. 5, 2004.
Veron, L., et al., "Hydrolyzable p(DMAPEMA) Polymers for Gene Delivery," Macromolecular Bioscience 6(7):540-554, Jul. 14, 2006.
Wei, J.-S., et al., "Temperature- and pH-Sensitive Core-Shell Nanoparticles Self-Assembled From Poly(N-isopropylacrylamide-co-acrylic acid-co-cholesteryl acrylate) for Intracellular Delivery of Anticancer Drugs," Frontiers in Bioscience 10:3058-3067, Sep. 2005.
Yu, H., et al., "A Novel Amphiphilic Double-[60]Fullerene-Capped Triblock Copolymer," Macromolecules 38(23):9889-9893, Nov. 15, 2005.
Zhao, X., et al.,"Nanostructure of Polyplexes Formed Between Cationic Diblock Copolymer and Antisense Oligodeoxynucleotide and its Influence on Cell Transfection Efficiency," Biomacromolecules 8(11):3493-3502, Nov. 12, 2007.
York, A.W. et al., "Advances in the Synthesis of Amphiphilic Block Copolymers via RAFT Polymerization: Stimuli-Responsive Drug and Gene Delivery," Advanced Drug Delivery Reviews 60(9):1018-1036, Jun. 2008.
Stayton, P.S., "Polymeric Carrier," U.S. Appl. No. 14/630,477, filed Feb. 24, 2015.
Stayton, P.S., "Bispecific Intracellular Delivery Vehicles," U.S. Appl. No. 14/957,429, filed Dec. 2, 2015.
Office Action mailed May 20, 2015, from U.S. Appl. No. 13/127,962, filed Jul. 26, 2011, 10 pages.
Georgiou, T.K., and C.S. Patrickios, "Synthesis, Characterization, and DNA Adsorption Studies of Ampholytic Model Conetworks Based on Cross-Linked Star Copolymers," Biomacromolecules 9(2):574-582, Feb. 2008.
Rozema, D.B., et al., "Dynamic PolyConjugates for Targeted In Vivo Delivery of siRNA to Hepatocytes," Proceedings of the National Academy of Sciences of the USA (PNAS) 104(32):12982-12987, Aug. 2007.
Teoh, S.K., et al., "Self-Assembly of Stimuli-Responsive Water Soluble [60]Fullerene End-Capped Ampholytic Block Copolymer," Journal of Physical Chemistry B 109(10):4431-4438, Mar. 2005.
Preliminary Rejection mailed Sep. 15, 2015, issued in corresponding Korean Application No. 10-2010-7027808, filed May 13, 2009, 9 pages.
Office Action mailed Mar. 24, 2016, from U.S. Appl. No. 14/630,477, filed Feb. 24, 2015, 10 pages.
Stayton, P.S., et al., "Micellic Assemblies," U.S. Appl. No. 15/059,026, filed Mar. 2, 2016.
Second Office Action (KR), mailed Jul. 22, 2016, issued in corresponding Korean Application No. 10-2010-7027809, filed May 13, 2009, 9 pages.

* cited by examiner

FIG. 1A

| Polymer | Structure $[D]_{MW_1}$-$[B_x$-$P_y$-$D_z]_{MW_2}$ | Mn Kda | Block Ratio $MW_2/MW_1$ |
|---|---|---|---|
| P7v1 | $[D]_{9.1K}$-$[B_{48}$-$P_{29}$-$D_{23}]_{11.37K}$ | 19 | 1.2 |
| P7v2 | $[D]_{10K}$-$[B_{46}$-$P_{18}$-$D_{37}]_{8.9K}$ | 19 | 0.9 |
| P7v3 | $[D]_{6.5K}$-$[B_{41}$-$P_{39}$-$D_{20}]_{9.5K}$ | 16 | 1.5 |
| P7v6 | $[D]_{9.1K}$-$[B_{52}$-$P_{26}$-$D_{22}]_{21.9K}$ | 31 | 2.4 |

x, y, z ARE MOLE %. MOLECULAR WEIGHTS WERE DETERMINED BY GEL PERMEATION CHROMATOGRAPHY USING PMMA STANDARDS. COMPOSITIONS WERE DETERMINED BY NMR SPECTROSCOPY.

FIG. 1B

| Polymer | Structure $[D]_{MW1}$-$[B$-$P$-$D_{mole\%}]_{MW2}$ | Block Ratio $MW_2/MW_1$ | Particle Size (nm) |
|---|---|---|---|
| PRx-1 | $[D]_{11.3K}$-$[B_{50}$-$P_{30}$-$D_{20}]_{20.7K}$ | 1.83 | 41 |
| PRx-2 | $[D]_{14.5K}$-$[B_{57}$-$P_{23}$-$D_{20}]_{26.4K}$ | 1.82 | 49 |
| PRx-3 | $[D]_{11.5K}$-$[B_{35}$-$P_{27}$-$D_{38}]_{33.4K}$ | 2.92 | 60 |
| PRx-4 | $[D]_{10.7K}$-$[B_{50}$-$P_{27}$-$D_{23}]_{33.8K}$ | 3.16 | 50 |
| PRx-5 | $[D]_{10.7K}$-$[B_{40}$-$P_{31}$-$D_{29}]_{32.2K}$ | 3.00 | 59 |
| PRx-6 | $[D]_{14.5K}$-$[B_{53}$-$P_{31}$-$D_{16}]_{67.0K}$ | 4.62 | 115 |

SYNTHESIS OF [PEGMA$_w$]–[B–P–D]

FIG. 3A
CHARACTERIZATION OF P7-PEGMA100-40 kDa
| | FIRST BLOCK | | SECOND BLOCK | | | | |
|---|---|---|---|---|---|---|---|
| POLYMER | Mn (kDa) | PDI | Mn (kDa) | PDI | %BMA (mol) | %DMAEMA (mol) | %PAA (mol) |
| P7-PEGMA100 40kDa | 40.12 | 1.34 | 59.3 | 1.40 | 53 | 26 | 21 |
FIG. 3B
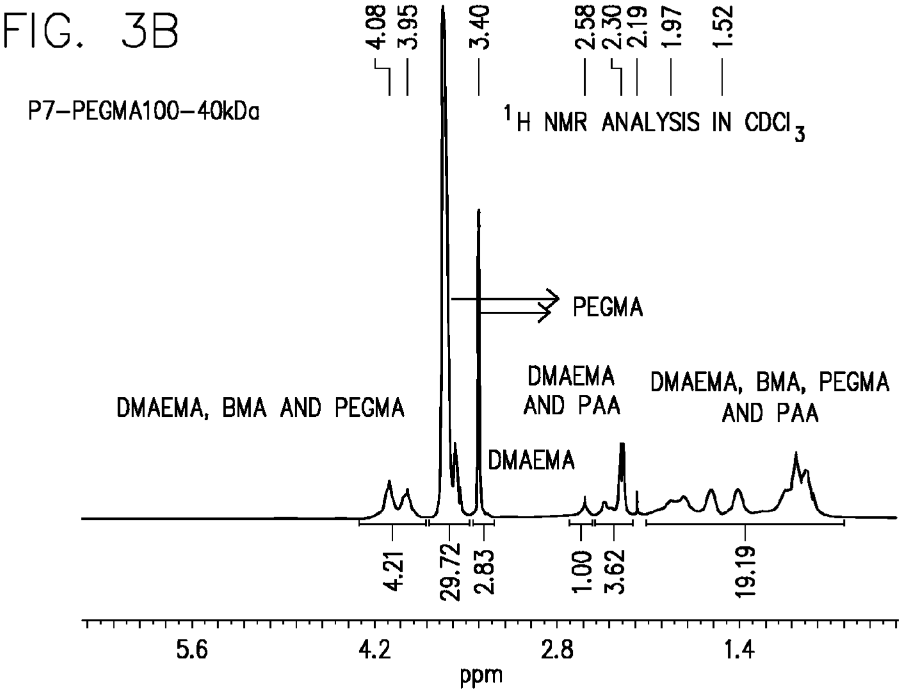
FIG. 3C
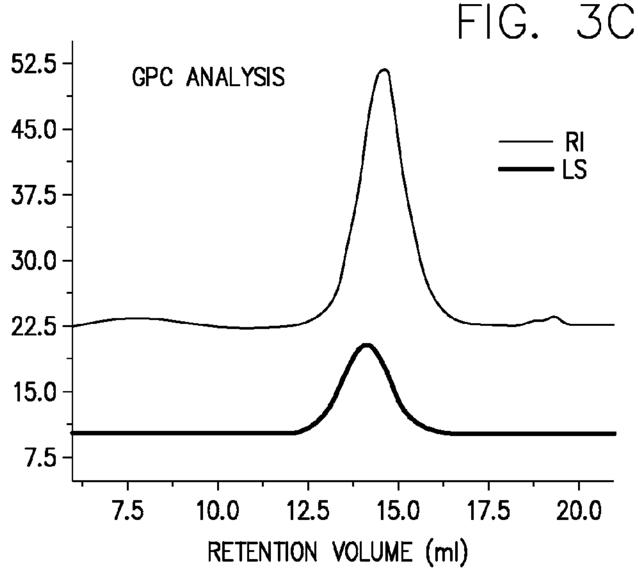

FIG. 4

COMPOSITION AND PROPERTIES OF PEGMA-DMAEMA COPOLYMERS

| | FIRST BLOCK | | | | SECOND BLOCK | | | | |
|---|---|---|---|---|---|---|---|---|---|
| Polymer | Mn (kDa) | PDI | % PEGMA | % DMAEMA | Mn (kDa) | PDI | % BMA | % DMAEMA | %PAA |
| P7-PEGMA100 | 22.24 | 1.34 | 100 | 0 | 45.5 | 1.48 | 50 | 28 | 22 |
| P7-PEGMA20 | 11.44 | 1.33 | 17 | 83 | 41.0 | 1.52 | 56 | 23 | 21 |
| P7-PEGMA10 | 11.01 | 1.31 | 10 | 90 | 42.0 | 1.42 | 51 | 23 | 26 |
| P7-PEGMA5 | 10.60 | 1.17 | 5 | 95 | 27.1 | 1.27 | - | - | - |
| P7-PEGMA-50-14kDa | 14.50 | 1.35 | 46 | 54 | 38.1 | 1.44 | 55 | 25 | 20 |
| P7-PEGMA-50-24kDa | 24.25 | 1.23 | 47 | 53 | 38.4 | 1.45 | 52 | 23 | 25 |

SYNTHESIS OF [PEGMA$_W$–MAA(NHS)]–[B–P–D]

FIG. 6A

RAFT CO-POLYMERIZATION OF PEGMA AND MAA-NHS

[PEGMA]:[MAA-NHS]=75:25

| NAME | FW(g/mol) | EQUIV. | mol | WEIGHT | ACTUAL WEIGHT |
|---|---|---|---|---|---|
| PEGMA | 475 | 112.5 | $5.5958 \times 10^{-3}$ | 2.658g | 2.6641g |
| MAA-NHS | 183.16 | 37.5 | $1.8672 \times 10^{-3}$ | 0.342g | 0.3422g |
| ECT | 263.4 | 1 | $4.9740 \times 10^{-5}$ | 13.1mg | 13.8mg |
| AIBN | 164.21 | 0.04 | $1.9896 \times 10^{-6}$ | 0.33mg | 0.34mg |

DMF = 3.0 g; $N_2$ PURGING: 30 min; CONDUCT POLYMERIZATION AT 68°C. POLYM. TIME=2h 5m COPOLYMERS WERE DIALYZED AGAINST METHANOL (1 L X 8) FOR 50h, USING MWCO MEMBRANE 2K; METHANOL WAS REMOVED UNDER THE HOOD, DRIED UNDER VACUUM 3h, FINALLY LYOPHILIZED FOR 3h.

FIG. 6B

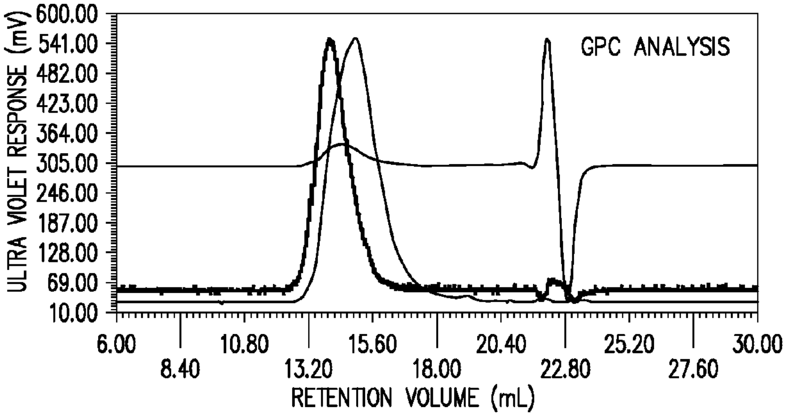

dn/dc=0.0465

$M_n$,GPC=33,000 g/mol

PDI=1.42

FIG. 6C

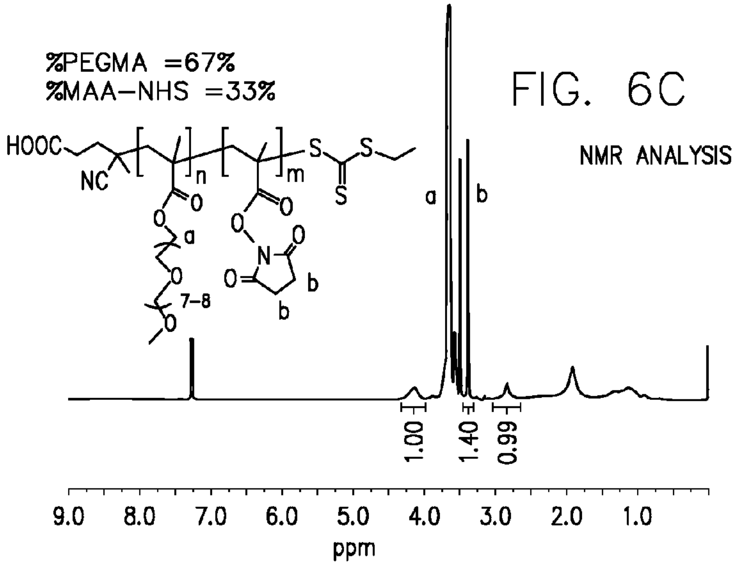

FIG. 7A
[DMAEMA]:[MAA-NHS]=75:25
| NAME | FW(g/mol) | EQUIV. | mol | WEIGHT | ACTUAL WEIGHT |
|---|---|---|---|---|---|
| DMAEMA | 157.21 | 112.5 | 0.013745 | 2.161g | 2.1668g |
| MAA-NHS | 183.16 | 37.5 | $4.5882 \times 10^{-3}$ | 0.839g | 0.8430g |
| ECT | 263.4 | 1 | $2.22186 \times 10^{-4}$ | 32.2mg | 32.4mg |
| AIBN | 164.21 | 0.04 | $4.8774 \times 10^{-5}$ | 0.802mg | 0.812mg |
DMF=3.0g; $N_2$ PURGING: 30 min; CONDUCT POLYMERIZATION AT 68°C. POLYM. TIME=2h 30m
FIG. 7B
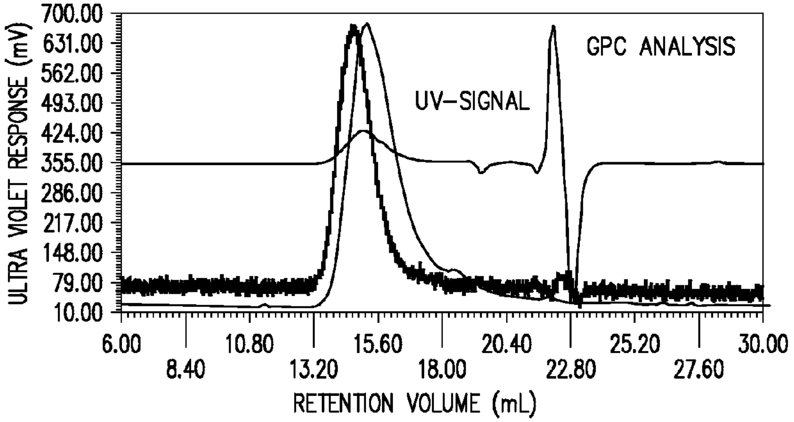
dn/dc=0.0704
$M_n$,GPC=13,660 g/mol
PDI=1.33
FIG. 7C
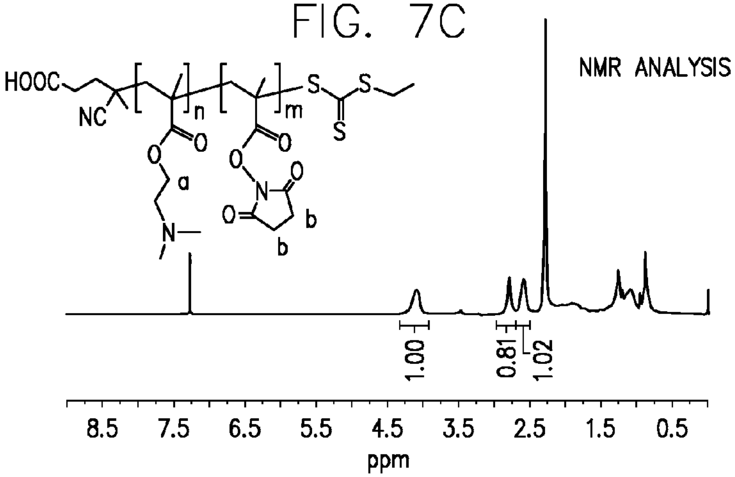
%DMAEMA = 71.2%
%MAA-NHS = 28.8%
RAFT CO-POLYMERIZATION OF DMAEMA AND MAA-NHS

SYNTHESIS OF PDSMA

1

2

SYNTHESIS OF HPMA-PDSMA COPOLYMER FOR siRNA CONJUGATION

POLY[HPMA]-b-[(PAA)(BMA)(DMAEMA)] POLYMER DESIGN.

(1)

(2)

SYNTHESIS OF PYRIDYL DISULFIDE CTA.

POLMER–PEPTIDE CONJUGATION VIA DISULFIDE EXCHANGE REACTION.

SDS PAGE GEL VALIDATING POLYMER-PEPTIDE CONJUGATION VIA A REDUCIBLE DISULFIDE LINKAGE.

pH-DEPENDENT MEMBRANE DISRUPTION BY POLY[HPMA]-b-[(PAA)(BMA)(DMAEMA)].

PEPTIDE

CONJUGATE

POLYMER ENHANCED INTRACELLULAR PEPTIDE DELIVERY.

POLY[HPMA]-b-[(PAA)(BMA)(DMAEMA)]-Anpt-BH3 CONJUGATE INDUCTION OF HeLa CELL DEATH.

BIOACTIVITY OF PEPTIDE CONJUGATES

DIBLOCK COPOLYMERS AND POLYNUCLEOTIDE COMPLEXES THEREOF FOR DELIVERY INTO CELLS

CROSS-REFERENCE

This application claims the benefit of U.S. Provisional Application No. 61/052,908, filed May 13, 2008, U.S. Provisional Application No. 61/052,914, filed May 13, 2008, U.S. Provisional Application No. 61/091,294, filed Aug. 22, 2008, U.S. Provisional Application No. 61/112,054, filed Nov. 6, 2008, U.S. Provisional Application No. 61/112,048, filed Nov. 6, 2008, U.S. Provisional Application No. 61/120,769, filed Dec. 12, 2008, U.S. Provisional Application No. 61/140,779, filed Dec. 24, 2008, U.S. Provisional Application No. 61/140,774, filed Dec. 24, 2008, and U.S. Provisional Application No. 61/171,377, filed Apr. 21, 2009; the contents of all of these documents is herein incorporated by reference in their entirety.

STATEMENT AS TO FEDERALLY SPONSORED RESEARCH

This invention was made with government support under Contract No. 5 R01 EB 2991-03, awarded by the National Institutes of Health. The Government has certain rights in the invention.

STATEMENT OF JOINT RESEARCH AGREEMENT

The subject matter of the claimed invention was made as a result of activities undertaken within the scope of a joint research agreement, within the meaning of 35 U.S.C. §103 (c)(3) and 37 C.F.R. §1.104(c)(4)(ii), by or on behalf of the University of Washington and PhaseRx, Inc., that was in effect on or before the claimed invention was made.

FIELD

This invention relates to the fields of organic chemistry, polymer chemistry, biochemistry, molecular biology, and medicine. In particular it relates to copolymers (e.g., diblock copolymers) and complexes thereof with polynucleotides to be used as vehicles for delivery of the polynucleotides into living cells.

BACKGROUND OF THE INVENTION

In certain instances, it is beneficial to provide therapeutic agents (e.g., oligonucleotides) to living cells. In some instances, delivery of such polynucleotides to a living cell provides a therapeutic benefit.

SUMMARY

In some embodiments, provided herein are copolymers comprising at least two blocks, the first block comprising at least one constitutional unit that is hydrophilic (e.g., at about physiologic pH), and the second block comprising a plurality of hydrophobic moieties. In certain embodiments, the second block further comprises a chargeable species, in either the charged or non-charged state, that is anionic at physiologic pH. However, when the pH is at about the $pK_a$ of the chargeable species, there will exist an equilibrium distribution of chargeable species in both forms, that is about 50% will be anionic and about 50% will be non-charged.

The further the pH is from the $pK_a$ of the chargeable species, there will be a corresponding shift in this equilibrium such that at higher pH values, the anionic form will predominate and at lower pH values, the uncharged form will predominate. The embodiments described herein include the form of the copolymers at any pH value. At a pH value of an endosome (an endosomal pH), the chargeable species will be predominantly in the uncharged form.

Preferably, in certain instances, wherein a polymer described herein is in contact with a cellular membrane, it disrupts or otherwise destabilizes the membrane and enters the intracellular environment. In specific embodiments, a polymer provided herein is endosomolytic or otherwise destabilizing of an endosomal membrane In certain embodiments, provided herein is a cellular membrane destabilizing (e.g., an endosomolytic or an endosome-membrane destabilizing) copolymer comprising:

(a) a first block, the first block being a hydrophilic block; and (b) a second block, the second block being a membrane destabilizing hydrophobic block comprising:

(i) a first chargeable species that is anionic at about physiologic pH (ii) a second chargeable species that cationic at about physiologic pH.

In some embodiments, provided herein is a cellular membrane destabilizing (e.g., an endosomolytic or an endosome-membrane destabilizing) copolymer comprising:

(a) a first block, the first block being a hydrophilic block comprising a first chargeable species that is cationic at about physiologic pH;

(b) a second block, the second block being a membrane destabilizing hydrophobic block comprising:

(i) a second chargeable species that is anionic at about neutral pH; and (ii) a third chargeable species that is cationic at about physiologic pH; and (c) an oligonucleotide associated with the first block.

In certain embodiments, provided herein is a cellular membrane destabilizing (e.g., an endosomolytic or an endosome-membrane destabilizing) copolymer comprising:

(a) a first block, the first block being a hydrophilic block;

(b) a second block, the second block being a membrane destabilizing hydrophobic block comprising an acrylic acid residue or alkylacrylic acid residue.

In one aspect the current invention relates to a copolymer (e.g., diblock copolymer) comprising:

a first block comprising a first constitutional unit that is hydrophilic at normal physiological pH;

a second block comprising:

a second constitutional unit that is cationic at normal physiological pH and which can be the same as or different than the first constitutional unit;

a third constitutional unit that is anionic at normal physiological pH;

a hydrophobicity-enhancing moiety wherein:

the hydrophobicity-enhancing moiety is covalently bonded to the second constitutional unit; or, the hydrophobicity enhancing moiety is covalently bonded to the third constitutional unit; or, the hydrophobicity-enhancing moiety is comprised in a fourth constitutional unit of the second block; or, any combination of the above; and, the second block is substantially neutral in overall charge.

In various embodiments, the first constitutional unit is cationic at normal physiological pH (i.e., about physiologic pH), is anionic at normal physiological pH, is neutral at normal physiological pH, or is zwitterionic at normal physiological pH. In some embodiments, the first block of the copolymer is polycationic at normal physiological pH, is polyanionic at normal physiological pH, is neutral at normal physiological pH, or is polyzwitterionic at normal physiological pH. In further embodiments, the first block of the copolymer has substantially the same ionic properties at endosomal pH as at normal physiological pH, e.g., is polycationic at endosomal pH, is polyanionic at endosomal pH, is neutral at endosomal pH, or is polyzwitterionic at endosomal pH.

In one aspect the current invention relates to a copolymer (e.g., diblock copolymer) comprising:

a first block comprising a first constitutional unit that is cationic at normal physiological pH;

a second block comprising:

a second constitutional unit that is cationic at normal physiological pH and which can be the same as or different than the first constitutional unit;

a third constitutional unit that is anionic at normal physiological pH; a hydrophobicity-enhancing moiety wherein:

the hydrophobicity-enhancing moiety is covalently bonded to the second constitutional unit; or, the hydrophobicity enhancing moiety is covalently bonded to the third constitutional unit; or, the hydrophobicity-enhancing moiety is comprised in a fourth constitutional unit of the second block; or, any combination of the above; and, the second block is substantially neutral in overall charge.

In an aspect of this invention, the first constitutional unit comprises a cationic nitrogen species (i.e., a nitrogen species that is cationic at normal physiological pH). In an aspect of this invention the cationic nitrogen species is an ammonium species. In an aspect of this invention the second constitutional unit is the same as the first constitutional unit. In an aspect of this invention the anionic species comprises a carboxylic acid anion. In an aspect of this invention the first block further comprises a charge neutral constitutional unit randomly interspersed among the first constitutional units. In an aspect of this invention, the first and/or second block comprises at least one reactive or amenable to modification groups. In an aspect of this invention, if present, the fourth constitutional unit comprises from about 10% to about 60% by weight of the second block.

In certain embodiments, the first polymer block is approximately 10,000 daltons in size, or about 2,000 daltons to about 30,000 daltons, or about 8,500 daltons to about 13,000 daltons. In some embodiments, the first polymer block has a net positive charge similar in absolute value to the net negative charge on the siRNA molecule being delivered.

In some embodiments, the second polymer block is approximately equal to the first polymer block in molecular weight, or about 0.2-5 times, or about 1-3 times the size of the first polymer block and in most preferred embodiments the second polymer block is approximately 2-3 (two to three) times the size of the first polymer block.

In some embodiments, the hydrophilic, charged block is complexed with (used interchangeably herein with "associated with" or "attached to", e.g., by one or more covalent bond, one or more ionical interaction, a combination thereof, or the like) at least one nucleotide, including a polynucleotide, e.g., an siRNA.

In an aspect of this invention, the polynucleotide block is attached to one of the polymer blocks through an optionally cleavable covalent bond. In an aspect of this invention, the polynucleotide acid is selected from the group consisting of DNA, RNA and natural and synthetic analogs thereof. In an aspect of this invention the polynucleotide is antisense. In an aspect of this invention the polynucleotide is RNA. In an aspect of this invention the RNA is selected from the group consisting of mRNA, piRNA, miRNA and siRNA. In an aspect of this invention the RNA is siRNA.

In an aspect of this invention each of the constitutional units is independently derived from an ethylenic monomer and synthesis of the copolymer comprises living polymerization.

In an aspect of this invention, the ethylenic monomer is an acrylic monomer.

Provided in certain embodiments herein is a diblock copolymer, having the chemical Formula I:

(I)

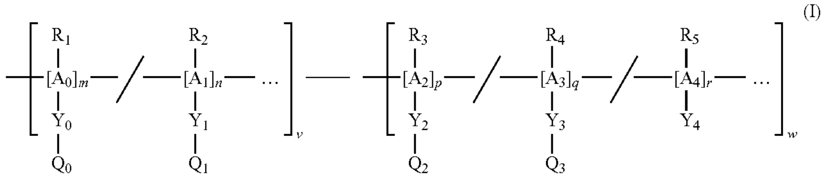

In some embodiments:

$A_0$, $A_1$, $A_2$, $A_3$ and $A_4$ are selected from the group consisting of —C—C—, —C(O)(C)$_a$C(O)O—, —O(C)$_a$C(O)— and —O(C)$_b$O—; wherein, a is 1-4;

b is 2-4;

$Y_4$ is selected from the group consisting of hydrogen, (1C-10C)alkyl, (3C-6C)cycloalkyl, O-(1C-10C)alkyl, —C(O)O(1C-10C)alkyl, C(O)NR$_6$(1C-10C) and aryl, any of which is optionally substituted with one or more fluorine groups;

$Y_0$, $Y_1$ and $Y_2$ are independently selected from the group consisting of a covalent bond, (1C-10C)alkyl-, —C(O)O(2C-10C) alkyl-, —OC(O)(1C-10C) alkyl-, —O(2C-10C)alkyl- and —S(2C-10C)alkyl- —C(O)NR$_6$(2C-10C) alkyl-;

$Y_3$ is selected from the group consisting of a covalent bond, (1C-10C)alkyl and (6C-10C)aryl; wherein tetravalent carbon atoms of $A_1$-$A_4$, that are not fully substituted with $R_1$-$R_5$ and $Y_0$-$Y_4$ are completed with an appropriate number of hydrogen atoms;

each $R_1$, $R_2$, $R_3$, $R_4$, $R_5$, and $R_6$ are independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;

$Q_0$ is a residue selected from the group consisting of residues which are hydrophilic at physiologic pH and are at least partially positively charged at physiologic pH (e.g., amino, alkylamino, ammonium, alkylammonium, guanidine, imidazolyl, pyridyl, or the like); at least partially negatively charged at physiologic pH but undergo protonation at lower pH (e.g., carboxyl, sulfonamide, boronate, phosphonate, phosphate, or the like); substantially neutral (or non-charged) at physiologic pH (e.g., hydroxy, polyoxylated alkyl, polyethylene glycol, polypropylene glycol, thiol, or the like); at least partially zwitterionic at physiologic pH (e.g., a monomeric residue comprising a phosphate group and an ammonium group at physiologic pH); conjugatable or functionalizable residues (e.g. residues that comprise a reactive group, e.g., azide, alkyne, succinimide ester, tetrafluorophenyl ester, pentafluorophenyl ester, p-nitrophenyl ester, pyridyl disulfide, or the like); or hydrogen;

$Q_1$ is a residue which is hydrophilic at physiologic pH, and is at least partially positively charged at physiologic pH (e.g., amino, alkylamino, ammonium, alkylammonium, guanidine, imidazolyl, pyridyl, or the like); at least partially negatively charged at physiologic pH but undergoes protonation at lower pH (e.g., carboxyl, sulfonamide, boronate, phosphonate, phosphate, or the like); substantially neutral at physiologic pH (e.g., hydroxy, polyoxylated alkyl, polyethylene glycol, polypropylene glycol, thiol, or the like); or at least partially zwitterionic at physiologic pH (e.g., a monomeric residue comprising a phosphate group and an ammonium group at physiologic pH);

$Q_2$ is a residue which is positively charged at physiologic pH, including but not limited to amino, alkylamino, ammonium, alkylammonium, guanidine, imidazolyl, and pyridyl;

$Q_3$ is a residue which is negatively charged at physiologic pH, but undergoes protonation at lower pH, including but not limited to carboxyl, sulfonamide, boronate, phosphonate, and phosphate;

m is 0 to less than 1.0 (e.g., 0 to about 0.49);

n is greater than 0 to 1.0 (e.g., about 0.51 to about 1.0); wherein $m+n=1$ p is about 0.1 to about 0.9 (e.g., about 0.2 to about 0.5);

q is about 0.1 to about 0.9 (e.g., about 0.2 to about 0.5); wherein:

r is 0 to about 0.8 (e.g., 0 to about 0.6); wherein $p+q+r=1$ v is from about 1 to about 25 kDa; and, w is from about 1 to about 50 kDa.

In a specific embodiment, v is about 5 to about 25 kDa. In further or alternative specific embodiments, w is about 1 to about 50 kDa.

In some embodiments, the number or ratio of monomeric residues represented by p and q are within about 30% of each other, about 20% of each other, about 10% of each other, or the like. In specific embodiments, p is substantially the same as q. In certain embodiments, at least partially charged generally includes more than a trace amount of charged species, including, e.g., at least 20% of the residues are charged, at least 30% of the residues are charged, at least 40% of the residues are charged, at least 50% of the residues are charged, at least 60% of the residues are charged, at least 70% of the residues are charged, or the like.

In certain embodiments, m is 0 and $Q_1$ is a residue which is hydrophilic and substantially neutral (or non-charged) at physiologic pH. That is, at physiologic pH, any chargeable species on $Q_1$ is predominantly in a neutral form. In some embodiments, substantially non-charged includes, e.g., less than 5% are charged, less than 3% are charged, less than 1% are charged, or the like. In certain embodiments, m is 0 and $Q_1$ is a residue which is hydrophilic and at least partially cationic at physiologic pH. In certain embodiments, m is 0 and $Q_1$ is a residue which is hydrophilic and at least partially anionic at physiologic pH. In certain embodiments, m is >0 and n is >0 and one of and $Q_0$ or $Q_1$ is a residue which is hydrophilic and at least partially cationic at physiologic pH and the other of $Q_0$ or $Q_1$ is a residue which is hydrophilic and is substantially neutral at physiologic pH. In certain embodiments, m is >0 and n is >0 and one of and $Q_0$ or $Q_1$ is a residue which is hydrophilic and at least partially anionic at physiologic pH and the other of $Q_0$ or $Q_1$ is a residue which is hydrophilic and is substantially neutral at physiologic pH. In certain embodiments, m is >0 and n is >0 and $Q_1$ is a residue which is hydrophilic and at least partially cationic at physiologic pH and $Q_0$ is a residue which is hconjugatable or functionalizable residues. In certain embodiments, m is >0 and n is >0 and $Q_1$ is a residue which is hydrophilic and substantially neutral at physiologic pH and $Q_0$ is a residue which is hconjugatable or functionalizable residues.

Provided in certain embodiments herein is copolymer having at least two blocks, the first block having the chemical Formula Ia, the second block having the chemical Formula Ib, wherein each of the terms described therein are as described above:

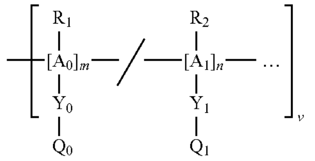

(Ia)

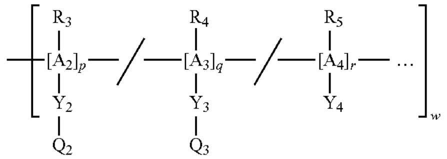

(Ib)

In certain embodiments, provided herein is a compound of Formula II:

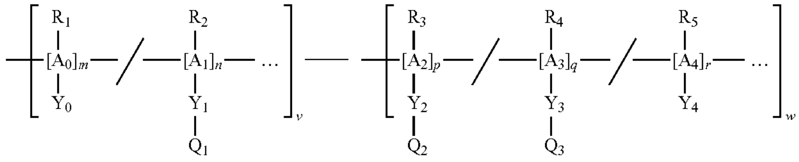

(II)

In some embodiments:

$A_0$, $A_1$, $A_2$, $A_3$ and $A_4$ are selected from the group consisting of —C—C—, —C(O)(C)$_a$C(O)O—, —O(C)$_a$C(O)— and —O(C)$_b$O—; wherein, a is 1-4;

b is 2-4;

$Y_0$ and $Y_4$ are independently selected from the group consisting of hydrogen, (1C-10C)alkyl, (3C-6C)cycloalkyl, O-(1C-10C)alkyl, —C(O)O(1C-10C)alkyl, C(O)NR$_6$(1C-10C) and aryl, any of which is optionally substituted with one or more fluorine groups;

$Y_1$ and $Y_2$ are independently selected from the group consisting of a covalent bond, (1C-10C)alkyl-, —C(O)O(2C-10C) alkyl-, —OC(O)(1C-10C) alkyl-, —O(2C-10C)alkyl- and —S(2C-10C)alkyl- —C(O)NR$_6$(2C-10C) alkyl;

$Y_3$ is selected from the group consisting of a covalent bond, (1C-10C)alkyl and (6C-10C)aryl; wherein tetravalent carbon atoms of $A_1$-$A_4$ that are not fully substituted with $R_1$-$R_{51}$ and $Y_0$-$Y_4$ are completed with an appropriate number of hydrogen atoms;

each $R_1$, $R_2$, $R_3$, $R_4$, $R_5$, and $R_6$ are independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;

$Q_1$ and $Q_2$ are residues which are positively charged at physiologic pH, including but not limited to amino, alkylamino, ammonium, alkylammonium, guanidine, imidazolyl, and pyridyl;

$Q_3$ is a residue which is negatively charged at physiologic pH, but undergoes protonation at lower pH, including but not limited to carboxyl, sulfonamide, boronate, phosphonate, and phosphate;

m is 0 to about 0.49;

n is about 0.51 to about 1.0; wherein $$m+n=1$$

p is about 0.2 to about 0.5;

q is about 0.2 to about 0.5; wherein:

p is substantially the same as q;

r is 0 to about 0.6; wherein $$p+q+r=1$$

v is from about 5 to about 25 kDa; and, w is from about 5 to about 50 kDa.

Provided in some embodiments herein is a diblock copolymer, having (at normal physiological pH) the chemical formula III:

(III)

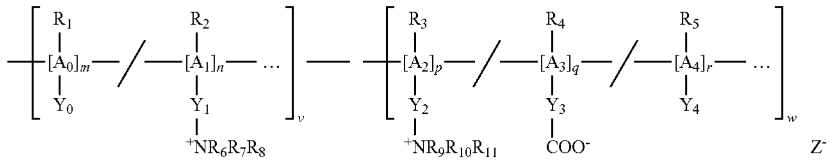

In some embodiments:

$A_0$, $A_1$, $A_2$, $A_3$ and $A_4$ are selected from the group consisting of —C—C—, —C(O)(C)$_a$C(O)O—, —O(C)$_a$C(O)— and —O(C)$_b$O—; wherein, a is 1-4;

b is 2-4;

$R_1$, $R_2$, $R_3$, $R_4$, $R_5$, $R_6$, $R_7$, $R_8$, $R_9$, $R_{10}$ and $R_{11}$ are independently selected from the group consisting of hydrogen, (1C-5C)alkyl, (3C-6C)cycloalkyl and phenyl, any of which may be optionally substituted with one or more fluorine atoms;

$Y_0$ and $Y_4$ are independently selected from the group consisting of hydrogen, (1C-10C)alkyl, (3C-6C)cycloalkyl, O-(1C-10C)alkyl, —C(O)O(1C-10C)alkyl and phenyl, any of which is optionally substituted with one or more fluorine groups;

$Y_1$ and $Y_2$ are independently selected from the group consisting of a covalent bond, (1C-10C)alkyl-, —C(O)O(2C-10C) alkyl-, —OC(O)(1C-10C) alkyl-, —O(2C-10C)alkyl- and —S(2C-10C)alkyl-;

$Y_3$ is selected from the group consisting of a covalent bond, (1C-5C)alkyl and phenyl;

wherein tetravalent carbon atoms of $A_1$-$A_4$ that are not fully substituted with $R_7$-$R_{11}$ and $Y_0$-$Y_4$ are completed with an appropriate number of hydrogen atoms;

Z is a physiologically acceptable counterion, m is 0 to about 0.49;

n is about 0.51 to about 1.0; wherein $$m+n=1$$

p is about 0.2 to about 0.5;

q is about 0.2 to about 0.5; wherein:

p is substantially the same as q;

r is 0 to about 0.6; wherein $$p+q+r=1$$

v is from about 5 to about 25 kDa; and, w is from about 5 to about 50 kDa.

In an aspect of this invention, $A_1$ is —C—C—

$Y_1$ is —C(O)OCH$_2$CH$_2$—;

$R_6$ is hydrogen;

$R_7$ and $R_8$ are each —CH$_3$; and, $R_2$ is —CH$_3$.

In an aspect of this invention, $A_2$ is —C—C—;

$Y_2$ is —C(O)OCH$_2$CH$_2$—, $R_9$ is hydrogen;

$R_{10}$ and $R_{11}$ are each —CH$_3$; and, $R_3$ is —CH$_3$.

In an aspect of this invention, $A_3$ is —C—C—;

$R_3$ is CH$_3$CH$_2$CH$_2$—;

$Y_3$ is a covalent bond; and $Z^-$ is a physiologically acceptable anion (e.g., polycation or plurality of cations).

In certain embodiments:

$A_4$ is —C—C—;

$R_5$ is selected from the group consisting of hydrogen and —CH$_3$; and, $Y_4$ is —C(O)O(CH$_2$)$_3$CH$_3$.

In some embodiments:

$A_0$ is C—C—

$R_1$ is selected from the group consisting of hydrogen and (1C-3C)alkyl; and $Y_0$ is selected from the group consisting of —C(O)O(1C-3C)alkyl.

In some embodiments, m is 0. In certain embodiments, r is 0. In some embodiments, m and r are both 0.

In certain embodiments, provided herein is a method of delivering a polynucleotide into a cell, comprising contacting the cell with a polymer: polynucleotide complex hereof. In specific embodiments, the polymer: polynucleotide complex is attached in any suitable manner including, by way of non-limiting example, ionic and non-ionic interactions, such as one or more covalent bond, combinations thereof, or the like. In a specific embodiment, provided herein is a method of delivering a polynucleotide into a cell, comprising contacting the cell with a covalent conjugate of the polymer and polynucleotide.

In an aspect of this invention, the polynucleotide is selected from the group consisting of DNA, RNA and natural and synthetic analogs thereof.

In an aspect of this invention, the DNA, RNA or natural or synthetic analogs thereof is antisense. In an aspect of this invention, the polynucleotide is RNA. In an aspect of this invention, the RNA is siRNA. In an aspect of this invention, the siRNA is delivered to a cell in vivo. In an aspect of this invention, the polymer of this invention is attached or complexed to a targeting moiety. In an aspect of this invention, the targeting moiety is covalently attached to the α-end of the copolymer (e.g., diblock copolymer). In an aspect of this invention, the targeting moiety is covalently attached to the ω-end of the copolymer, or is covalently attached to a pendant group of the copolymer (e.g., diblock copolymer). In an aspect of this invention, the targeting moiety is selected form but not limited to antibodies, antibody fragments, antibody-like molecules, peptides, cyclic peptides, and small molecules.

INCORPORATION BY REFERENCE

All publications and patent applications mentioned in this specification are herein incorporated by reference for the purposes cited to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A and 1B are illustrative summaries of various polymers described herein.

FIGS. 3A, 3B, and 3C are illustrative characterizations of P7-PEGMA 100-40 kDa.

FIG. 4 is an illustrative description of the composition and properties of PEGMA-DMAEMA copolymers

FIGS. 6A, 6B, and 6C are illustrative RAFT copolymerizations of PEGMA and MAA-NHS.

FIGS. 7A, 7B, and 7C are illustrative RAFT copolymerizations of DMAEMA and MAA-NHS.

Figure 2:
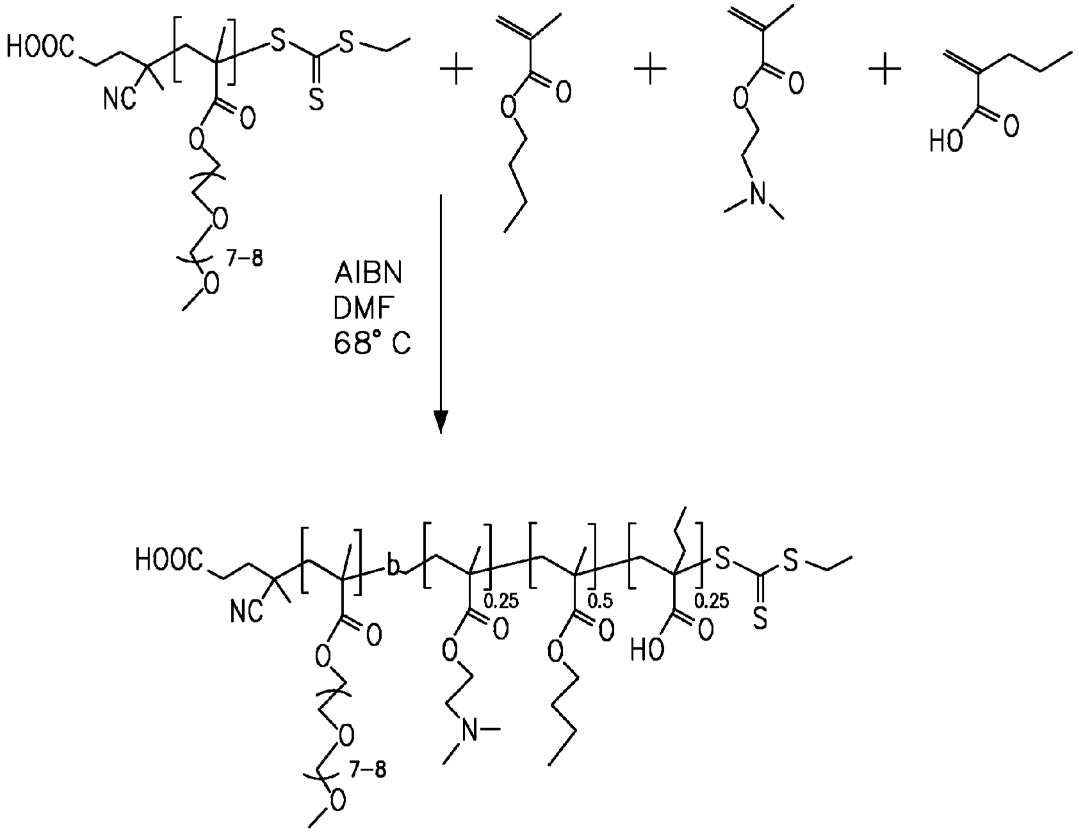
FIG. 2 is an illustrative synthesis of [PEGMAw]-[B-P-D]

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Polymer

Provided in certain embodiments, the present invention provides carrier polymers and polymer: polynucleotide constructs. In certain instances, these polymers and polymer: polynucleotide constructs meet the need for a safe, robust system for delivering therapeutic polynucleotides into cells.

In certain embodiments, provided herein is a cellular membrane destabilizing (e.g., an endosomolytic or an endosome-membrane destabilizing) copolymer comprising:

(a) a first block, the first block being a hydrophilic block; and (b) a second block, the second block being a membrane destabilizing hydrophobic block comprising:

(i) a first chargeable species that is anionic at about physiologic pH (ii) a second chargeable species that cationic at about physiologic pH.

In some embodiments, provided herein is a cellular membrane destabilizing (e.g., an endosomolytic or an endosome-membrane destabilizing) copolymer comprising:

(a) a first block, the first block being a hydrophilic block comprising a first chargeable species that is cationic at about physiologic pH;

(b) a second block, the second block being a membrane destabilizing hydrophilic block comprising:

(i) a second chargeable species that is anionic at about neutral pH; and (ii) a third chargeable species that is cationic at about physiologic pH; and (c) an oligonucleotide associated with the first block.

In specific embodiments of the polymers described herein, each chargeable species is present on a different constitutional unit. In some embodiments, a first constitutional unit comprises the first chargeable species. In further or alternative embodiments, a second constitutional unit comprises the second chargeable species. In further or alternative embodiments, a third constitutional unit comprises the third chargeable species.

Some of the constitutional units of this invention are stated to be cationic or anionic at normal physiological pH. Thus, in certain instances, at normal physiological pH, the species have a pKa that results in it being protonated (cationic, positively charged) or deprotonated (anionic, negatively charged). Presently preferred cationic species at physiological pH are nitrogen species such as ammonium, —NRR'R", guanidinium (—NRC(═NR'H)$^+$NR"R"', ignoring canonical forms that are known to those skilled in the art) wherein the R groups are independently hydrogen, alkyl, cycloalkyl or aryl or two R groups bonded to the same or adjacent nitrogen atoms may be also be joined to one another to form a heterocyclic species such as pyrrole, imidazole, indole and the like. Monomeric residues or constitutional units described herein as cationic at normal physiological pH comprise a species charged or chargeable to a cation, including a deprotonatable cationic species.

In various embodiments described herein, constitutional units, that are cationic or positively charged at physiological pH (including, e.g., certain hydrophilic constitutional units) described herein comprise one or more amino groups, alkylamino groups, guanidine groups, imidazolyl groups, pyridyl groups, or the like, or the protonated, alkylated or otherwise charged forms thereof. In some embodiments, constitutional units that are cationic at normal physiological pH that are utilized herein include, by way of non-limiting example, monomeric residues of dialkylaminoalkylmethacrylates (e.g., DMAEMA). In various embodiments described herein, constitutional units, that are anionic or negatively charged at physiological pH (including, e.g., certain hydrophilic constitutional units) described herein comprise one or more acid group or conjugate base thereof, including, by way of non-limiting example, carboxylate, sulfonamide, boronate, phosphonate, phosphate, or the like. In some embodiments, constitutional units that are anionic or negatively charged at normal physiological pH that are utilized herein include, by way of non-limiting example, monomeric residues of acrylic acid, alkyl acrylic acid (e.g., methyl acrylic acid, ethyl acrylic acid, propyl acrylic acid, etc.), or the like. In various embodiments described herein, hydrophilic constitutional units that are neutral at physiologic pH comprise one or more hydrophilic group, e.g., hydroxy, polyoxylated alkyl, polyethylene glycol, polypropylene glycol, thiol, or the like. In some embodiments, hydrophilic constitutional units that are neutral at normal physiological pH that are utilized herein include, by way of non-limiting example, monomeric residues of PEGylated acrylic acid, PEGylated methacrylic acid, hydroxyalkylacrylic acid, hydroxyalkylalkacrylic acid (e.g., HPMA), or the like. In various embodiments described herein, hydrophilic constitutional units that are zwitterionic at physiologic pH comprise an anionic or negatively charged group at physiologic pH and a cationic or positively charged group at physiologic pH. In some embodiments, hydrophilic constitutional units that are zwitterionic at normal physiological pH that are utilized herein include, by way of non-limiting example, monomeric residues of comprising a phosphate group and an ammonium group at physiologic pH, such as set forth in U.S. Pat. No. 7,300,990, which is hereby incorporated herein for such disclosure, or the like.

In certain embodiments, polymers provided herein further comprise one or more constitutional unit comprising a conjugatable or functionalizable side chain (e.g., a pendant group of a monomeric residue). In some instances, a conjugatable or functionalizable side chain is a group bearing one or more reactive groups that can be used for post-polymerization introduction of additional functionalities via know in the art chemistries, for example, "click" chemistry (for example of "click" reactions, see Wu, P.; Fokin, V. V. Catalytic Azide-Alkyne Cycloaddition: Reactivity and Applications. *Aldrichim. Acta,* 2007, 40, 7-17). In certain embodiments, conjugatable or functionalizable side chains provided herein comprise one or more of any suitable activated group, such as but not limited to N-hydrosuccinimide (NHS) ester, HOBt (1-hydroxybenzotriazole) ester, p-nitrophenyl ester, tetrafluorophenyl ester, pentafluorophenyl ester, pyridyl disulfide group or the like.

In some embodiments, constitutional units that are anionic at normal physiological pH comprise carboxylic acids such as, without limitation, monomeric residues of 2-propyl acrylic acid (i.e., the constitutional unit derived from it, 2-propylpropionic acid, $—CH_2C((CH_2)_2CH_3)(COOH)—$(PAA)), although any organic or inorganic acid that can be present, either as a protected species, e.g., an ester, or as the free acid, in the selected polymerization process is also within the contemplation of this invention. Anionic monomeric residues or constitutional units described herein comprise a species charged or chargeable to an anion, including a protonatable anionic species. In certain instances, anionic monomeric residues can be anionic at neutral pH 7.0.

Monomers such as maleic-anhydride, (Scott M. Henry, Mohamed E. H. El-Sayed, Christopher M. Pirie, Allan S. Hoffman, and Patrick S. Stayton "pH-Responsive Poly(styrene-alt-maleic anhydride) Alkylamide Copolymers for Intracellular Drug Delivery" *Biomacromolecules* 7:2407-2414, 2006) may also be used for introduction of negatively charged units (e.g., the third constitutional unit) into the second block. In such embodiments, the negatively charged constitutional unit is a maleic anhydride monomeric residue.

An embodiment of this invention is a polymer having the following general structure of Formula I:

(I)

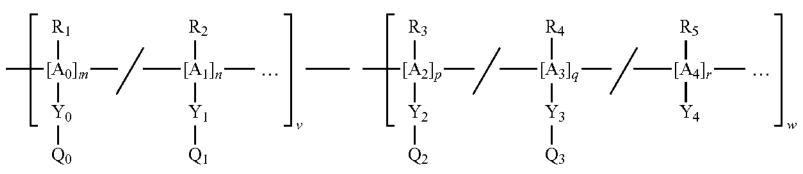

In some embodiments:

$A_0$, $A_1$, $A_2$, $A_3$ and $A_4$ are selected from the group consisting of —C—, —C—C—, —C(O)(C)$_a$C(O)O—, —O(C)$_a$C(O)— and —O(C)$_b$O—; wherein, a is 1-4;

b is 2-4;

$Y_4$ is selected from the group consisting of hydrogen, (1C-10C)alkyl, (3C-6C)cycloalkyl, O-(1C-10C)alkyl, —C(O)O(1C-10C)alkyl, C(O)NR$_6$(1C-10C), (4C-10C)heteroaryl and (6C-10C)aryl, any of which is optionally substituted with one or more fluorine groups;

$Y_0$, $Y_1$ and $Y_2$ are independently selected from the group consisting of a covalent bond, (1C-10C)alkyl-, —C(O)O(2C-10C) alkyl-, —OC(O)(1C-10C) alkyl-, —O(2C-10C)alkyl- and —S(2C-10C)alkyl-, —C(O)NR$_6$(2C-10C) alkyl-, -(4C-10C)heteroaryl- and -(6C-10C)aryl-;

$Y_3$ is selected from the group consisting of a covalent bond, -(1C-10C)alkyl-, -(4C-10C)heteroaryl- and -(6C-10C)aryl-; wherein tetravalent carbon atoms of $A_1$-$A_4$ that are not fully substituted with $R_1$-$R_5$ and $Y_0$-$Y_4$ are completed with an appropriate number of hydrogen atoms;

$R_1$, $R_2$, $R_3$, $R_4$, $R_5$, and $R_6$ are independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;

$Q_0$ is a residue selected from the group consisting of residues which are hydrophilic at physiologic pH, and are at least partially positively charged at physiologic pH (e.g., amino, alkylamino, ammonium, alkylammonium, guanidine, imidazolyl, pyridyl, or the like); at least partially negatively charged at physiologic pH but undergo protonation at lower pH (e.g., carboxyl, sulfonamide, boronate, phosphonate, phosphate, or the like); substantially neutral (or non-charged) at physiologic pH (e.g., hydroxy, polyoxylated alkyl, polyethylene glycol, polypropylene glycol, thiol, or the like); at least partially zwitterionic at physiologic pH (e.g., a monomeric residue comprising a phosphate group and an ammonium group at physiologic pH); conjugatable or functionalizable residues (e.g. residues that comprise a reactive group, e.g., azide, alkyne, succinimide ester, tetrafluorophenyl ester, pentafluorophenyl ester, p-nitrophenyl ester, pyridyl disulfide, or the like); or hydrogen;

$Q_1$ is a residue which is hydrophilic at physiologic pH, and is at least partially positively charged at physiologic pH (e.g., amino, alkylamino, ammonium, alkylammonium, guanidine, imidazolyl, pyridyl, or the like); at least partially negatively charged at physiologic pH but undergoes protonation at lower pH (e.g., carboxyl, sulfonamide, boronate, phosphonate, phosphate, or the like); substantially neutral at physiologic pH (e.g., hydroxy, polyoxylated alkyl, polyethylene glycol, polypropylene glycol, thiol, or the like); or at least partially zwitterionic at physiologic pH (e.g., comprising a phosphate group and an ammonium group at physiologic pH);

$Q_2$ is a residue which is positively charged at physiologic pH, including but not limited to amino, alkylamino, ammonium, alkylammonium, guanidine, imidazolyl, and pyridyl;

$Q_3$ is a residue which is negatively charged at physiologic pH, but undergoes protonation at lower pH, including but not limited to carboxyl, sulfonamide, boronate, phosphonate, and phosphate;

m is about 0 to less than 1.0 (e.g., 0 to about 0.49);

n is greater than 0 to about 1.0 (e.g., about 0.51 to about 1.0); wherein $$m+n=1$$

p is about 0.1 to about 0.9 (e.g., about 0.2 to about 0.5);

q is about 0.1 to about 0.9 (e.g., about 0.2 to about 0.5); wherein:

r is 0 to about 0.8 (e.g., 0 to about 0.6); wherein $$p+q+r=1$$

v is from about 1 to about 25 kDa, or about 5 to about 25 kDa; and, w is from about 1 to about 50 kDa, or about 5 to about 50 kDa.

In some embodiments, the number or ratio of monomeric residues represented by p and q are within about 30% of each other, about 20% of each other, about 10% of each other, or the like. In specific embodiments, p is substantially the same as q. In certain embodiments, at least partially charged generally includes more than a trace amount of charged species, including, e.g., at least 20% of the residues are charged, at least 30% of the residues are charged, at least 40% of the residues are charged, at least 50% of the residues are charged, at least 60% of the residues are charged, at least 70% of the residues are charged, or the like.

In certain embodiments, m is 0 and $Q_1$ is a residue which is hydrophilic and substantially neutral (or non-charged) at physiologic pH. In some embodiments, substantially non-charged includes, e.g., less than 5% are charged, less than 3% are charged, less than 1% are charged, or the like. In certain embodiments, m is 0 and $Q_1$ is a residue which is hydrophilic and at least partially cationic at physiologic pH. In certain embodiments, m is 0 and $Q_1$ is a residue which is hydrophilic and at least partially anionic at physiologic pH. In certain embodiments, m is >0 and n is >0 and one of and $Q_0$ or $Q_1$ is a residue which is hydrophilic and at least partially cationic at physiologic pH and the other of $Q_0$ or $Q_1$ is a residue which is hydrophilic and is substantially neutral at physiologic pH. In certain embodiments, m is >0 and n is >0 and one of and $Q_0$ or $Q_1$ is a residue which is hydrophilic and at least partially anionic at physiologic pH and the other of $Q_0$ or $Q_1$ is a residue which is hydrophilic and is substantially neutral at physiologic pH. In certain embodiments, m is >0 and n is >0 and $Q_1$ is a residue which is hydrophilic and at least partially cationic at physiologic pH and $Q_0$ is a residue which is a conjugatable or functionalizable residue. In certain embodiments, m is >0 and n is >0 and $Q_1$ is a residue which is hydrophilic and substantially neutral at physiologic pH and $Q_0$ is a residue which is a conjugatable or functionalizable residue.

In some embodiments, the positively charged or at least partially positively charged at physiologic pH group is a —NR'R" group, wherein R' and R" are independently selected from hydrogen, alkyl, cycloalkyl, or heteroalkyl which may be optionally substituted with one or more halogen, amino, hydroxyl groups and/or comprise one or more unsaturated bonds; in some embodiments, R' and R' are taken together to form a substituted of unsubstituted heteroaryl or alicyclic heterocycle. In some embodiments, groups described herein as positively charged or at least partially positively charged at physiologic pH may include, by way of non-limiting example, amino, alkyl amino, dialkyl amino, cyclic amino (e.g., piperidine or N-alkylated piperidine), alicyclic imino (e.g., dihydro-pyridinyl, 2,3,4,5-tetrahydro-pyridinyl, or the like), heteroaryl imino (e.g., pyridinyl), or the like. In some embodiments, groups described herein as negatively charged or at least partially negatively charged at physiologic pH but undergoes protonation at lower pH, such as, by way of non-limiting example, carboxylic acid (COOH), sulfonamide, boronic acid, sulfonic acid, sulfinic acid, sulfuric acid, phosphoric acid, phosphinic acid, phosphorous acid, carbonic acid, the deprotonated conjugate base thereof, or the like.

In certain embodiments, provided herein is a compound of Formula II:

(II)

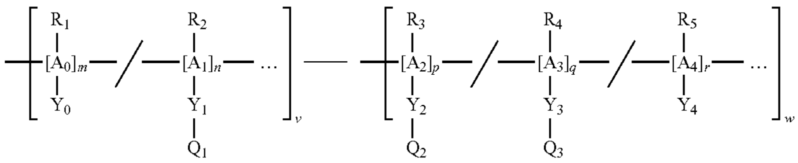

In some embodiments:

$A_0$, $A_1$, $A_2$, $A_3$ and $A_4$ are selected from the group consisting of —C—C—, —C(O)(C)$_a$C(O)O—, —O(C)$_a$C(O)— and —O(C)$_b$O—; wherein, a is 1-4;

b is 2-4;

$Y_0$ and $Y_4$ are independently selected from the group consisting of hydrogen, (1C-10C)alkyl, (3C-6C)cycloalkyl, O-(1C-10C)alkyl, —C(O)O(1C-10C)alkyl, C(O)NR$_6$(1C-10C) and aryl, any of which is optionally substituted with one or more fluorine groups;

$Y_1$ and $Y_2$ are independently selected from the group consisting of a covalent bond, (1C-10C)alkyl-, —C(O)O(2C-10C) alkyl-, —OC(O)(1C-10C) alkyl-, —O(2C-10C)alkyl- and —S(2C-10C)alkyl- —C(O)NR$_6$(2C-10C) alkyl;

$Y_3$ is selected from the group consisting of a covalent bond, (1C-10C)alkyl and (6C-10C)aryl; wherein tetravalent carbon atoms of $A_1$-$A_4$ that are not fully substituted with $R_1$-$R_5$ and $Y_0$-$Y_4$ are completed with an appropriate number of hydrogen atoms;

$R_1$, $R_2$, $R_3$, $R_4$, $R_5$, and $R_6$ are independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;

$Q_1$ and $Q_2$ are residues which are positively charged at physiologic pH, including but not limited to amino, alkylamino, ammonium, alkylammonium, guanidine, imidazolyl, and pyridyl.

$Q_3$ is a residue which is negatively charged at physiologic pH, but undergoes protonation at lower pH, including but not limited to carboxyl, sulfonamide, boronate, phosphonate, and phosphate.

m is 0 to about 0.49;

n is about 0.51 to about 1.0; wherein $$m+n=1$$

p is about 0.2 to about 0.5;

q is about 0.2 to about 0.5; wherein:

p is substantially the same as q;

r is 0 to about 0.6; wherein $$p+q+r=1$$

v is from about 1 to about 25 kDa, or about 5 to about 25 kDa; and, w is from about 1 to about 50 kDa, or about 5 to about 50 kDa.

In certain embodiments, the block copolymer is a diblock copolymer, having the chemical formula (at normal physiological or about neutral pH) of Formula III:

(III)

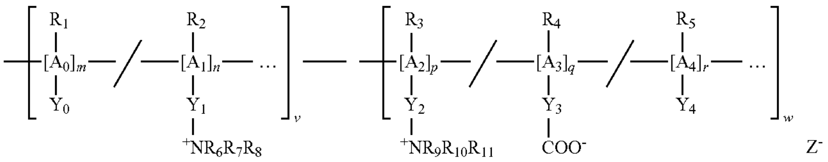

In certain embodiments, $A_0$, $A_1$, $A_2$, $A_3$, and $A_4$, substituted as indicated comprise the constitutional units (used interchangeably herein with "monomeric units" and "monomeric residues") of the polymer of Formula III. In specific embodiments, the monomeric units of constituting the A groups of Formula III are polymerizably compatible under appropriate conditions. In certain instances, an ethylenic backbone or constitutional unit, —(C—C—)$_m$— polymer, wherein each C is di-substituted with H and/or any other suitable group, is polymerized using monomers containing a carbon-carbon double bond, >C═C<. In certain embodiments, each A group (e.g., each of $A_0$, $A_1$, $A_2$, $A_3$, and $A_4$) may be (i.e., independently selected from) —C—C— (i.e., an ethylenic monomeric unit or polymer backbone), —C(O)(C)$_a$C(O)O— (i.e., a polyanhydride monomeric unit or polymer backbone), —O(C)$_a$C(O)— (i.e., a polyester monomeric unit or polymer backbone), —O(C)$_b$O— (i.e., a polyalkylene glycol monomeric unit or polymer backbone), or the like (wherein each C is di-substituted with H and/or any other suitable group such as described herein, including $R_{12}$ and/or $R_{13}$ as described above). In specific embodiments, the term "a" is an integer from 1 to 4, and "b" is an integer from 2 to 4. In certain instances, each "Y" and "R" group attached to the backbone of Formula III (i.e., any one of $Y_0$, $Y_1$, $Y_2$, $Y_3$, $Y_4$, $R_1$, $R_2$, $R_3$, $R_4$, $R_5$) is bonded to any "C" (including any (C)$_a$ or (C)$_b$) of the specific monomeric unit. In specific embodiments, both the Y and R of a specific monomeric unit is attached to the same "C". In certain specific embodiments, both the Y and R of a specific monomeric unit is attached to the same "C", the "C" being alpha to the carbonyl group of the monomeric unit, if present.

In specific embodiments, $R_1$-$R_{11}$ are independently selected from hydrogen, alkyl (e.g., 1C-5C alkyl), cycloalkyl (e.g., 3C-6C cycloalkyl), or phenyl, wherein any of $R_1$-$R_{11}$ is optionally substituted with one or more fluorine, cycloalkyl, or phenyl, which may optionally be further substituted with one or more alkyl group.

In certain specific embodiments, $Y_0$ and $Y_4$ are independently selected from hydrogen, alkyl (e.g., 1C-10C alkyl), cycloalkyl (e.g., 3C-6C cycloalkyl), O-alkyl (e.g., 0(2C-10C)alkyl, —C(O)O-alkyl (e.g., —C(O)O-(2C-10C)alkyl), or phenyl, any of which is optionally substituted with one or more fluorine.

In some embodiments, $Y_1$ and $Y_2$ are independently selected from a covalent bond, alkyl, preferably at present a (1C-10C)alkyl, —C(O)O-alkyl, preferably at present —C(O)O-(2C-10C)alkyl, —OC(O)alkyl, preferably at present —OC(O)-(2C-10C)alkyl, O-alkyl, preferably at present —O(2C-10C)alkyl and —S-alkyl, preferably at present —S-(2C-10C)alkyl. In certain embodiments, $Y_3$ is selected from a covalent bond, alkyl, preferably at present (1C-5C)alkyl and phenyl.

In some embodiments, Z— is present or absent. In certain embodiments, wherein $R_1$ and/or $R_4$ is hydrogen, Z— is OH—. In certain embodiments, $Z^-$ is any counterion (e.g., one or more counterion), preferably a biocompatible counter ion, such as, by way of non-limiting example, chloride, inorganic or organic phosphate, sulfate, sulfonate, acetate, propionate, butyrate, valerate, caproate, caprylate, caprate, laurate, myristate, palmate, stearate, palmitolate, oleate, linolate, arachidate, gadoleate, vaccinate, lactate, glycolate, salicylate, desamionphenylalanine, desaminoserine, desaminothreonine, ϵ-hydroxycaproate, 3-hydroxybutylrate, 4-hydroxybutyrate or 3-hydroxyvalerate. In some embodiments, when each Y, R and optional fluorine is covalently bonded to a carbon of the selected backbone, any carbons that are not fully substituted are completed with the appropriate number of hydrogen atoms. The numbers m, n, p, q and r represent the mole fraction of each constitutional unit in its block and v and w provide the molecular weight of each block.

In certain embodiments, $A_0$, $A_1$, $A_2$, $A_3$ and $A_4$ are selected from the group consisting of —C—, —C—C—, —C(O)$(CR_{12}R_{13})_a$C(O)O—, —O$(CR_{12}R_{13})_a$C(O)— and O$(CR_{12}R_{13})_b$O; wherein,
 a is 1-4;
 b is 2-4;

$R_1$, $R_2$, $R_3$, $R_4$, $R_5$, $R_6$, $R_7$. $R_8$, $R_9$, $R_{10}$, $R_{11}$, $R_{12}$, and $R_{13}$ are independently selected from the group consisting of hydrogen, (1C-5C)alkyl, (3C-6C)cycloalkyl, (5C-10C) aryl, (4C-10C)heteroaryl, any of which may be optionally substituted with one or more fluorine atoms;

$Y_0$ and $Y_4$ are independently selected from the group consisting of hydrogen, (1C-10C)alkyl, (3C-6C)cycloalkyl, 0-(1C-10C)alkyl, —C(O)O(1C-10C)alkyl and phenyl, any of which is optionally substituted with one or more fluorine groups;

$Y_1$ and $Y_2$ are independently selected from the group consisting of a covalent bond, (1C-10C)alkyl-, —C(O)O(2C-10C) alkyl-, —OC(O)(1C-10C) alkyl-, —O(2C-10C)alkyl- and —S(2C-10C)alkyl-;

$Y_3$ is selected from the group consisting of a covalent bond, (1C-5C)alkyl and phenyl;

wherein tetravalent carbon atoms of $A_1$-$A_4$ that are not fully substituted with $R_1$-$R_5$ and $Y_0$-$Y_4$ are completed with an appropriate number of hydrogen atoms;

Z is one or more physiologically acceptable counterions, m is 0 to about 0.49;

n is about 0.51 to about 1.0; wherein $$m+n=1$$

p is about 0.2 to about 0.5;

q is about 0.2 to about 0.5; wherein:
 p is substantially the same as q;

r is 0 to about 0.6; wherein $$p+q+r=1$$

v is from about 1 to about 25 kDa, or about 5 to about 25 kDa; and, w is from about 1 to about 50 kDa, or about 5 to about 50 kDa.

In a specific embodiment, $A_0$, $A_1$, $A_2$, $A_3$ and $A_4$ are independently selected from the group consisting of —C—C—, —C(O)$(C)_a$C(O)O—, —O$(C)_a$C(O)— and —O$(C)_b$O—; wherein,
 a is 1-4;
 b is 2-4;

$R_1$, $R_2$, $R_3$, $R_4$, $R_5$, $R_6$, $R_7$, $R_8$, $R_9$, $R_{10}$ and $R_{11}$ are independently selected from the group consisting of hydrogen, (1C-5C)alkyl, (3C-6C)cycloalkyl and phenyl, any of which may be optionally substituted with one or more fluorine atoms;

$Y_0$ and $Y_4$ are independently selected from the group consisting of hydrogen, (1C-10C)alkyl, (3C-6C)cycloalkyl, O-(1C-10C)alkyl, —C(O)O(1C-10C)alkyl and phenyl, any of which is optionally substituted with one or more fluorine groups;

$Y_1$ and $Y_2$ are independently selected from the group consisting of a covalent bond, (1C-10C)alkyl-, —C(O)O(2C-10C) alkyl-, —OC(O)(1C-10C) alkyl-, —O(2C-10C)alkyl- and —S(2C-10C)alkyl-;

$Y_3$ is selected from the group consisting of a covalent bond, (1C-5C)alkyl and phenyl;

wherein tetravalent carbon atoms of $A_1$-$A_4$ that are not fully substituted with $R_1$-$R_5$ and $Y_0$-$Y_4$ are completed with an appropriate number of hydrogen atoms;

Z is a physiologically acceptable counterion, m is 0 to about 0.49;

n is about 0.51 to about 1.0;

wherein $m+n=1$ p is about 0.2 to about 0.5;

q is about 0.2 to about 0.5; wherein:
 p is substantially the same as q;

r is 0 to about 0.6; wherein $$p+q+r=1$$

v is from about 5 to about 25 kDa; and w is from about 5 to about 25 kDa.

In some embodiments, $A_1$ is —C—C—

$Y_1$ is —C(O)$OCH_2CH_2$—;

$R_6$ is hydrogen;

$R_7$ and $R_8$ are each —$CH_3$; and, $R_2$ is —$CH_3$.

In some embodiments, $A_2$ is —C—C—;

$Y_2$ is —C(O)$OCH_2CH_2$—;

$R_9$ is hydrogen;

$R_{10}$ and $R_{11}$ are each —$CH_3$; and, $R_3$ is —$CH_3$.

In some embodiments, $A_3$ is —C—C—;

$R_4$ is $CH_3CH_2CH_2$—;

$Y_3$ is a covalent bond;

and $Z^-$ is a physiologically acceptable anion.

In some embodiments, $A_4$ is —C—C—;

$R_5$ is selected from the group consisting of hydrogen and —$CH_3$; and, $Y_4$ is —$C(O)O(CH_2)_3CH_3$.

In some embodiments, $A_0$ is C—C—

$R_1$ is selected from the group consisting of hydrogen and (1C-3C)alkyl; and, $Y_0$ is selected from the group consisting of —C(O)O(1C-3C)alkyl.

In some embodiments, m is 0.

In some embodiments, r is 0.

In some embodiments, m and r are both 0.

Provided in some embodiments, is an exemplary but non-limiting polymer of this invention:

IV1

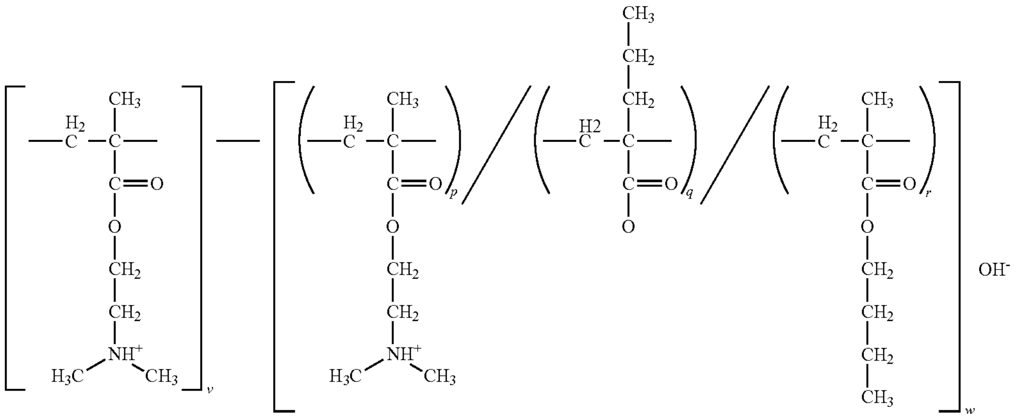

In certain instances, the constitutional units of compound 1 are as shown within the square bracket on the left and the curved brackets on the right and they are derived from the monomers:

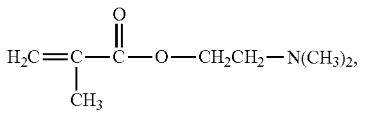

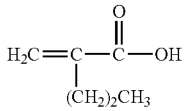

and

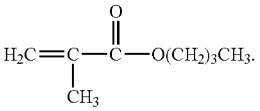

The letters p, q and r represent the mole fraction of each constitutional unit within its block. The letters v and w represent the molecular weight (number average) of each block in the diblock copolymer.

Provided in some embodiments, a compound provided herein is a compound having the structure:

IV2

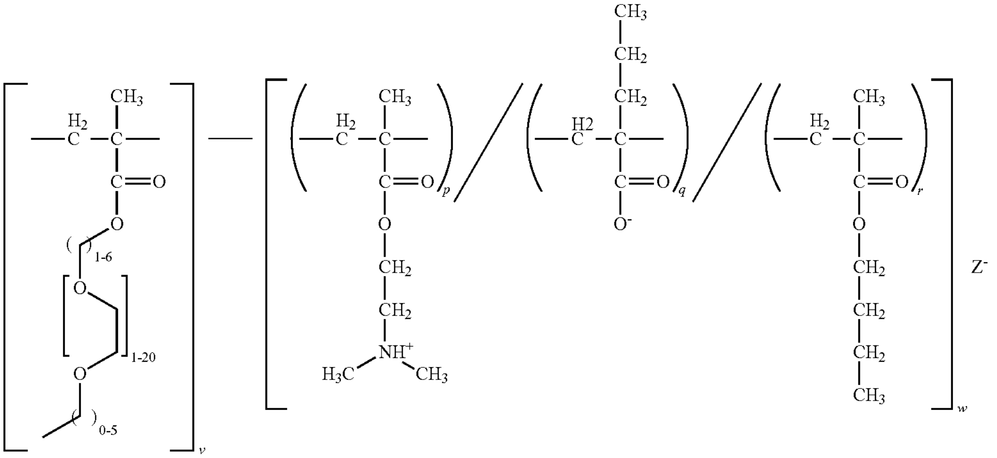

As discussed above, letters p, q and r represent the mole fraction of each constitutional unit within its block. The letters v and w represent the molecular weight (number average) of each block in the diblock copolymer.

In some embodiments, provided herein the following polymers:

$[DMAEMA]_v$-$[B_r$-/-$P_q$-/-$D_p]_w$ IV3

$[PEGMA]_v$-$[B_r$-/-$P_q$-/-$D_p]_w$ IV4

$[PEGMA_m$-/-$DMAEMA_n]_v$-$[B_r$-/-$P_q$-/-$D_p]_w$ IV5

$[PEGMA_m$-/-MAA(NHS)$_n]_v$-$[B_r$-/-$P_q$-/-$D_p]_w$ IV6

$[DMAEMA_m$-/-MAA(NHS)$_n]_v$-$[B_r$-/-$P_q$-/-$D_p]_w$ IV7

$[HPMA_m$-/-$PDSM_n]_v$-$[B_r$-/-$P_q$-/-$D_p]_w$ IV8

$[PEGMA_m$-/-$PDSM_n]_v$-$[B_r$-/-$P_q$-/-$D_p]_w$ IV9

In some embodiments, B is butyl methacrylate residue; P is propyl acrylic acid residue; D and DMAEMA are dimethylaminoethyl methacrylate residue; PEGMA is polyethyleneglycol methacrylate residue (e.g., with 1-20 ethylene oxide units, such as illustrated in compound IV-2, or 4-5 ethylene oxide units, or 7-8 ethylene oxide units); MAA (NHS) is methylacrylic acid-N-hydroxy succinimide residue; HPMA is N-(2-hydroxypropyl)methacrylamide residue; and PDSM is pyridyl disulfide methacrylate residue. In certain embodiments, the terms m, n, p, q, r, w and v are as described herein. In specific embodiments, w is about 0.1 times to about 5 times v, or about 1 times to about 5 times v.

Polymers IV1-IV9 are examples of polymers provided herein comprising a variety of constitutional unit(s) making up the first block of the polymer. Moreover, polymers set forth in the Figures and Table, as well as structurally related polymers (such as variations in MW and/or monomeric residue ratios) are specifically provided for herein. In some embodiments, the constitutional unit(s) of the first block are varied or chemically treated in order to create polymers where the first block is or comprises a constitutional unit that is neutral (e.g., PEGMA), cationic (e.g., DMAEMA), anionic (e.g., PEGMA-NHS, where the NHS is hydrolyzed to the acid, or acrylic acid), ampholytic (e.g., DMAEMA-NHS, where the NHS is hydrolyzed to the acid), or zwiterrionic (for example, poly[2-methacryloyloxy-2' trimethylammoniumethyl phosphate]). In some embodiments, polymers comprising pyridyl disulfide functionality in the first block, e.g., [PEGMA-PDSM]-[B-P-D], that can be and is optionally reacted with a thiolated siRNA to form a polymer-siRNA conjugate.

In some embodiments, the polymers of this invention are "diblock copolymers." The term "copolymer" signifies that the polymer is the result of polymerization of two or more different monomers. In some instances, a "block" copolymer refers to a structure in which distinct sub-combinations of constitutional units are joined together. In certain instances, a "block" refers to a segment or portion of a polymer having a particular characteristics (e.g., a hydrophilic segment or a hydrophobic segment of a gradient copolymer). In some instances, a diblock copolymer comprises just two blocks; a schematic generalization of such a polymer would look like: $[A_aB_bC_c \ldots]_m$-$[X_xY_yZ_z \ldots]_n$ wherein each letter stands for a constitutional unit, each subscript to a constitutional unit represents the mole fraction of that unit in the particular block, the three dots indicate that there may be more (but of course there may also be fewer) constitutional units in each block and m and n indicate the molecular weight of each block in the diblock copolymer. As suggested by the schematic, the number and the nature of each constitutional unit is separately controlled for each block. It is understood that the schematic is not meant and should not be construed to infer any relationship whatsoever between the number of constitutional units or the number of different types of constitutional units in each of the blocks. Nor is the schematic meant to describe any particular arrangement of the constitutional units within a particular block. That is, in each block the constitutional units may be disposed in a purely random, an alternating random, a regular alternating, a regular block or a random block configuration unless expressly stated to be otherwise. A purely random configuration would, for example, be: x-x-y-z-x-y-y-z-y-z-z-z . . . or y-z-x-y-z-y-z-x-x . . . . An alternating random configuration would be: x-y-x-z-y-x-y-z-y-x-z . . . , and a regular alternating configuration would be: x-y-z-x-y-z-x-y-z . . . . A regular block configuration has the following general configuration: . . . x-x-x-y-y-y-z-z-z-x-x-x . . . , while a random block configuration has the general configuration; . . . x-x-x-z-z-x-x-y-y-y-y-z-z-z-x-x-z-z-z- . . . . In none of the preceding generic examples is the particular juxtaposition of individual constitutional units or blocks or the number of constitutional units in a block or the number of blocks meant nor should they be construed as in any manner bearing on or limiting the actual structure of diblock copolymers of this invention.

It is further understood that the curved brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. Thus in diblock copolymer 1, p, q and r represent the mole fraction of that constitutional unit in the block and is not intended, and must not be construed, as indicating or suggesting that the constitutional units within the brackets comprise a block within a block.

Thus, when it is stated herein that a charge neutral constitutional unit may be "randomly interspersed" among the first constitutional units of the first block of a diblock copolymer of this invention, it means that the first block would have a structure generically akin to that described above for a purely random configuration.

In some embodiments, the solubility of any of the block copolymers described herein in aqueous solution or medium at about neutral pH is more than 1 mg/mL, more than 5 mg/mL, more than 10 mg/mL, more than 25 mg/mL, more than 50 mg/mL, more than 100 mg/mL and more than 500 mg/mL. In some embodiments, in particular for diblock polymers having a hydrophilic (e.g., a cationic hydrophilic) first block, the three species present in the hydrophobic block (anionic, cationic and hydrophobic) are present as a random copolymer block, or are otherwise present in an interspersed sequence such that the block is of approximately net neutral charge across its length. In some instances, this orientation provides increased solubility of the block copolymer.

In certain embodiments, the diblock copolymers set forth in Table 1 are provided herein; in certain instances, such polymers are used as polynucleotide complexing agents and carriers. It is understood that the characteristics of diblock copolymers described in Table 1 and otherwise herein will be translatable to other diblock copolymers hereof such that, based on the disclosures herein, those skilled in the art will be capable of preparing such copolymers, which will therefore be within the scope of this invention.

The first block of exemplary diblock copolymers are composed of monomeric residues of dimethylaminoethylmethacrylate (DMAEMA), which efficiently binds to and condenses nucleic acids at physiological pH. The second block of an exemplary polymer described herein contained monomeric residues of DMAEMA as a cationic constitutional unit; monomeric residues of propyl acrylic acid (PAA) as an anionic constitutional unit and, due to the hydrophobic propyl substituent, a contributor to the hydrophobicity enhancing moiety; and monomeric residues of butyl methylacrylate (BMA) as a separate constitutional unit, constituting or comprising a hydrophobicity enhancing moiety. In certain instances, the second block enables endosomal escape of the bound nucleic acid through a pH-induced conformational change which, in some instances, results in membrane destabilization. In some instances, under physiological conditions, the second or hydrophobic core block has both positive (e.g., protonated DMAEMA) residues and negative (e.g., de-protonated PAA) residues in similar amounts, resulting in approximate charge neutrality and charge stabilization of the core by the formation of ion pairs. In certain instances, upon uptake of a polymer-nucleic acid composition described herein into endosomal compartments of the cell, the lower pH of the endosomal environment causes anionic residues of the third constitutional unit (e.g., PAA carboxylate groups) to become protonated and thereby membrane disruptive. In some instances, protonation or neutralization some or all of the anionic residues results in charge neutralization of the PAA acidic residues and, in certain instances, in a conformational change in the polymer to a hydrophobic membrane-destabilizing form.

Poly(DMAEMA) and other polymeric entities used herein (e.g., copolymers or copolymer blocks of BMA, DMAEMA and PAA) are prepared in any suitable manner. In one instance, poly(DMAEMA) was prepared by polymerizing DMAEMA in the presence of the RAFT CTA, ECT, and a radical initiator. In some instances, a block, poly (DMAEMA) (9,100 g/mol; DP 58), was used to prepare a series of diblock copolymers where the BMA content was increased and equimolar quantities of DMAEMA and PAA were maintained. Characteristics of the resulting polymers are shown in Table 1. Similar block sizes were observed for all seven diblocks giving the polymers an overall molecular weight of around 20,000 g/mol. In certain embodiments, lower molecular weights are chosen. In some instances, lower molecular weight polymers minimize polymer toxicity and enable renal clearance of the polymers in order to ensure amenable translation to in vivo testing. Also shown in Table 1 are the theoretical and experimentally derived monomer compositions of the second block. Each polymer listed is an example of a class of related polymers. For example, polymers of the P7 class have several versions, one of which is characterized in Table 1. While all polymers are relatively close to the theoretical composition, some deviation is observed in all cases and is likely due to differences in the monomer reactivity ratios.

Alternatively, the orientation of the blocks on the diblock polymer is reversed, such that the ω end of the polymer is the hydrophilic block. In various embodiments, this is achieved in any suitable manner, including a number of ways synthetically. For example, the synthesis of the block copolymers of the present invention begins with the preparation of the PAA/BMA/DMAEMA hydrophobic block, and the hydrophilic, charged block is added in the second synthetic step either by subjecting the resulting PAA/BMA/DMAEMA macroCTA to a second RAFT polymerization step. Alternate approaches include reducing the PAA/BMA/DMAEMA macroCTA to form a thiol end and then covalently attaching a pre-formed hydrophilic, charged polymer to the formed thiol. This synthetic approach provides a method for introduction of a reactive group on the ω-end of the hydrophilic end of the polymeric chain thus providing alternate approaches to chemical conjugation to the polymer.

The diblock copolymer P7, one example of a polymer of the present invention, consists of two blocks; one is poly (DMAEMA), which is hydrophilic and charged at physiological pH, and the other block is a random copolymer of monomer units: hydrophobic (BMA) and ionized/hydrophobic or ionizable/hydrophobic units (PAA, DMAEMA).

TABLE 1

Molecular weights, polydispersities, and monomer compositions for the poly(DMAEMA) macroCTA, the resultant diblock copolymers and their corresponding nomenclature.

| Polymer | $M_n$[a] 1st block (g/mol) | $M_n$[a] 2nd block (g/mol) | PDI[a] | Theoretical % BMA $2^{nd}$ block | Theoretical % PAA $2^{nd}$ block | Theoretical % DMAEMA $2^{nd}$ block | Experimental[b] % BMA $2^{nd}$ block | Experimental[b] % PAA $2^{nd}$ block | Experimental[b] % DMAEMA $2^{nd}$ block |
|---|---|---|---|---|---|---|---|---|---|
| mCTA | 9 100 | — | 1.16 | — | — | — | — | — | — |
| P1 | 9 100 | 6 900 | 1.58 | 0 | 50 | 50 | — | 47 | 53 |
| P2 | 9 100 | 8 900 | 1.56 | 5 | 47.5 | 47.5 | 1 | 48 | 51 |
| P3 | 9 100 | 8 300 | 1.54 | 10 | 45 | 45 | 12 | 40 | 48 |
| P4 | 9 100 | 9 300 | 1.46 | 15 | 42.5 | 42.5 | 19 | 44 | 37 |
| P5 | 9 100 | 10 100 | 1.51 | 20 | 40 | 40 | 24 | 40 | 36 |
| P6 | 9 100 | 10 000 | 1.48 | 30 | 35 | 35 | 27 | 37 | 36 |
| P7 | 9 100 | 11 300 | 1.45 | 40 | 30 | 30 | 48 | 29 | 23 |

[a]As determined by SEC Tosoh TSK-GEL R-3000 and R-4000 columns (Tosoh Bioscience, Mongomeryville, PA) connected in series to a Viscotek GPCmax VE2001 and refractometer VE3580 (Viscotek, Houston, TX). HPLC-grade DMF containing 0.1 wt % LiBr was used as the mobile phase. The molecular weights of the synthesized copolymers were determined using a series of poly(methyl methacrylate) standards.
[b]As determined by $^1H$ NMR spectroscopy (3 wt % in $CDCL_3$; Bruker DRX 499)

DEFINITIONS AND EMBODIMENTS

It is understood that, with regard to this application, use of the singular includes the plural and vice versa unless expressly stated to be otherwise. That is, “a” and “the” refer to one or more of whatever the word modifies. For example, “the polymer” or “a nucleotide” may refer to one polymer or nucleotide or to a plurality of polymers or nucleotides. By the same token, “polymers” and “nucleotides” would refer to one polymer or one nucleotide as well as to a plurality of polymers or nucleotides unless, again, it is expressly stated or obvious from the context that such is not intended, A used herein, words of approximation such as, without limitation, "about" "substantially," "essentially" and "approximately" mean that the element of limitation so modified need not be exactly that which is written but may vary from that written description to some extent. The extent to which the description may vary will depend on how great a change one of ordinary skill in the art would accept and still consider the element to have the characteristics and capabilities of that element or limitation. In general, but subject to the preceding discussion, a numerical value herein that is modified by a word of approximation may vary from the stated value by at least ±15%, about ±15%, about ±10%, about ±5%, about ±3%, about ±2%, or about ±1%. As a specific non-limiting example from this invention, the second block of a diblock copolymer of this invention, which contains both cationic and anionic species at normal physiological pH, is described as being "substantially neutral in overall charge" and substantially hydrophobic. Experimentally, however, it is extremely difficult to achieve exact neutrality and either the cationic or the anionic species may predominate to some extent as illustrated in Table 1. One of ordinary skill in the art would, however, accept a second block with a slight excess of one or the other charged species as still being "substantially neutral."

As used herein, a "polymer" refers to a molecule composed of one or more smaller molecules called "monomers." A monomer may react with itself to create a homopolymer or it may react with one or more other monomers to create copolymers. Groups of monomers may be reacted to form "prepolymers," which are then combined to form the polymer. The monomers comprise the "constitutional units" of the polymer.

A "charge neutral" or "non-charged" constitutional unit refers to one in which no atom bears a full positive or negative charge at physiological pH, that is, dipolar molecules are still considered "charge neutral" or "non-charged". An non-limiting example of a charge neutral constitutional unit would be that derived from butyl methacrylate, $CH_2{=}C(CH_3)C(O)O(CH_2)_3CH_3$ monomer.

As used herein, "alkyl" refers to a straight or branched chain fully saturated (no double or triple bonds) hydrocarbon (carbon and hydrogen only) group. Examples of alkyl groups include, but are not limited to, methyl, ethyl, propyl, isopropyl, butyl, isobutyl, sec-butyl, tertiary butyl, pentyl and hexyl. As used herein, "alkyl" includes "alkylene" groups, which refer to straight or branched fully saturated hydrocarbon groups having two rather than one open valences for bonding to other groups. Examples of alkylene groups include, but are not limited to methylene, $—CH_2—$, ethylene, $—CH_2CH_2—$, propylene, $—CH_2CH_2CH_2—$, n-butylene, $—CH_2CH_2CH_2CH_2—$, sec-butylene, $—CH_2CH_2CH(CH_3)—$ and the like. An alkyl group of this invention may optionally be substituted with one or more fluorine groups.

As used herein, "mC to nC," wherein m and n are integers refers to the number of possible carbon atoms in the indicated group. That is, the group can contain from "m" to "n", inclusive, carbon atoms. An alkyl group of this invention may comprise from 1 to 10 carbon atoms, that is, m is 1 and n is 10. Of course, a particular alkyl group may be more limited. For instance without limitation, an alkyl group of this invention may consist of 3 to 8 carbon atoms, in which case it would be designated as a (3C-8C)alkyl group. The numbers are inclusive and incorporate all straight or branched chain structures having the indicated number of carbon atoms. For example without limitation, a "$C_1$ to $C_4$ alkyl" group refers to all alkyl groups having from 1 to 4 carbons, that is, $CH_3—$, $CH_3CH_2—$, $CH_3CH_2CH_2—$, $CH_3CH(CH_3)—$, $CH_3CH_2CH_2CH_2—$, $CH_3CH_2CH(CH_3)—$, $(CH_3)_2CHCH_2—$ and $(CH_3)_3CH—$.

As use herein, a cycloalkyl group refers to an alkyl group in which the end carbon atoms of the alkyl chain are covalently bonded to one another. The numbers "m" and "n" refer to the number of carbon atoms in the ring formed. Thus for instance, a (3C-8C) cycloalkyl group refers to a three, four, five, six, seven or eight member ring, that is, cyclopropane, cyclobutane, cyclopentane, cyclohexane, cycloheptane and cyclooctane. A cycloalkyl group of this invention may optionally be substituted with one or more fluorine groups and/or one or more alkyl groups.

As used herein, "phenyl" simply refers to a

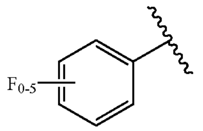

group which, as shown, can optionally be substituted with one or more fluorine groups.

As used herein, a "hydrophobicity-enhancing moiety" is used interchangeably herein with a "hydrophobic species" and refers to a substituent covalently bonded to a constitutional unit of a diblock copolymer, with such constitutional units bearing said hydrophobicity-enhancing moieties resulting in the diblock copolymer becoming more membrane disruptive or otherwise more membrane destabilizing than it would be without the addition of the moiety. Examples of such moieties include, without limitation, alkyl groups, cycloalkyl groups and phenyl groups, any of which may be substituted with one or more fluorine atoms. In some embodiments, a hydrophobicity-enhancing moiety has a $\pi$ value of about one, or more. A compound's $\pi$ value is a measure of its relative hydrophilic-lipophilic value (see, e.g., Cates, L. A., "Calculation of Drug Solubilities by Pharmacy Students" *Am. J. Pharm. Educ.* 45:11-13 (1981)). Hydrophobic monomeric residues or constitutional units described herein comprise one or more hydrophobic species. Moreover, hydrophilic monomeric residues comprise one or more hydrophilic species.

With regard to the non-limiting exemplary polymer of this invention IV1 shown above, such a polymer would be characterized as being "ethylenic" in that the constitutional units are derived from the reaction of an ethylene, $—C{=}C—$, functionality of each of the monomers. The particular ethylenic monomers of the above example may be further described as being "acrylic" in that they are all derivatives of acrylic acid, $CH_2{=}CHC(O)OH$, the first monomer above being dimethylaminoethyl methacrylate, the second being 2-propylacrylic acid and the third being butyl methacrylate.

As used herein, "normal physiological pH" refers to the pH of the predominant fluids of the mammalian body such as blood, serum, the cytosol of normal cells, etc. Moreover, as used herein, "normal physiological pH", used interchangeably with "about physiologic pH" or "about neutral pH", generally refers to an about neutral pH (i.e., about pH 7), including, e.g., a pH that is about 7.2 to about 7.4. In specific instances, a "normal physiological pH" refers to a pH that is about neutral in an aqueous medium, such as blood, serum, or the like.

As used herein, RNA refers to a polynucleotide comprising A, C, G or U nucleotides and DNA refers to a polynucleotide comprising dA, dC, dG and dT, the "d" indicating that the sugar is deoxyribose.

As used herein, a "natural DNA analog" or a "natural RNA analog" a polynucleotide in which one or more naturally-occurring nucleotides are substituted for the natural nucleotides of a particular DNA or RNA but which still exhibits the functionality of the original DNA or RNA. This includes a naturally-occurring nucleotide in a non-natural environment, e.g., a ribonucleotide substituted for a deoxyribonucleotide in a DNA molecule or a deoxyribonucleotides substituted for a ribonucleotide in an RNA molecule.

As used herein, a "synthetic DNA analog" or a "synthetic RNA analog" refers to a polynucleotide comprised of one or more modified nucleotides. A "modified nucleotide" refers to a non-naturally occurring nucleotide that comprises a chemically altered base, sugar and/or phosphodiester linkage. Chemical alteration may involve addition, deletion or substitution of individual atoms of a naturally-occurring nucleotide or the addition, deletion of substitution of entire functional groups of the nucleotide. For the purposes of this invention a modified nucleotide may indeed comprise a molecule that resembles a natural nucleotide little, if at all, but is nevertheless capable of being incorporated into a polynucleotide having the generic structure described above. One property of a synthetic DNA or RNA analog that is typically maintained is that the molecule is generally negatively charged as are all natural polynucleotides so that it can complex with a diblock copolymer of this invention.

Without being bound by theory not expressly recited in the claims, a membrane destabilizing polymer can directly or indirectly elicit a change (e.g., a permeability change) in a cellular membrane structure (e.g., an endosomal membrane) so as to permit an agent (e.g., polynucleotide), in association with or independent of a polymer, to pass through such membrane structure—for example to enter a cell or to exit a cellular vesicle (e.g., an endosome). A membrane destabilizing polymer can be (but is not necessarily) a membrane disruptive polymer. A membrane disruptive polymer can directly or indirectly elicit lysis of a cellular vesicle or disruption of a cellular membrane (e.g., as observed for a substantial fraction of a population of cellular membranes).

Generally, membrane destabilizing or membrane disruptive properties of polymers can be assessed by various means. In one non-limiting approach, a change in a cellular membrane structure can be observed by assessment in assays that measure (directly or indirectly) release of an agent (e.g., polynucleotide) from cellular membranes (e.g., endosomal membranes)—for example, by determining the presence or absence of such agent, or an activity of such agent, in an environment external to such membrane. Another non-limiting approach involves measuring red blood cell lysis (hemolysis)—e.g., as a surrogate assay for a cellular membrane of interest. Such assays may be done at a single pH value or over a range of pH values.

It is preferred that a diblock copolymer provided herein is biocompatible. As used herein, "biocompatible" refers to a property of a polymer characterized by it, or its in vivo degradation products, being not, or at least minimally and/or reparably, injurious to living tissue; and/or not, or at least minimally and controllably, causing an immunological reaction in living tissue. With regard to salts, it is presently preferred that both the cationic and the anionic species be biocompatible. As used herein, "physiologically acceptable" is interchangeable with biocompatible.

In certain aspects, the compositions and/or agents described herein are used as in vivo therapeutic agents. By "in vivo" is meant that they are intended to be administered to subjects in need of such therapy. "Subjects" refers to any living entity that might benefit from treatment using the complexes of this invention. As used herein "subject" and "patient" may be used interchangeably. A subject or patient refers in particular to a mammal such as, without limitation, cat, dog, horse, cow, sheep, rabbit, etc., and preferably at present, a human being.

As used herein, "therapeutic agent" refers to a complex hereof that, when administered in a therapeutically effective amount to a subject suffering from a disease, has a therapeutic beneficial effect on the health and well-being of the subject. A therapeutic beneficial effect on the health and well-being of a subject includes, but is not limited to: (1) curing the disease; (2) slowing the progress of the disease; (3) causing the disease to retrogress; or, (4) alleviating one or more symptoms of the disease. As used herein, a therapeutic agent also includes any complex herein that when administered to a patient, known or suspected of being particularly susceptible to a disease in particular at present a genetic disease, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of the complex; or, (3) preventing or delaying recurrence of the disease after a course of treatment with a therapeutically effective amount of the complex has concluded. In some instances, a therapeutic agent is a therapeutically effective polynucleotide (e.g., an RNAi polynucleotide), a therapeutically effective peptide, a therapeutically effective polypeptide, or some other therapeutically effective biomolecule. In specific embodiments, an RNAi polynucleotide is an polynucleotide which can mediate inhibition of gene expression through an RNAi mechanism and includes but is not limited to messenger RNA (mRNA), siRNA, microRNA (miRNA), short hairpin RNA (shRNA), asymmetrical interfering RNA (aiRNA), dicer substrate and the precursors thereof.

As used herein, "living polymerization" refers to a method of synthesizing polymers using the well-known concept of addition polymerization, that is, polymerization wherein monomers are added one-by-one to an active site on the growing polymer chain but one wherein the active sites for continuing addition of another monomer are never fully eliminated other than on purpose. That is, the polymer chain is virtually always capable of further extension by the addition of more monomer to the reaction mixture unless the polymer has been capped, which may be reversible so as permit polymerization to continue or quenched, which is usually permanent. While numerous genera of living polymerizations are known, currently the predominant types are anionic, cationic and radical living polymerizations. Of these, at present radical polymerization is of particular interest with regard to this invention. Radical polymerization involves a free radical initiator that extracts one of the pi electrons of the double bond of an ethylenic monomer resulting in a reactive unpaired electron on the carbon at the other end of the former double bond from that with which the initiator reacted. The unpaired electron then reacts with the double bond of another monomer creating a stable sigma bond and another free radical and so on. With conventional initiators the sequence is eventually stopped by a termination reaction, generally a combination reaction in which the unpaired electrons of two propagating chains combine to form a stable sigma bond or a disproportionation in which a radical on a active chain strips a hydrogen atom from another active chain or from an impurity in the reaction mixture to produce a stable unreactive molecule and a molecule containing a double bond. In a living polymerization the ability of the growing chains to enter into a termination reaction is eliminated, effectively limiting the polymerization solely by the amount of monomer present; that is, the polymerization continues until the supply of monomer has been exhausted. At this point the remaining free radical species become substantially less active due to capping of the free radical end group with such entities as, without limitation, nitroxyl radicals, halogen molecules, oxygen species such as peroxide and metals or simply by interaction with solvent and the like. If, however, more monomer is added to the solution, the polymerization reaction can resume except as noted above.

Synthesis

Polymers described herein can be prepared in any suitable manner. For example, in certain embodiments, wherein polymers of this invention, while being in no way limited to ethylenic species, with regard to such polymers, it presently particularly preferred that they be prepared by "living polymerization."

Using living polymerization, polymers of very low polydispersity or differences in chain length can be obtained. Polydispersity is usually measured by dividing the weight average molecular weight of the polymer chains by their number average molecular weight. The number average molecule weight is sum of individual chain molecular weights divided by the number of chains. The weight average molecular weight is proportional to the square of the molecular weight divided by the number of molecules of that molecular weight. Since the weight average molecular weight is always greater than the number average molecular weight, polydispersity is always greater than or equal to one. As the numbers come closer and closer to being the same, i.e., as the polydispersity approaches a value of one, the polymer becomes closer to being monodisperse in which every chain has exactly the same number of constitutional units. Polydispersity values approaching one are achievable using radical living polymerization. Methods of determining polydispersity such as, without limitation, size exclusion chromatography, dynamic light scattering, matrix-assisted laser desorption/ionization chromatography and electrospray mass chromatography are well known in the art and will not be further described herein.

Reversible addition-fragmentation chain transfer or RAFT is a presently preferred living polymerization technique for use in synthesizing ethylenic backbone polymer of this invention. RAFT is well-known to those skilled in the art and will only briefly be described herein. RAFT comprises a free radical degenerative chain transfer process. Most RAFT procedures employ thiocarbonylthio compounds such as, without limitation, dithioesters, dithiocarbamates, trithiocarbonates and xanthates to mediate polymerization by a reversible chain transfer mechanism. Reaction of a polymeric radical with the C═S group of any of the preceding compounds leads to the formation of stabilized radical intermediates. These stabilized radical intermediates do not undergo the termination reactions typical of standard radical polymerization but, rather, reintroduce a radical capable of re-initiation or propagation with monomer, reforming the C═S bond in the process. This cycle of addition to the C═S bond followed by fragmentation of the ensuing radical continues until all monomer has been consumed or the reaction is quenched. The low concentration of active radicals at any particular time limits normal termination reactions. In other embodiments, polymers are synthesized by Macromolecular design via reversible addition-fragmentation chain transfer of Xanthates (MADIX) (Direct Synthesis of Double Hydrophilic Statistical Di- and Triblock Copolymers Comprised of Acrylamide and Acrylic Acid Units via the MADIX Process", Daniel Taton, et al., Macromolecular Rapid Communications, 22, No. 18, 1497-1503 (2001).)

Polymer:Biomolecule Constructs

Provided in certain embodiments herein are polymer: polynucleotide constructs, or other constructs including, e.g., polymer:peptide constructs, polymer:polypeptide constructs, or other types of polymer:biomolecule constructs. In certain embodiments, one or more polynucleotide (e.g., siRNA) is associated with any polymer described herein. In various embodiments, polynucleotide, peptides, polypeptides, or other biomolecules are conjugated to the polymer in any suitable manner (e.g., by covalent and/or non-covalent interactions), and such conjugation is at any suitable location, including, e.g., at the alpha end of the polymer, the omega end of the polymer, the hydrophilic end of the polymer, the hydrophobic end of the polymer, or to a pendant group attached to a monomer side chain of the polymer.

As used herein, a polynucleotide refers to a member of the genus of organic polymer molecules comprised of a linear chain of nucleotide monomers covalently bonded in a chain, as such are well-known to those skilled in the art. In brief, a nucleotide comprises a nucleoside that linked to a single phosphate group (or, by convention, when referring to its incorporation into a polynucleotide, a short-hand for a nucleoside triphosphate which is the species that actually undergoes polymerization in the presence of a polymerase). A nucleoside, in turn, comprises a base linked to a sugar moiety. For naturally-occurring polynucleotides, i.e., polynucleotides produced by unmodified living entities, the sugar moiety is either ribose, which gives rise to ribonucleic acids or RNAs or deoxyribose, which gives rise to deoxyribonucleic acids or DNA. The naturally-occurring bases are adenine (A), guanine (G) or its natural substitute inosine (I), cytosine (C) or thymine (T) or its natural substitute uracil (U). A polynucleotide, then, comprises a plurality of nucleosides connected by a phosphodiester linkage between the 3'-hydroxyl group of the sugar moiety of one nucleoside and the 5'-hydroxyl of the sugar moiety of a second nucleoside which in turn is linked through its 3'-hydroxyl to the 5'- of yet another nucleoside and so on.

A DNA or an RNA of this invention may be sense or antisense. DNA is double-stranded, one strand being the sense strand and the other being its complement or antisense strand. The sense strand is characterized by the fact that an RNA version of the same sequence can be translated into a protein. The antisense strand cannot participate in the same sequence. The consequence of this is that protein production by a particular DNA or its messenger RNA can be interrupted by introducing a complementary or antisense polynucleotide at the appropriate stage of protein production.

In brief, protein production occurs in two phases, transcription and translation. In transcription, DNA is used as a template to create messenger RNA or mRNA. In the translation phase, the mRNA travels to a region of the cell where it communicates the genetic message provided by the DNA to the ribosome, which is the cellular machinery that actually assembles the protein encoded for by the DNA. An antisense polynucleotide, which comprises a nucleic acid sequence that is complementary to that of an mRNA can bind or hybridize to the mRNA and the hybridized mRNA is subsequently degraded by one or more biochemical mechanisms thereby preventing the mRNA's instructions from reaching the ribosome. It is presently preferred that a polynucleotide of this invention be an RNA.

The RNA of this invention may be sense or antisense mRNA, micro or miRNA or short interfering RNA, siRNA. mRNA is discussed above. miRNAs are single-stranded RNA molecules about 21-23 nucleotides in length. Their function is to regulate gene expression. miRNAs are encoded by genes that are transcribed from DNA but are not translated into protein. Rather, they are processed from primary transcripts known a pri-miRNA to short stem-loop structures called pre-miRNA and finally to functional miRNA. Functional miRNAs are partially complementary to one or more mRNAs. As such, they perform like the antisense polynucleotides discussed above and prevent mRNAs instructions from reaching the ribosome. They thus are capable of down-regulating gene expression.

While miRNAs are transcribed from the genome itself, siRNAs, small interfering or short interfering RNAs, are not. siRNA, since its discovery in 1999, has become one of the most studied polynucleotides in the molecular biologists' arsenal and is currently considered a prime candidate for a next generation of drugs, since they are potentially able to silence the expression of virtually any gene. For the purposes of this invention, any siRNA currently known or as may become known in the future can be used to form complexes of this invention with the diblock copolymers herein and thereupon can be transported into the interior of living cells for, without limitation, therapeutic, prophylactic or diagnostic purposes. Initially it was thought that exogenously added siRNAs had to be of a specific length (21-23 bp) with very specific 2-base overhangs to be active as siRNAs, but it is now clear that longer or shorter blunt-ended, as well as 27+ bp RNAs are just as effective at gene silencing in mammalian cells. The shorter siRNAs can be loaded directly into the RNA-induced silencing complex (RISC), while longer double-stranded RNAs can be cleaved by the cytoplasmic multidomain endonuclease Dicer into shorter siRNAs in the cytoplasm. In brief, long double-stranded RNA enters the cytoplasm of a cell. The long double stranded RNA is processed into 20 to 25 nucleotide siRNAs by an RNase III-like enzyme called Dicer. The siRNA then assemble into endoribonuclease-containing complexes known as RNA-induced silencing complex or RISC. After integration into the RISC, the sense strand of the double-stranded siRNAs is unwound and/or cleaved leaving the siRNA antisense strand which guides the RISC to a complementary mRNA molecule. The siRNA then binds to the complementary mRNA and once bound, the RISC cleaves the target mRNA, effectively silencing the gene associated with that RNA. Another subgenus of polynucleotides that may form complexes with diblock copolymers of this invention and thereby transported into living cells are the so-called "locked nucleic acid" or LNA polynucleotides. Locked nucleic acid polynucleotides may be prepared by a number of mechanisms one of which is the formation of a 2'-oxygen to 4'-carbon methylene linkage in the sugar moiety of a nucleoside; however, use of any locked nucleic acid polynucleotide is within the scope of this invention. One characteristic of LNAs is their enhanced thermal stability when hybridized with complementary DNAs or RNAs compared to unmodified DNA:DNA or DNA:RNA duplexes as well as enhanced nucleic acid recognition. These properties make LNA polynucleotides potentially useful in a host of molecular application. For example, a comparison of an LNA-DNA-LNA construct with siRNA, phosphorothioate and 2'-O-methyl RNA-DNA constructs against expression of vanilloid receptor subtype 1 (VR1) in Cos-7 cells revealed that, while siRNA were the most potent antisense agents against VR1 expression, the LNA-DNA-LNA construct was 175- and 550-fold more potent in suppressing VR1 than isosequential phosphorothioate and 2D-methyl oligonucleotides. Grunweller, A., et al., 2003, *NAR,* 31:2185-3193.

An aspect of this invention is a polynucleotide or a plurality of polynucleotides that are attached to or associated with (e.g., in a covalent and/or non-covalent manner, including ionic interactions, hydrogen-bonding interactions, and/or van der Waals interactions) any polymer described herein. In certain embodiments, the association between the polymer and polynucleotide is achieved by covalent bonds, non-covalent interactions, or combinations thereof. In specific embodiments, non-covalent associations of the polymer (e.g., of the first block thereof) with the polynucleotide are used. Non-covalent interactions include, without limitation, ionic interactions, hydrogen bonding and van der Waals forces but for the purposes of the current invention the non-covalent interaction comprises ionic interactions. The ionic interaction arises between the cationic constitutional unit of a polymer (e.g., of the first block thereof) and the polynucleotide, which is naturally negatively charged by virtue of the phosphodiester linkages:

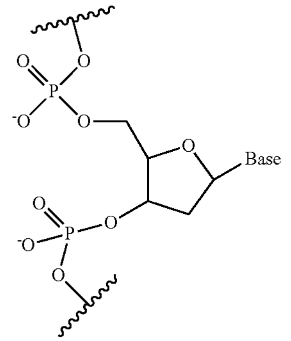

Non-covalent association may be achieved by several additional methods. The polynucleotides and/or the polymer may be modified with chemical moieties that lead them to have an affinity for one another, such as a linkage, arylboronic acid-salicylhydroxamic acid, leucine zipper or other peptide motifs, ionic interactions between positive and negative charges on the polymer and polynucleotide, or other types of non-covalent chemical affinity linkages. Additionally, a double-stranded polynucleotide can be complexed to a polymer of the present invention by forming a polymer with a minor groove binding or an intercalating agent covalently attached to the polymer.

In some embodiments, the polynucleotide may be chemically conjugated to the polymer by any standard chemical conjugation technique. The covalent bond between the polymer and the polynucleotide may be non-cleavable, or cleavable bonds may be used. Particularly preferred cleavable bonds are disulfide bonds that dissociate in the reducing environment of the cytoplasm. Covalent association is achieved through chemical conjugation methods, including but not limited to amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. Conjugation can also be performed with pH-sensitive bonds and linkers, including, but not limited to, hydrazone and acetal linkages. A large variety of conjugation chemistries are established in the art (see, for example, *Bioconjugation*, Aslam and Dent, Eds, Macmillan, 1998 and chapters therein). Polynucleotides may be conjugated to the alpha or omega ends of the polymer, or to the pendant groups on the polymer monomers.

A series of polymers and their respective siRNA-condensed particles are characterized for size and surface charge and the resulting data are shown in Table 2.

In certain instances, polymers appear unimeric (<10 nm) in solution. Complexes formed from polymers and siRNA at theoretical charge ratios of 4:1 ranged in sizes from 85-236 nm. There seemed to be no definitive trend for the complex sizes with respect to BMA content. However, polymer P7 with 48% BMA content in the endosomolytic block exhibited the smallest particle size of 85 nm±0.20. The remainder of the particles had sizes from 144 to 236 nm, where the greatest sized particles were formed from polymer 6 which had 27% BMA content in the endosomolytic block. Polymer P7/siRNA particle sizes were further examined with charge ratios ranging from 1:1 to 8:1, and data are shown in Table 3. Polymer/siRNA particle sizes decrease dramatically as charge ratio increases with values of 643 nm±0.09 at 1:1 to 54 nm±0.27 at 8:1.

TABLE 2

Size and ζ-potential measurements of particles formulated with siRNA at a theoretical charge ratio of 4:1 as a function of butyl methacrylate composition.

| Polymer # | Diameter (nm) | PDI | Zeta Potential (mV) | Standard Error |
|---|---|---|---|---|
| P1 | 166 | 0.14 | 1.1 | 1.32 |
| P2 | 189 | 0.09 | 0.13 | 0.69 |
| P3 | 197 | 0.06 | 0.47 | 0.59 |
| P4 | 144 | 0.11 | 0.41 | 1.2 |
| P5 | 193 | 0.32 | 0.52 | 0.77 |
| P6 | 236 | 0.06 | 0.67 | 0.95 |
| P7 | 85 | 0.20 | 0.18 | 1.0 |

TABLE 3

Size and ζ-potential measurements of particles formulated with polymer 7, the composition with the greatest butyl content, and siRNA as a function of charge ration.

| Theoretical Charge Ratio (+/−) | Diameter (nm) | PDI | Zeta Potential (mV) | Standard Error |
|---|---|---|---|---|
| 1:1 | 643 | 0.09 | 0.27 | 1.1 |
| 2:1 | 530 | 0.16 | 0.99 | 0.91 |
| 4:1 | 85 | 0.2 | 0.18 | 1.01 |
| 8:1 | 54 | 0.27 | 0.41 | 0.81 |

In certain instances, surface charge of siRNA/polymer complexes, based on ζ-potential measurements, is found to be similar and slightly positive for all polymers (~0.5 mV with a range of 0.13-1.1 mV). Moreover, in some instances, complexes formed at +/− of 1:1, 2:1, 4:1, and 8:1 using polymer 7 showed no difference in surface charges, again with slightly positive values (0.18-0.99 mV) with no trend with respect to charge ratio. In some instances, at 1:1 charge ratios, particles are expected to have very little surface charge, as the PAA and DMAEMA charges in the second block counterbalance each other. In various instances, as the charge ratio increases to 2:1, 4:1, and 8:1, one would expect to see increases in positive surface charge, but interestingly, such was not observed. In some instances, with increasing amounts of polymer, the particles change morphology, becoming more tightly packed. With increasing charge ratio, it is possible that the surface charge is unaffected due to effective shielding of the DMAEMA positive charges, as many polymer chains and siRNA become packed within the core of the particles.

In certain embodiments, the alterations in particle size and surface charge may be relevant design criteria with regard to complex uptake by a cell. In some instances, nanoparticles bearing a positive surface charge facilitate uptake by electrostatic interactions with negatively charged cell membranes.

Both polymer and siRNA/polymer complexes were evaluated for their ability to induce red blood cell hemolysis at pH values relevant to the endosomal/lysosomal trafficking pathway. Significant hemolysis did not occur for polymers 1-3. However, relevant pH-dependent hemolytic activity was evident with polymer 4, and enhanced responsiveness was found as BMA content of the endosomolytic block increased. Polymer 7 exhibited the greatest pH-dependent hemolysis with essentially no activity at pH=7.4, about 25% hemolysis at pH=6.6, and 85% hemolysis at pH=5.8. Polymers 5-7 were subsequently evaluated for hemolytic activity in their siRNA-complexed form. Complexes formed with polymers 5-7 at all charge ratios tested were found to be hemolytic in a relevant pH-dependent fashion. Moreover, the hemolysis exhibited by complexes was increased when compared with free polymer and was greater at a charge ratio of 4:1 versus 1:1. Polymer 7 showed the greatest hemolytic activity at a charge ratio of 4:1, with essentially no hemolysis at pH=7.4, 60% hemolysis at pH=6.8, and 100% hemolysis at pH 5.8. These data suggest that the pH-responsive hemolytic activity of these polymers is linked to the incorporation of the hydrophobicity enhancing moiety, butyl methacrylate. This finding corroborates previous reports on pH-responsive, membrane destabilizing polymers that have utilized incorporation of hydrophobic moieties such as alkyl amines or aromatic groups to enhance the pH-dependent hydrophobic transition of carboxylate functionalized polymers.

Membrane Disruption and/or Membrane Destabilization

In certain embodiments, a polymer or polymer: polynucleotide construct (i.e., comprising any polymer described herein associated with one or more polynucleotide) is a cellular membrane destabilizing or disruptive polymer (i.e., is destabilizing or disruptive of a cellular membrane). In certain embodiments, the cellular membrane is, by way of non-limiting example, an extracellular membrane, an intracellular membrane, a vesicle, an organelle, an endosome, a liposome, or a red blood cell. In some embodiments, when administered to a cell, the membrane disruptive polymer or polymer:polynucleotide is delivered into the cell. In certain embodiments, siRNA is a preferred polynucleotide to be associated with a polymer of this invention and subsequently endocytosed with the polymer into the interior of living cells Endocytosis is the process by which a substance (for example, a polymer, or nucleic acid of the present invention) gains entrance into a cell without having to traverse the plasma membrane. The substance is enveloped by a portion of the cell membrane which then is pinched off forming an intracellular vesicle. Once the substance has been endocytosed and the endosome has acidified, the chemical composition of the polymer is altered because the pKa of the polymer is selected such that, at the pH within a mature endosome, approximately 5-6.5, the equilibrium between the un-ionized and the ionized forms of the acidic units, i.e., the anionic constitutional units of a polymer of this invention, is shifted to the un-ionized form. In contrast to the ionized form of the polymer, which is relatively hydrophilic, the un-ionized form is substantially hydrophobic and capable of interaction, i.e., disruption of, the endosomal membrane which results in the release of the substance into the cytosol.

Cellular internalization of siRNA complexes at 4:1 charge ratios was investigated using flow cytometry for polymers P4-P7 based on their relevant pH-responsive endosomolytic characteristics. Following 4 hours of exposure to 25 nM of polymer-complexed siRNA, cellular uptake was found to positively correlate with BMA content of the second block, with polymer P7 showing the highest level of uptake (23% siRNA positive cells) during this timeframe. Positively charged complexes have been previously demonstrated to affect internalization of cationic polymer/nucleic acid complexes, with positively charged complexes achieving higher internalization rates and transgene expression. These results are likely not a function of surface charge or size, as all the particles exhibit the same, slightly positive net charge and sizes (85-236 nm) well within the limits for non-specific endocytosis (Table 2). Rather, the effect on uptake may be a function of the endosomolytic effectiveness of the BMA-containing block. Based on hemolysis results, as BMA content increases, endosomal escape occurs to a greater extent, thus recycling from the cell decreases and net accumulation of siRNA within the cell increases, similar to other propylacrylic acid-containing bioconjugates. Based on electrostatic repulsion between siRNA and cell membranes, all polymer formulations showed much greater uptake (up to 25×) by cells than siRNA not complexed with a carrier (naked siRNA). Internalization of complexed siRNA by up to 23% of cells only after 4 hours is extremely promising for therapeutic efficacy, as the cumulative uptake is likely to be much higher after the full 48 hour treatment. In addition, siRNA activity is considered to be catalytic; it can be recycled within the cytoplasm to destroy multiple mRNA transcripts, therefore having a long-term, multi-generational effect.

The nonspecific cytotoxicity of the polymer carriers was investigated by incubating HeLa cells in the presence of the complexes at charge ratios of 4:1 for 24 hours. High relative survival was observed (>90% after 24 hours) for all polymers tested. Synthetic polymers, in particular cationic polymers, can be associated with appreciable cytotoxicity. For instance, PEI has been shown to trigger apoptosis and/or necrosis in a variety of cell lines. This toxicity can be reduced by chemically modifying the polycation segment with hydrophilic segments; however, there is usually a tradeoff between efficacy and toxicity. In this approach, the use of a charge-neutralized second block of the polymer delivery vehicle presumably maintained high survivability of in vitro cultured HeLa cells.

The ability of the carriers to effectively deliver siRNA was investigated with knockdown experiments against GAPDH with complexes formed from all polymers at theoretical charge ratios of 4:1. GAPDH protein levels were evaluated 48 hours after treatment with the complexes. Polymer carriers 1-3 were ineffectual at eliciting reduction of protein levels, likely due to their inability to mediate endosomal escape. However, GAPDH protein reduction became evident with the use of polymer 4 as a siRNA carrier. The knockdown of protein further increased as the BMA content of the carriers increased to 48% of the endosomolytic block (polymer P7). Polymer P7 showed the greatest ability to mediate siRNA knockdown of protein where GAPDH was reduced to 32% of control. Furthermore, control siRNA showed negligible reduction in GAPDH protein levels.

To further characterize carrier efficacy, polymers were analyzed for their ability to knockdown GAPDH mRNA levels. Similar to the protein measurements, polymers 1-3 elicited very little reduction of mRNA signal, as evaluated by RT-PCR. Again, polymers P4-P7 showed increased knockdown of GAPDH as the BMA content of the endosomolytic block increased. Specifically, GAPDH knockdown was reduced to 39%, 30%, 31%, and 21% of control at a charge ratio of 4:1, for polymers P4, P5, P6, and P7, respectively. Overall, the results are consistent with findings from other groups exploring delivery strategies for DNA which have found that the addition of hydrophobic domains, specifically N-oleyl moieties, phenylalanine resides, and butyl methacrylate, as utilized here, enhance transfection.

Further investigation into ability of P7, which includes the polymer of Table 2 and similar structures (including various versions of P7, such as P7v6, which is used interchangeably herein with PRx0729v6), to mediate gene knockdown was performed with respect to charge ratio and siRNA dose. Alteration of theoretical charge ratios was found to greatly affect gene knockdown. GAPDH was reduced to 51%, 42%, 21%, and 14% of control levels with charge ratios of 2:1, 4:1, and 8:1, respectively. Particularly at charge ratios of 4:1 and 8:1, gene knockdown was similar to the commercially available carrier HiPerFect, where GAPDH levels were reduced by over 80%. Importantly, the effects on GAPDH levels are specific to the siRNA that is delivered, as when a control siRNA is utilized at a charge ratio of 8:1, there is no significant effect on GAPDH Altering the charge ratio may have resulted in differing levels of condensation of the siRNA within the nanoparticles. DLS experiments indicated that increasing copolymer content in the complexes resulted in more condensed particles (Table 3), and these functional studies suggest that more compact particles can be internalized more efficiently or with increased siRNA bioavailability. These findings are consistent with previous reports indicating that more compact DNA/polyethyleneimine and DNA/polylysine complexes internalize at higher rates and achieve higher transfection efficiencies. A dose-response study using P7 at a charge ratio of 4:1 was conducted. Although there was little response in GAPDH gene expression at 1 nM or 5 nM siRNA, expression was reduced to 77%, 21%, and 12% of control when 10 nM, 25 nM, or 50 nM of siRNA was delivered using polymer 7. This level of knockdown approaches that seen using 50 nM HiPerFect, a commercially available positive control. However, all polymers, including polymer 7, demonstrated enhanced biocompatibility, as measured by nonspecific cytotoxicity compared to HiPerFect. Although significant levels of gene knockdown with higher doses of siRNA (25-50 nM) were achieved, for translation to in vivo applications, it may be more desirable to achieve significant reduction using lower doses of siRNA to avoid off-target effects. In some embodiments, this is accomplished by more efficient uptake of the polymer/siRNA particles, perhaps best accomplished by targeting ligands.

Uses

In certain embodiments, the polynucleotides of this invention that are administered to a subject and ultimately delivered into the subject's cells are preferably DNA, RNA or natural or synthetic analogs thereof. With regard to DNA/RNA and analogs thereof that are able to inhibit expression of target genes, these include such species as, without limitation, antisense polynucleotides, miRNA and siRNA.

Diseases that are optionally treated using polymers and/or polymer: polynucleotide complexes of this invention include, without limitation, pathogenic disorders, cancers, inflammatory diseases, enzyme deficiencies, inborn errors of metabolism, infections, auto-immune diseases, cardiovascular diseases, neurological, neurodegenerative, diseases, neuromuscular diseases, blood disorders and clotting disorders.

The following examples are for illustration purposes and are not to be construed as limiting the invention. All publications recited herein are hereby incorporated by reference for the information to which the publications are cited.

EXAMPLES

Throughout the description of the present invention, various known acronyms and abbreviations are used to describe monomers or monomeric residues derived from polymerization of such monomers. Without limitation, unless otherwise noted: "BMA" (or the letter "B" as equivalent shorthand notation) represents butyl methacrylate or monomeric residue derived therefrom; "DMAEMA" (or the letter "D" as equivalent shorthand notation) represents N,N-dimethylaminoethyl methacrylate or monomeric residue derived therefrom; "Gal" refers to galactose or a galactose residue, optionally including hydroxyl-protecting moieties (e.g., acetyl) or to a pegylated derivative thereof (as described below); HPMA represents 2-hydroxypropyl methacrylate or monomeric residue derived therefrom; "MAA" represents methylacrylic acid or monomeric residue derived therefrom; "MAA(NHS)" represents N-hydroxyl-succinimide ester of methacrylic acid or monomeric residue derived therefrom; "PAA" (or the letter "P" as equivalent shorthand notation) represents 2-propylacrylic acid or monomeric residue derived therefrom, "PEGMA" refers to the pegylated methacrylic monomer, $CH_3O(CH_2O)_{7-8}OC(O)C(CH_3)CH_2$ or monomeric residue derived therefrom. In each case, any such designation indicates the monomer (including all salts, or ionic analogs thereof), or a monomeric residue derived from polymerization of the monomer (including all salts or ionic analogs thereof), and the specific indicated form is evident by context to a person of skill in the art.

Example 1

Preparation of Di-Block Polymers and Copolymers

Di-block polymers and copolymers of the following general formula are prepared:

$$[A1_x\text{-/-}A2_y]_n\text{-}[B1_x\text{-/-}B2_y\text{-/-}B3_z]_{1\text{-}5n}$$

Where [A1-A2] is the first block copolymer, composed of residues of monomers A1 and A2

[B1-B2-B3] is the second block copolymer, composed of residues of monomers B1, B2, B3 x, y, z is the polymer composition in mole % monomer residue n is molecular weight Exemplary di-block copolymers:

[DMAEMA]-[B-/-P-/-D]

$[PEGMA_w]$-[B-/-P-/-D]

$[PEGMA_w$-DMAEMA]-[B-/-P-/-D]

$[PEGMA_w$-MAA(NHS)]-[B-/-P-/-D]

[DMAEMA-/-MAA(NHS)]-[B-/-P-/-D]

[HPMA-/-PDSM]-[B-/-P-/-D]

Where:

B is butyl methacrylate

P is propyl acrylic acid

D is DMAEMA is dimethylaminoethyl methacrylate

PEGMA is polyethyleneglycol methacrylate where, for example, w=4-5 or 7-8 ethylene oxide units)

MAA(NHS) is methylacrylic acid-N-hydroxy succinamide

HPMA is N-(2-hydroxypropyl)methacrylamide

PDSM is pyridyl disulfide methacrylate

These polymers represent structures where the composition of the first block of the polymer or copolymer is varied or chemically treated in order to create polymers where the first block is neutral (e.g., PEGMA), cationic (DMAEMA), anionic (PEGMA-NHS, where the NHS is hydrolyzed to the acid), ampholytic (DMAEMA-NHS, where the NHS is hydrolyzed to the acid), or zwiterrionic (for example, poly [2-methacryloyloxy-2' trimethylammoniumethyl phosphate]). In addition, the [PEGMA-PDSM]-[B-P-D] polymer contains a pyridyl disulfide functionality in the first block that can be reacted with a thiolated siRNA to form a polymer-siRNA conjugate.

Example 1.1

General Synthetic Procedures for Preparation of Block Copolymers by Raft

A. Raft Chain Transfer Agent.

The synthesis of the chain transfer agent (CTA), 4-Cyano-4-(ethylsulfanylthiocarbonyl) sulfanylpentanoic acid (ECT), utilized for the following RAFT polymerizations, was adapted from a procedure by Moad et al., *Polymer,* 2005, 46(19): 8458-68. Briefly, ethane thiol (4.72 g, 76 mmol) was added over 10 minutes to a stirred suspension of sodium hydride (60% in oil) (3.15 g, 79 mmol) in diethyl ether (150 ml) at 0° C. The solution was then allowed to stir for 10 minutes prior to the addition of carbon disulfide (6.0 g, 79 mmol). Crude sodium S-ethyl trithiocarbonate (7.85 g, 0.049 mol) was collected by filtration, suspended in diethyl ether (100 mL), and reacted with Iodine (6.3 g, 0.025 mol). After 1 hour the solution was filtered, washed with aqueous sodium thiosulfate, and dried over sodium sulfate. The crude bis(ethylsulfanylthiocarbonyl) disulfide was then isolated by rotary evaporation. A solution of bis-(ethylsulfanylthiocarbonyl) disulfide (1.37 g, 0.005 mol) and 4,4'-azobis(4-cyanopentanoic acid) (2.10 g, 0.0075 mol) in ethyl acetate (50 mL) was heated at reflux for 18 h. Following rotary evaporation of the solvent, the crude 4-Cyano-4 (ethylsulfanylthiocarbonyl) sulfanylvpentanoic acid (ECT) was isolated by column chromatography using silica gel as the stationary phase and 50:50 ethyl acetate hexane as the eluent.

B. Poly(N,N-dimethylaminoethyl methacrylate) Macro Chain Transfer Agent (polyDMAEMA macroCTA).

The RAFT polymerization of DMAEMA was conducted in DMF at 30° C. under a nitrogen atmosphere for 18 hours using ECT and 2,2'-Azobis(4-methoxy-2,4-dimethyl valeronitrile) (V-70) (Wako chemicals) as the radical initiator. The initial monomer to CTA ratio ($[CTA]_0/[M]_0$ was such that the theoretical $M_n$ at 100% conversion was 10,000 (g/mol). The initial CTA to initiator ratio ($[CTA]_o/[I]_o$) was 10 to 1. The resultant polyDMAEMA macro chain transfer agent was isolated by precipitation into 50:50 v:v diethyl ether/pentane. The resultant polymer was redissolved in acetone and subsequently precipitated into pentane (×3) and dried overnight in vacuo.

C. Block Copolymerization of DMAEMA, PAA, and BMA from a poly(DMAMEA) macroCTA.

The desired stoichiometric quantities of DMAEMA, PAA, and BMA were added to poly(DMAEMA) macroCTA dissolved in N,N-dimethylformamide (25 wt % monomer and macroCTA to solvent). For all polymerizations $[M]_o/[CTA]_o$ and $[CTA]_o/[I]_o$ were 250:1 and 10:1 respectively. Following the addition of V70 the solutions were purged with nitrogen for 30 min and allowed to react at 30° C. for 18 h. The resultant diblock copolymers were isolated by precipitation into 50:50 v:v diethyl ether/pentane. The precipitated polymers were then redissolved in acetone and subsequently precipitated into pentane (×3) and dried overnight in vacuo. Gel permeation chromatography (GPC) was used to determine molecular weights and polydispersities (PDI, $M_w/M_n$) of both the poly(DMAEMA) macroCTA and diblock copolymer samples in DMF with respect to polymethyl methacrylate standards (SEC Tosoh TSK-GEL R-3000 and R-4000 columns (Tosoh Bioscience, Montgomeryville, Pa.) connected in series to a Viscotek GPCmax VE2001 and refractometer VE3580 (Viscotek, Houston, Tex.). HPLC-grade DMF containing 1.0 wt % LiBr was used as the mobile phase. FIG. 1A summarizes the molecular weights and compositions of some of the RAFT synthesized polymers. (PRx0729v6 is used interchangeably with P7v6 in this application and in various priority applications.) FIG. 1B summarizes the molecular weights, particle size and compositions of some of the RAFT synthesized polymers.

Example 1.2

Preparation of Second Block (B1-B2-133) Copolymerization of DMAEMA, PAA, and BMA from a poly(PEGMA) macroCTA The desired stoichiometric quantities of DMAEMA, PAA, and BMA were added to poly(PEGMA) macroCTA dissolved in N,N-dimethylformamide (25 wt % monomer and macroCTA to solvent). For all polymerizations $[M]_o/[CTA]_o$ and $[CTA]_o/[I]_o$ were 250:1 and 10:1 respectively. Following the addition of AIBN the solutions were purged with nitrogen for 30 min and allowed to react at 68° C. for 6-12 h (FIG. 2). The resulting diblock copolymers were isolated by precipitation into 50:50 v:v diethyl ether/pentane. The precipitated polymers were then redissolved in acetone and subsequently precipitated into pentane (×3) and dried overnight in vacuo. Gel permeation chromatography (GPC) was used to determine molecular weights and polydispersities (PDI, $M_w/M_n$) of both the poly(PEGMA) macroCTA and diblock copolymer samples in DMF using a Viscotek GPCmax VE2001 and refractometer VE3580 (Viscotek, Houston, Tex.). HPLC-grade DMF containing 1.0 wt % LiBr was used as the mobile phase. NMR spectroscopy in $CDCl_3$ was used to confirm the polymer structure and calculate the composition of the $2^{nd}$ block. FIG. 2 summarizes the synthesis of $[PEGMA_w]$-[B-P-D] polymer where w=7-8. FIGS. 3A, 3B and 3C summarize the characterization of $[PEGMA_w]$-[B-P-D] polymer where w=7-8.

Example 1.3

Preparation and Characterization of PEGMA-DMAEMA Co-Polymers

Polymer synthesis was carried out using a procedure similar to that described in Examples 1.1 and 1.2. The ratio of the PEGM and DMAEMA in the first block was varied by using different feed ratios of the individual monomers to create the co-polymers described in FIG. 4.

Example 1.4

Preparation and Characterization of PEGMA-MAA(NHS) Co-Polymers

Figure 5:
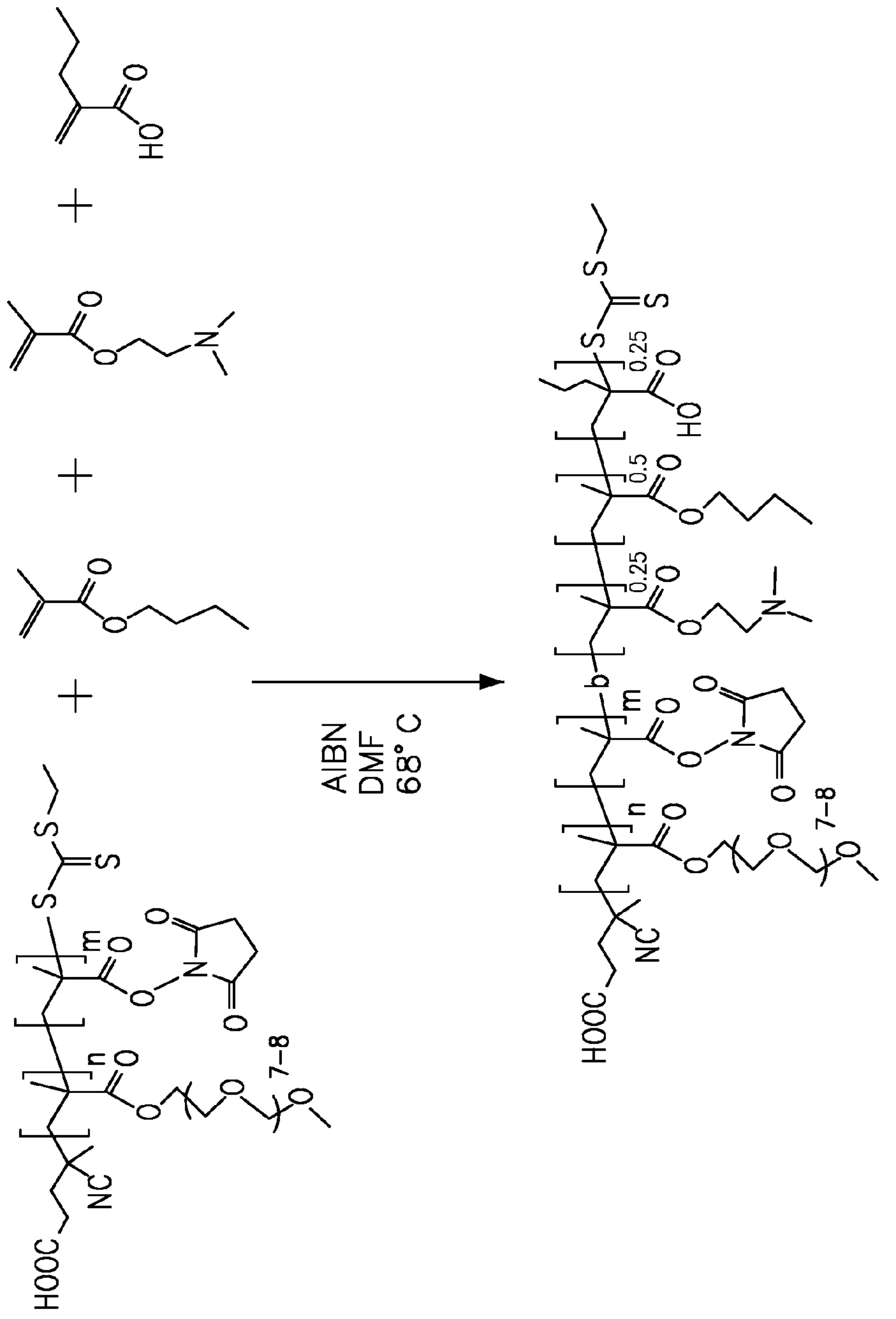
FIG. 5 is an illustrative synthesis of [PEGMAw-MAA (NHS)]-[B-P-D]

Polymer synthesis was performed as described in Examples 1.1 and 1.2 (and summarized in FIG. 5), using monomer feed ratios to obtain the desired composition of the $1^{st}$ block copolymer. FIGS. 6A, 6B and 6C summarize the synthesis and characterization of $[PEGMA_w$-MAA(NHS)]-[B-P-D] polymer where the co-polymer ratio of monomers in the $1^{st}$ block is 70:30. NHS containing polymers can be incubated in aqueous buffer (phosphate or bicarbonate) at pH between 7.4 and 8.5 for 1-4 hrs at room temperature or 37° C. to generate the hydrolyzed (acidic) form.

Example 1.5

Preparation and Characterization of DMAEMA-MAA(NHS) Co-Polymers

Polymer synthesis was performed as described in Examples 1.1 and 1.2, using monomer feed ratios to obtain the desired composition of the $1^{st}$ block copolymer. FIGS. 7A, 7B and 7C summarize the synthesis and characterization of [DMAEMA-MAA(NHS)]-[B-P-D] polymer where the co-polymer ratio of monomers in the $1^{st}$ block is 70:30. NHS containing polymers can be incubated in aqueous buffer (phosphate or bicarbonate) at pH between 7.4 and 8.5 for 1-4 hrs at room temperature or 37° C. to generate the hydrolyzed (acidic) form.

Example 2

Preparation and Characterization of HPMA-PDS(RNA) Co-Polymer Conjugates for siRNA Drug Delivery A. Synthesis of Pyridyl Disulfide Methacrylate Monomer (PDSMA)

Figure 8:
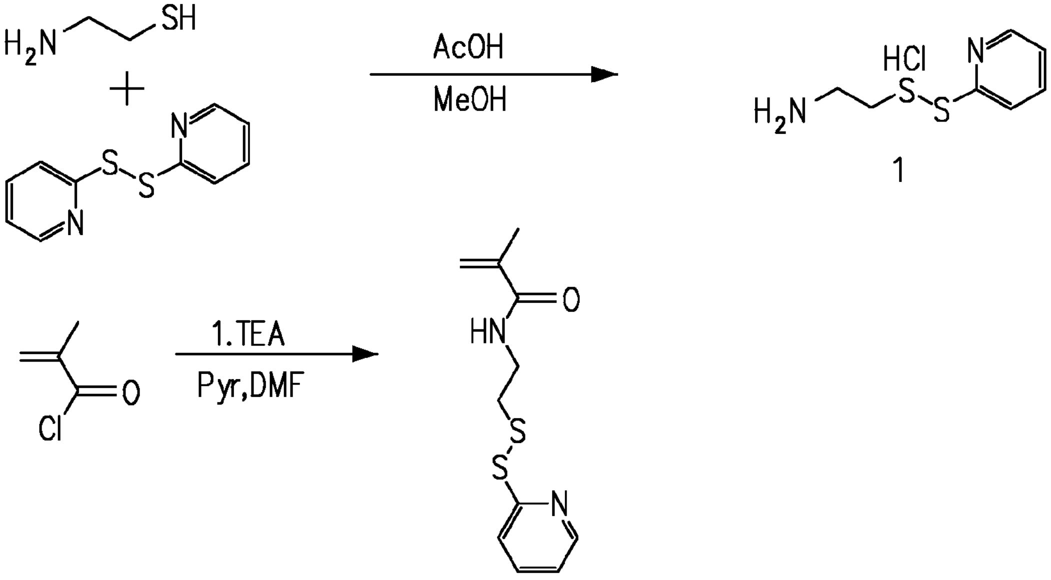
FIG. 8 is an illustrative synthesis of PDSMA

The synthesis scheme for PDSMA is summarized in FIG. 8. Aldrithiol-2™ (5 g, 22.59 mmol) was dissolved in 40 ml of methanol and 1.8 ml of AcOH. The solution was added as a solution of 2-aminoethanethiol.HCl (1.28 g, 11.30 mmol) in 20 ml methanol over 30 min. The reaction was stirred under $N_2$ for 48 h at R.T. After evaporation of solvents, the residual oil was washed twice with 40 ml of diethyl ether. The crude compound was dissolved in 10 ml of methanol and the product was precipitated twice with 50 ml of diethyl ether to get the desired compound 1 as slight yellow solid. Yield: 95%.

Pyridine dithioethylamine (1, 6.7 g, 30.07 mmol) and triethylamine (4.23 ml, 30.37 mmol) were dissolved in DMF (25 ml) and pyridine (25 ml) and methacryloyl chloride (3.33 ml, 33.08 mmol) was added slowly via syringe at 0 C. The reaction mixture was stirred for 2 h at R.T. After reaction, the reaction was quenched by sat. $NaHCO_3$ (350 ml) and extracted by ethyl acetate (350 ml). The combined organic layer was further washed by 10% HCl (100 ml, 1 time) and pure water (100 ml, 2 times) and dried by $MaSO_4$. The pure product was purified by column chromatography (EA/Hex: 1/10 to 2/1) as yellow syrup. Rf=0.28 (EA/Hex=1/1). Yield: 55%.

B. HPMA-PDSMA Co-Polymer Synthesis

Figure 9:
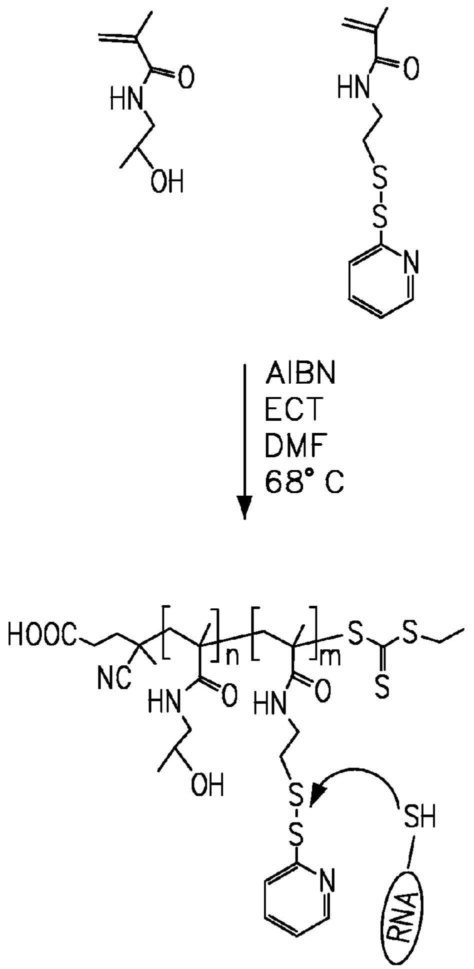
FIG. 9 is an illustrative synthesis of HPMA-PDSMA copolymer for siRNA conjugation

The RAFT polymerization of N-(2-hydroxypropyl)methacrylamide (HPMA) and pyridyl disulfide methacrylate (typically at a 70:30 monomer ratio) is conducted in DMF (50 weight percent monomer:solvent) at 68° C. under a nitrogen atmosphere for 8 hours using 2,2'-azo-bis-isobutyrylnitrile (AIBN) as the free radical initiator (FIG. 9). The molar ratio of CTA to AIBN is 10 to 1 and the monomer to CTA ratio is set so that a molecular weight of 25,000 g/mol would be achieved if at 100% conversion. The poly(HPMA-PDS) macro-CTA was isolated by repeated precipitation into diethyl ether from methanol.

The macro-CTA is dried under vacuum for 24 hours and then used for block copolymerization of dimethylaminoethyl methacrylate (DMAEMA), propylacrylic acid (PAA), and butyl methacrylate (BMA). Equimolar quantities of DMAEMA, PAA, and BMA ($[M]_o/[CTA]_o=250$) are added to the HPMA-PDS macroCTA dissolved in N,N-dimethylformamide (25 wt % monomer and macroCTA to solvent). The radical initiator AIBN is added with a CTA to initiator ratio of 10 to 1. The polymerization is allowed to proceed under a nitrogen atmosphere for 8 hours at 68° C. Afterwards, the resultant diblock polymer is isolated by precipitation 4 times into 50:50 diethyl ether/pentane, redissolving in ethanol between precipitations. The product is then washed 1 time with diethyl ether and dried overnight in vacuo.

C. siRNA Conjugation to HPMA-PDSMA Co-Polymer

Thiolated siRNA was obtained commercially (Agilent, Boulder, Colo.) as a duplex RNA with a disulfide modified 5'-sense strand. The free thiol form for conjugation is prepared by dissolving the lyophilized compound in water and treated for 1 hour with the disulfide reducing agent TCEP immobilized within an agarose gel. The reduced RNA (400 μM) was then reacted for 24 hours with the pyridyl disulfide-functionalized polymer in phosphate buffer (pH 7) containing 5 mM ethylenediaminetetraacetic acid (EDTA) (FIG. 9).

The reaction of the pyridyl disulfide polymer with the RNA thiol creates 2-pyridinethione, which can be spectrophotometrically measured to characterize conjugation efficiency. To further validate disulfide exchange, the conjugates are run on an SDS-PAGE 16.5% tricine gel. In parallel, aliquots of the conjugation reactions are treated with immobilized TCEP prior to SDS-PAGE to verify release of the RNA from the polymer in a reducing environment. Conjugation reactions are conducted at polymer/RNA stoichiometries of 1, 2, and 5. UV spectrophotometric absorbance measurements at 343 nm for 2-pyridinethione release are used to measure conjugation efficiencies.

Example 3 siRNA/Polymer Complex Characterization

After verification of complete, serum-stable siRNA complexation via agarose gel retardation, siRNA/polymer complexes were characterized for size and zeta potential using a ZetaPALS detector (Brookhaven Instruments Corporation, Holtsville, N.Y., 15 mW laser, incident beam=676 nm). Briefly, polymer was formulated at 0.1 mg/ml in phosphate buffered saline (PBS, Gibco) and complexes were formed by addition of polymer to GAPDH siRNA (Ambion) at the indicated theoretical charge ratios based on positively charged DMAEMA, which is 50% protonated at pH=7.4 and the negatively-charged siRNA. Correlation functions were collected at a scattering angle of 90°, and particle sizes were calculated using the viscosity and refractive index of water at 25° C. Particle sizes are expressed as effective diameters assuming a log-normal distribution. Average electrophoretic mobilities were measured at 25° C. using the ZetaPALS zeta potential analysis software, and zeta potentials were calculated using the Smoluchowsky model for aqueous suspensions.

Example 4

HeLa Cell Culture

HeLas, human cervical carcinoma cells (ATCC CCL-2), were maintained in minimum essential media (MEM) containing L-glutamine (Gibco), 1% penicillin-streptomycin (Gibco), and 10% fetal bovine serum (FBS, Invitrogen) at 37° C. and 5% CO2.

Example 5 pH-Dependent Membrane Disruption of Carriers and siRNA/Polymer Complexes

Figure 10A:
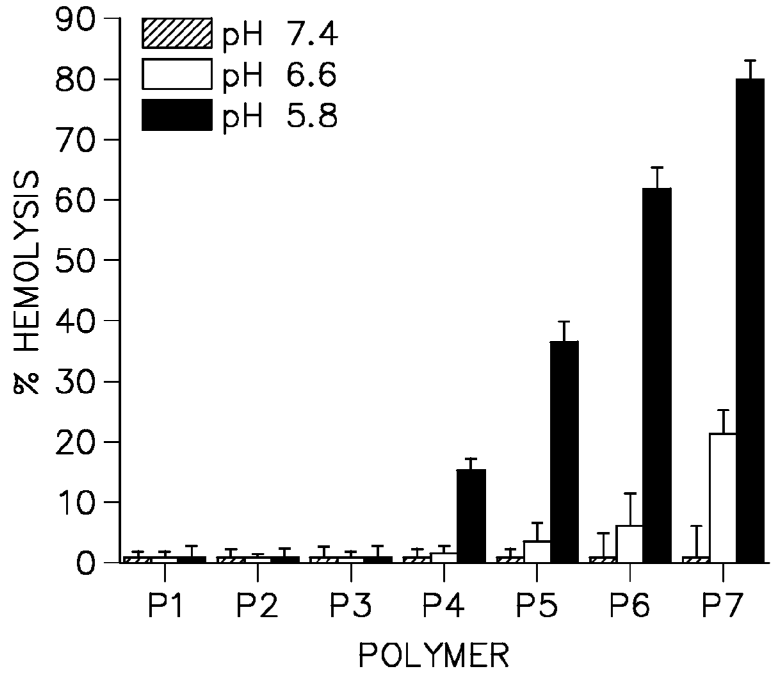
FIG. 10A illustrates the hemolysis of polymers and FIG. 10B illustrates the hemolysis of polymer/siRNA constructs.
Figure 10B:
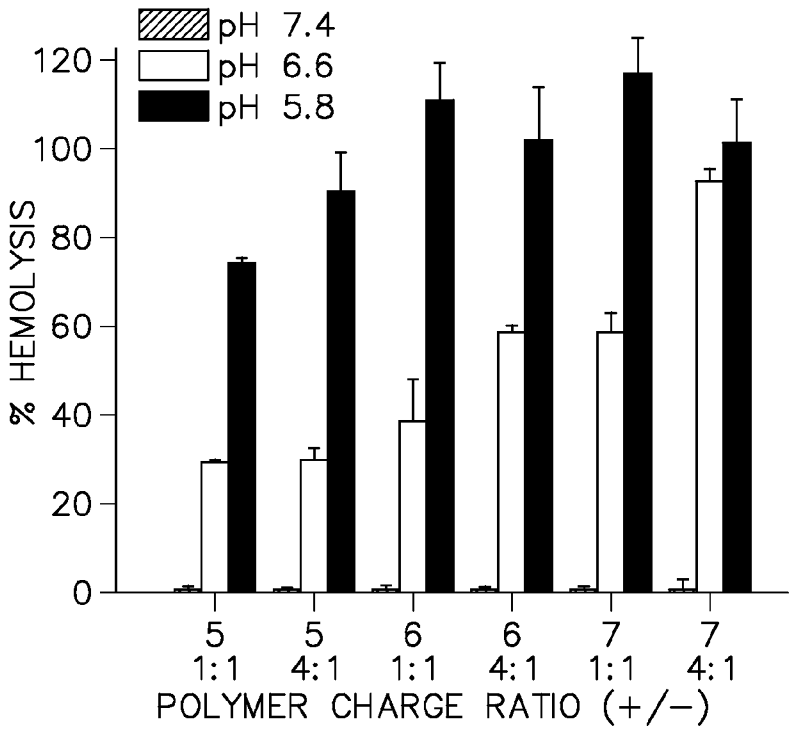

Hemolysis was used to determine the potential endosomolytic activity of both free polymer and siRNA/polymer conjugates at pH values that mimic endosomal trafficking (extracellular pH=7.4, early endosome pH=6.6, and late endosome pH=5.8). Briefly, whole human blood was collected in vaccutainers containing EDTA. Blood was centrifuged, plasma aspirated, and washed three times in 150 mM NaCl to isolate the red blood cells (RBC). RBC were then resuspended in phosphate buffer (PB) at pH 7.4, pH 6.6, or pH 5.8. Polymers (10 ug/ml) or polymer/siRNA complexes were then incubated with the RBC at the three pH values for 1 hour at 37° C. Intact RBC were then centrifuged and the hemoglobin released into supernatant was measured by absorbance at 541 nm as an indication of pH-dependent RBC membrane lysis. FIG. 10A shows the hemolysis of polymers at a concentration of 10 μg/ml and FIG. 10B shows polymer/siRNA complexes of polymers 5-7 at theoretical charge ratios of 1:1 and 4:1. Hemolytic activity was normalized relative to a positive control, 1% v/v Triton X-100 and are representative data from a single experiment conducted in triplicate±standard deviation.

Example 6

Measurement of Carrier-Mediated siRNA Uptake

Figure 11:
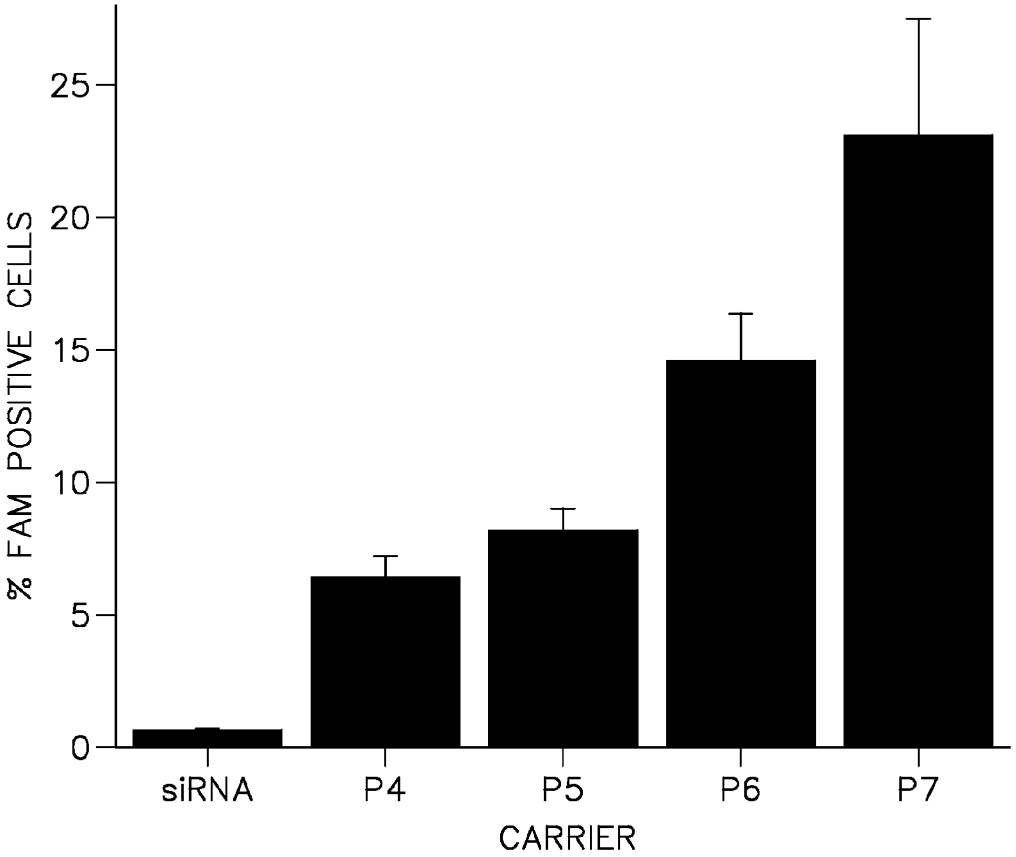
FIG. 11 illustrates HeLa cell internalization of FAM-labeled siRNA and polymer/siRNA complexes.

Intracellular uptake of siRNA/polymer complexes was measured using flow cytometry (Becton Dickinson LSR benchtop analyzer). Helas were seeded at 15,000 cells/cm2 and allowed to adhere overnight. FAM (5-carboxyfluorescine) labeled siRNA (Ambion) was complexed with polymer at a theoretical charge ratio of 4:1 for 30 min at room temperature and then added to the plated HeLas at a final siRNA concentration of 25 nM. After incubation with the complexes for 4 h, the cells were trypsinized and resuspended in PBS with 0.5% BSA and 0.01% trypan blue. Trypan blue was utilized as previously described for quenching of extracellular fluorescence and discrimination of complexes that have been endocytosed by cells. 10,000 cells were analyzed per sample and fluorescence gating was determined using samples receiving no treatment and polymer not complexed with FAM labeled siRNA. FIG. 11 shows HeLa cell internalization of FAM-labeled siRNA and polymer/siRNA complexes formed with polymers 4-7 and delivered for 4 h. Data are from three independent experiments conducted in triplicate with error bars representing standard error of the mean (SEM).

Example 7 siRNA/Polymer Complex Cytotoxicity siRNA/polymer complex cytotoxicity was determined using and lactate dehydrogenase (LDH) cytotoxicity detection kit (Roche). HeLa cells were seeded in 96-well plates at a density of 12,000 cells per well and allowed to adhere overnight. Complexes were formed by addition of polymer (0.1 mg/ml stock solutions) to GAPDH siRNA at theoretical charge ratios of 4:1 and to attain a concentration of 25 nM siRNA/well. Complexes (charge ratio=4:1) were added to wells in triplicate. After cells had been incubated for 24 hours with the polymer complexes, the media was removed and the cells were washed with PBS twice. The cells were then lysed with lysis buffer (100 uL/well, 20 mM Tris-HCl, pH 7.5, 150 mM NaCl, 1 mM $Na_2EDTA$, 1 mM EGTA, 1% Triton, 2.5 mM sodium pyrophosphate, 1 mM β-glycerophosphate, 1 mM sodium orthovanadate) for 1 hour at 4° C. After mixing by pipetting, 20 uL of the cell lysate was diluted 1:5 in PBS and quantified for lactate dehydrogenase (LDH) by mixing with 100 μL of the LDH substrate solution. After a 10-20 min incubation for color formation, the absorbance was measured at 490 nm with the reference set at 650 nm.

Figure 12A:
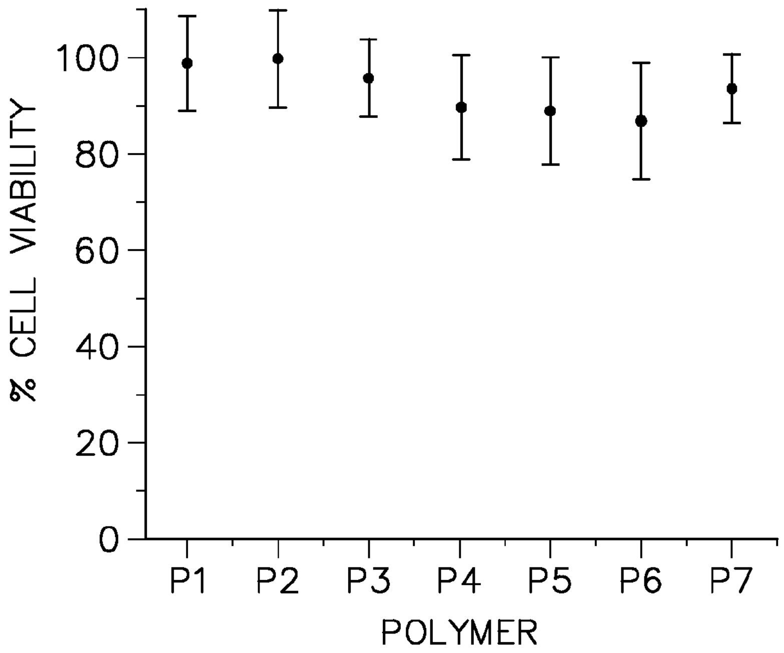
FIG. 12A illustrates nonspecific HeLa cytotoxicity and FIG. 12B illustrates GAPDH knockdown as a function of siRNA polymer carrier.
Figure 12B:
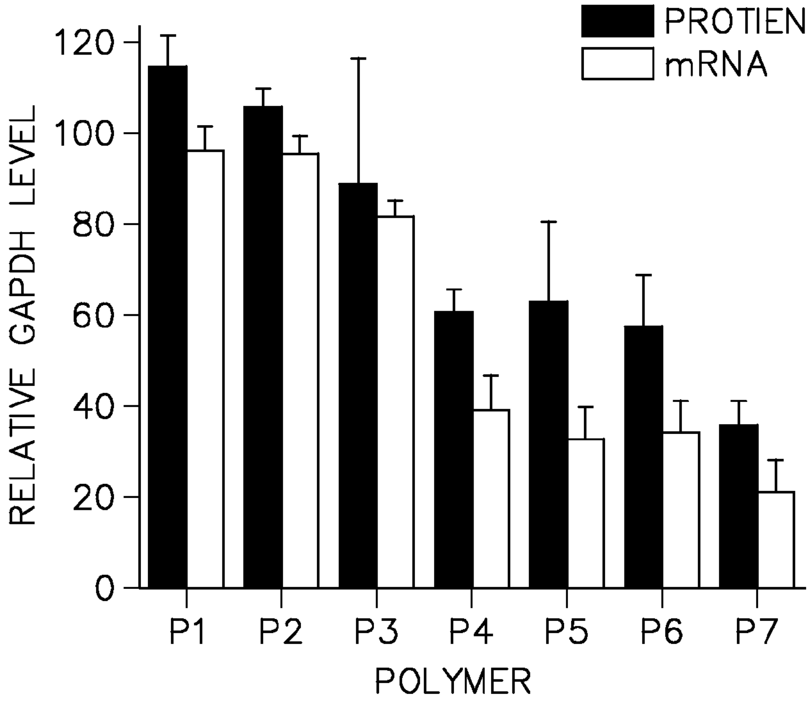

FIG. 12A shows nonspecific HeLa cytotoxicity and FIG. 12B shows GAPDH knockdown as a function of siRNA polymer carrier. HeLa cells were transfected with siRNA against GAPDH at 25 nM using polymer/siRNA complexes formulated at theoretical charge ratios of 4:1. (A) After 24 h, cell lysate was collected and assayed for lactate dehydrogenase, a measure of cell viability, and data is shown relative to untreated cells. (B) After 48 h, both protein (black) and mRNA levels (white) were examined using a GAPDH enzyme activity assay and RT-PCR, respectively, and data is shown relative to cells receiving no treatment. Data are from three independent experiments conducted in triplicate with error bars representing standard deviation.

Example 8

Evaluation of GAPDH Protein and Gene Knockdown by siRNA/Polymer Complexes

Figure 13A:
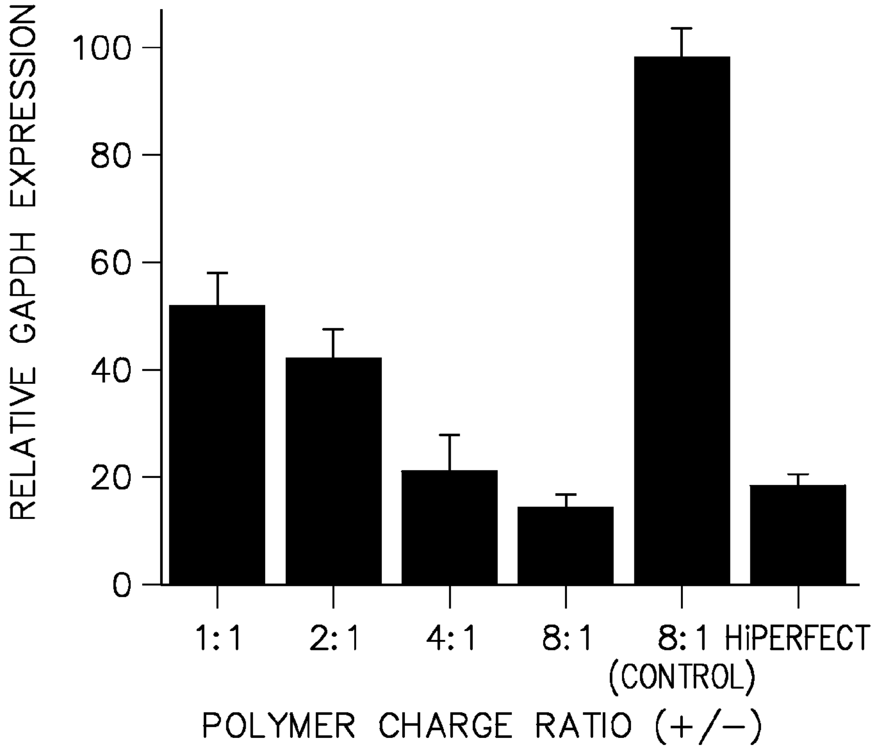
FIGS. 13A and 13B illustrate GAPDH knockdown in HeLas.
Figure 13B:
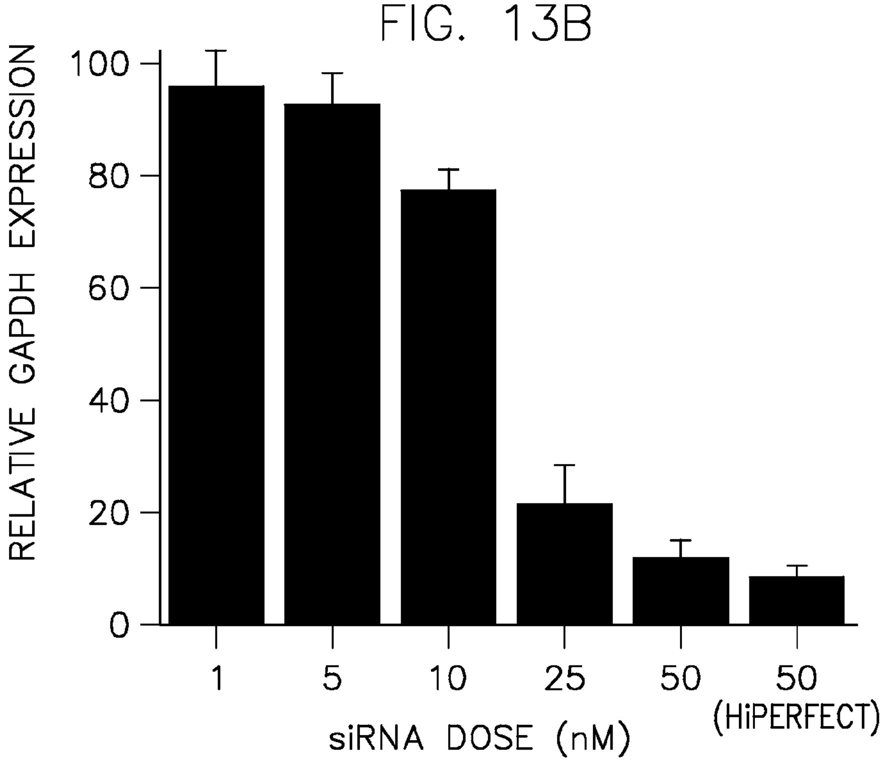

The efficacy of the series of polymers for siRNA delivery was screened using a GAPDH activity assay (Ambion). HeLas (12,000 cells/cm2) were plated in 96-well plates. After 24 h, complexes (charge ratios=4:1) were added to the cells at a final siRNA concentration of 25 nM in the presence of 10% serum. The extent of siRNA-mediated GAPDH protein reduction was assessed 48 h post-transfection. As a positive control, parallel knockdown experiments were run using HiPerFect (Qiagen) following manufacturer's conditions. The remaining GAPDH activity was measured as described by the manufacturer using the kinetic fluorescence increase method over 5 min and was calculated according to the following equation: % remaining expression=fluorescence, GAPDH/fluorescence, no treatment, where fluorescence=fluorescence-5 min−fluoresecence 1 min. The transfection procedure did not significantly affect GAPDH expression when a nontargeting sequence of siRNA was used. FIG. 13A shows GAPDH knockdown in HeLas measured via real time RT-PCR 48 h after treatment with complexes as a function of charge ratio (1:1-8:1) and FIG. 13B shows GAPDH knockdown in HeLas measured via real time RT-PCR 48 h after treatment with complexes as a function of siRNA dose (1-50 nM) with polymer 7 as the carrier. Negative control siRNA #1 (Ambion) and a commercially available transfection reagent, HiPerFect (Qiagen), were used as negative and positive controls, respectively.

After the initial screen to identify the carrier that produced the most robust siRNA-mediated GAPDH knockdown, real time reverse transcription polymerase chain reaction (RT-PCR) was used to directly evaluate siRNA delivery. After 48 hours of incubation with complexes as formed above, cells were rinsed with PBS. Total RNA was isolated using Qiagen's Qiashredder and RNeasy mini kit. Any residual genomic DNA in the samples was digested (RNase-Free DNase Set, Qiagen) and RNA was quantified using the RiboGreen assay (Molecular Probes) based on the manufacturer's instructions.

Reverse transcription was performed using the Omniscript RT kit (Qiagen). A 25 ng total RNA sample was used for cDNA synthesis and PCR was conducted using the ABI Sequence Detection System 7000 using predesigned primer and probe sets (Assays on Demand, Applied Biosystems) for GAPDH and beta-actin as the housekeeping gene. Reactions (20 μl total) consisted of 10 μL of 2× Taqman Universal PCR Mastermix, 1 μL of primer/probe, and 2 μL of cDNA, brought up to 20 μL with nuclease-free water (Ambion). The following PCR parameters were utilized: 95° C. for 90 s followed by 45 cycles of 95° C. for 30 s and 55° C. for 60 s. Threshold cycle (CT) analysis was used to quantify GAPDH, normalized to beta-actin and relative to expression of untreated HeLas.

Example 9

Functional Design of poly[HPMA]-b-[(PAA)(BMA)(DMAEMA)]

Figure 14:
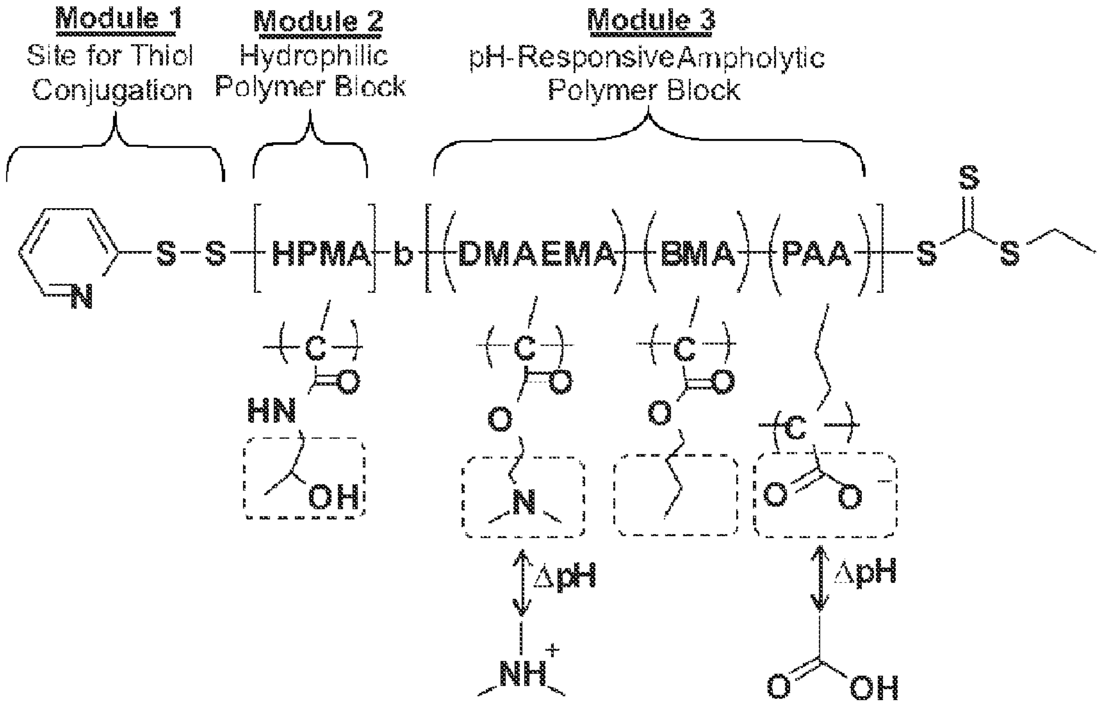
FIG. 14 illustrates the polymer design for Poly[HPMA]-b-[(PAA)(BMA)(DMAEMA)]

FIG. 14 shows the polymer design for Poly[HPMA]-b-[(PAA)(BMA)(DMAEMA)]. Multifunctional properties were incorporated via RAFT polymer synthesis strategies using a pyridyl disulfide end-functionalized CTA to form a diblock architecture designed to possess aqueous solubility and pH-dependent membrane destabilizing properties. The monomer chemical functionalities highlighted in FIG. 14 were chosen in order to produce the desired properties for each polymer block. Importantly, module 3 was designed to be near charge neutrality at physiologic pH (approximately 50% DMAEMA protonation and 50% PAA deprotonation predicted) and to undergo a transition to a more hydrophobic and positively charged state in lower pH environments.

Example 10

Synthesis of Pyridyl Disulfide-CTA

Figure 15:
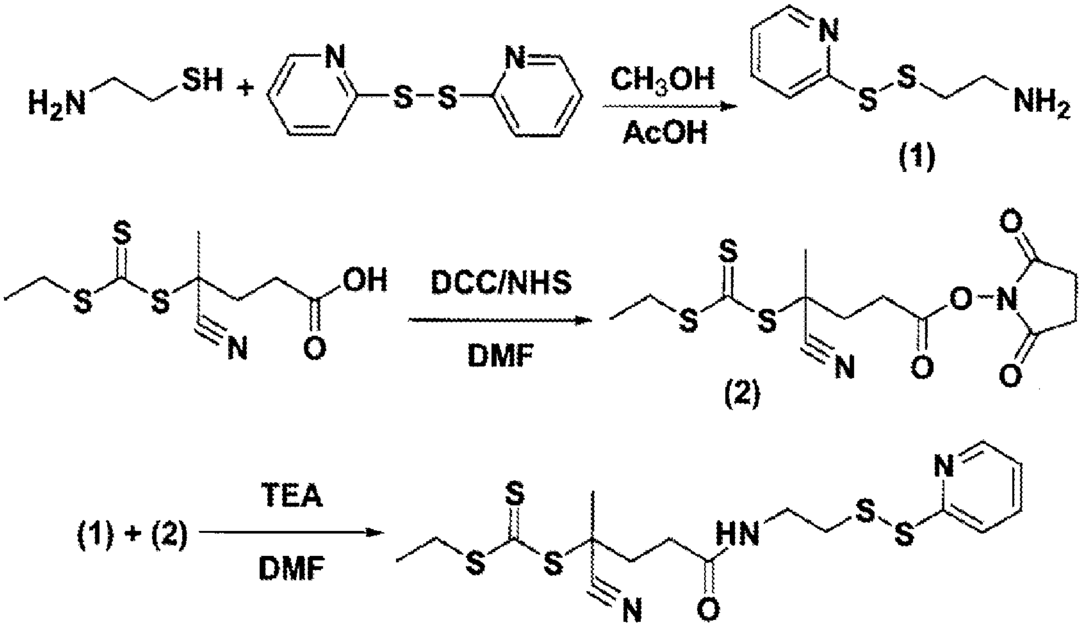
FIG. 15 illustrates the synthesis of pyridyl disulfide-CTA

The 4-cyano-4-(ethylsulfanylthiocarbonyl) sulfanylvpentanoic acid (ECT) precursor was synthesized as shown in FIG. 15. The pyridyl disulfide functionalized RAFT chain transfer agent (CTA) was synthesized by first converting ECT to the NHS ester followed by reaction with pyridyldithio-ethylamine. ECT (1.05 g, 4 mmol) and N-hydroxysuccinimide (0.460 g, 4 mmol) were dissolved in 100 mL of chloroform. The mixture was then cooled to 0° C. at which time N,N' dicyclohexylcarbodiimide (0.865 mg, 4.2 mmol) was added. The solution was maintained at 0° C. for 1 hour and then allowed to react at room temperature for 22 hours. The solution was then filtered to remove the dicyclohexyl urea and the solution concentrated via rotary evaporation. The resultant solid was then dried under vacuum and used without any further purification. NHS ECT (1.80 g, 5.0 mmol) and pyridyldithio-ethylamine (0.90 g, 5.0 mmol.) where then separately dissolved in 200 and 300 mL of chloroform, respectively. The solution of pyridyldithio-ethylamine was then added dropwise as three fractions 20 minutes apart. The mixture was then allowed to react at room temperature for 2 hours. After solvent removal, two successive column chromatographies (Silica gel 60, Merk) were performed (ethyl acetate:hexane 50:50; ethyl acetate: hexane 70:30 v/v) yielding a viscous orange solid. 1H NMR 200 MHz (CDCl3, RT, ppm) 1.29-1.41 [t, CH3CH2S: 3H], 1.85-1.93 [s, $(CH_3)C(CN)$: 3H], 2.33-2.59 [m, $C(CH_3)(CN)(CH_2CH_2)$: 4H], 2.86-2.97 [t, $CH_2SS$: 2H], 3.50-3.61 [t, $NHCH_2$: 2H], 7.11-7.22 [m, Ar Para CH: 1H], 7.46-7.52 [m, Ar CH Ortho: 1H], 7.53-7.62 [br, NH: 1H], 7.53-7.68 [m, Ar meta CH: 1H], 8.47-8.60 [m, meta CHN, 1H]. [00164] Preparation of Thiol Reactive Polymer: RAFT Polymerization of Pyridyl Disulfide Functionalized poly[HPMA]-b-[(PAA)(BMA)(DMAEMA)]. The RAFT polymerization of N-(2-hydroxypropyl)methacrylamide (HPMA) was conducted in methanol (50 weight percent monomer:solvent) at 70° C. under a nitrogen atmosphere for 8 hours using 2,2'-azo-bis-isobutyrylnitrile (AIBN) as the free radical initiator. The molar ratio of CTA to AIBN was 10 to 1 and the monomer to CTA ratio was set so that a molecular weight of 25,000 g/mol would be achieved if at 100% conversion. The poly(HPMA) macro-CTA was isolated by repeated precipitation into diethyl ether from methanol. [00165] The macro-CTA was dried under vacuum for 24 hours and then used for block copolymerization of dimethylaminoethyl methacrylate (DMAEMA), propylacrylic acid (PAA), and butyl methacrylate (BMA). Equimolar quantities of DMAEMA, PAA, and BMA ($[M]_o/[CTA]_o$=250) were added to the HPMA macroCTA dissolved in N,N-dimethylformamide (25 wt % monomer and macroCTA to solvent). The radical initiator V70 was added with a CTA to initiator ratio of 10 to 1. The polymerization was allowed to proceed under a nitrogen atmosphere for 18 hours at 30° C. Afterwards, the resultant diblock polymer was isolated by precipitation 4 times into 50:50 diethyl ether/pentane, redissolving in ethanol between precipitations. The product was then washed 1 time with diethyl ether and dried overnight in vacuo.

Gel permeation chromatography (GPC) was used to determine molecular weight and polydispersity (Mw/Mn, PDI) of both the poly(HPMA) macroCTA and the diblock copolymer in DMF. Molecular weight calculations were based on column elution times relative to polymethyl methacrylate standards using HPLC-grade DMF containing 0.1 wt % LiBr at 60° C. as the mobile phase. Tris(2-carboxyethyl) phosphine hydrochloride (TCEP) was used to reduce the polymer end pyridyl disulfide, releasing 2-pyridinethione. Based on the experimentally determined polymer molecular weight and the molar extinction coefficient of 2-pyridinethione at 343 nm (8080 $M^{-1}cm^{-1}$) in aqueous solvents, percent end group preservation was determined for the poly(HPMA) macroCTA and the diblock copolymer.

Example 11

Polymer-Peptide Conjugation

Fusion with the peptide transduction domain peptide transportin (also known as the Antennapedia peptide (Antp) sequence was utilized to synthesize a cell internalizing form of the Bak-BH3 peptide (Ant-BH3) containing a carboxyl-terminal cysteine residue (NH2-RQIKIWFQNRRMKWK-KMGQVGRQLAIIGDDINRRYDSC—COOH; SEQ ID NO:1). To ensure free thiols for conjugation, the peptide was reconstituted in water and treated for 1 hour with the disulfide reducing agent TCEP immobilized within an agarose gel. The reduced peptide (400 μM) was then reacted for 24 hours with the pyridyl disulfide end-functionalized polymer in phosphate buffer (pH 7) containing 5 mM ethylenediaminetetraacetic acid (EDTA).

Figure 16:
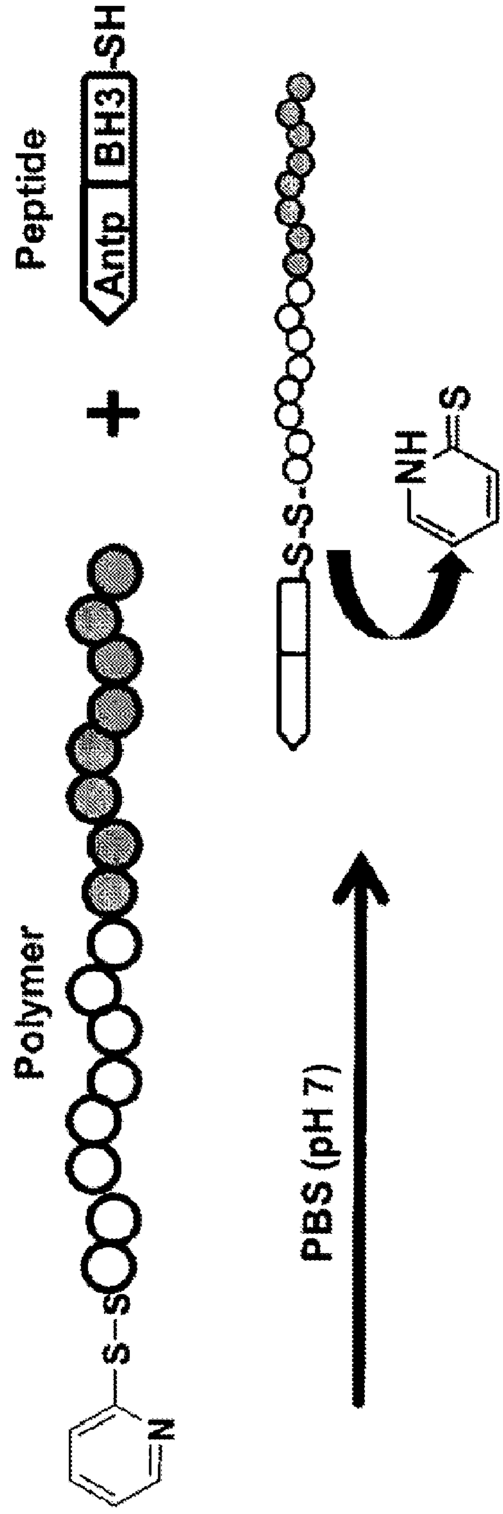
FIG. 16 illustrates reaction of pyridyl disulfide polymer end group with the peptide cysteine

As shown in FIG. 16, reaction of the pyridyl disulfide polymer end group with the peptide cysteine creates 2-pyridinethione, which can be spectrophotometrically measured to characterize conjugation efficiency. To further validate disulfide exchange, the conjugates were run on an SDS-PAGE 16.5% tricine gel. In parallel, aliquots of the conjugation reactions were treated with immobilized TCEP prior to SDS-PAGE to verify release of the peptide from the polymer in a reducing environment.

Figure 17A:
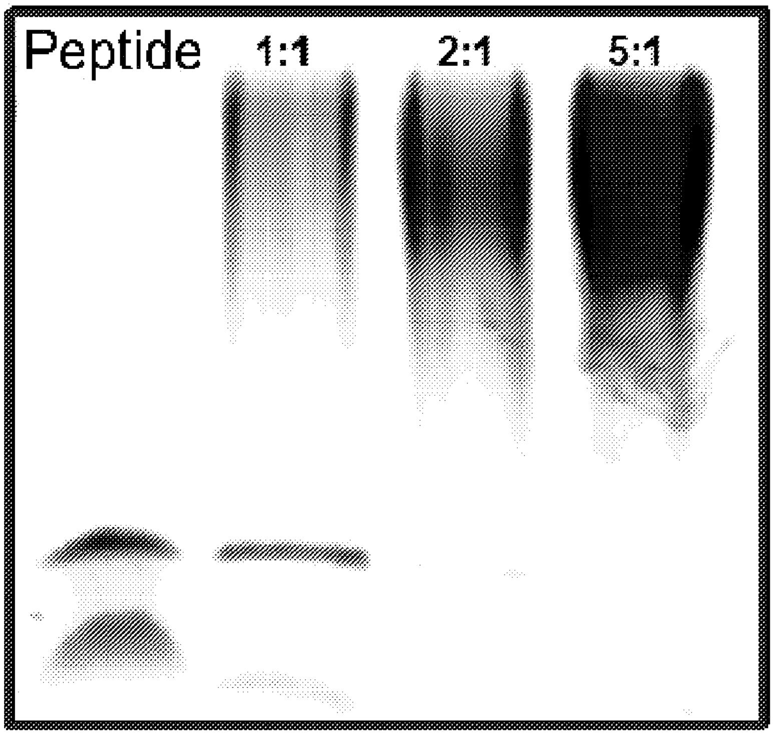
FIGS. 17A and 17B illustrate SDS PAGE gels for characterizing peptide-polymer conjugates.
Figure 17B:
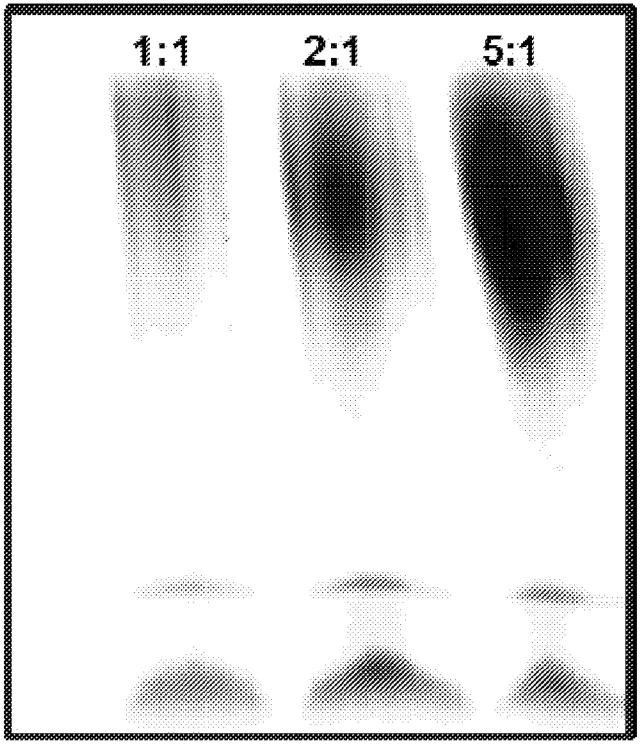

Conjugation reactions were conducted at polymer/peptide stoichiometries of 1, 2, and 5. UV spectrophotometric absorbance measurements at 343 nm for 2-pyridinethione release indicated conjugation efficiencies of 40%, 75%, and 80%, respectively (moles 2-pyridinethione/moles peptide). An SDS PAGE gel was utilized to further characterize peptide-polymer conjugates (FIG. 17). At a polymer/peptide molar ratio of 1, a detectable quantity of the peptide formed dimers via disulfide bridging through the terminal cysteine. However, the thiol reaction to the pyridyl disulfide was favored, and the free peptide band was no longer visible at polymer/peptide ratios equal to or greater than 2 (FIG. 17A). By treating the conjugates with the reducing agent TCEP, it was possible to cleave the polymer-peptide disulfide linkages as indicated by the appearance of the peptide band in these samples (FIG. 17B).

Example 12

PH-Dependent Membrane Destabilizing Properties of Poly[HPMA]-B-[(PAA)(BMA)(DMAEMA)]

Figure 18:
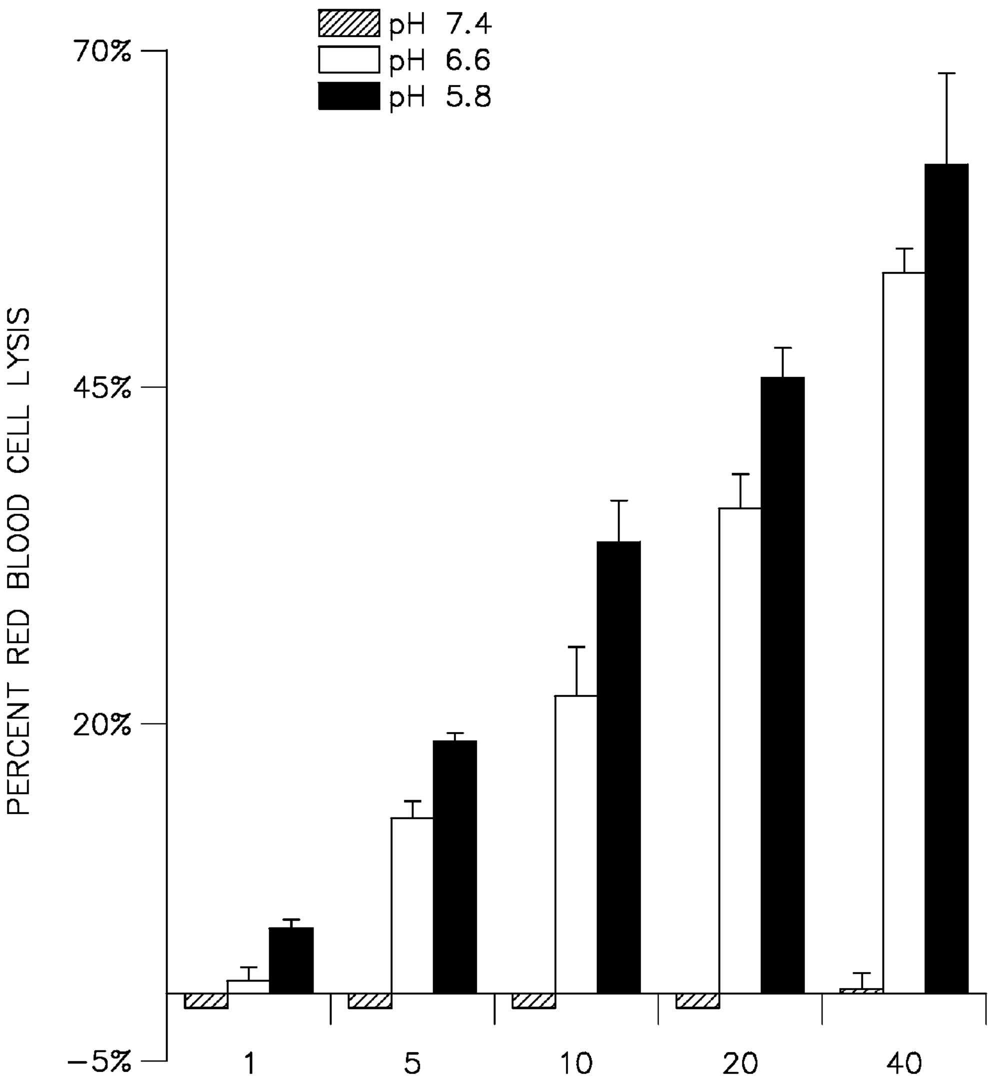
FIG. 18 illustrates a membrane disruption assay used to measure the capacity of the polymer to trigger pH-dependent disruption of lipid bilayer membranes

In order to assess the polymer's potential for endosomolytic activity, a membrane disruption assay was utilized to measure the capacity of the polymer to trigger pH-dependent disruption of lipid bilayer membranes as shown in FIG. 18. Whole human blood was drawn and centrifuged for plasma removal. The remaining erythrocytes were washed three times with 150 mM NaCl and resuspended into phosphate buffers corresponding to physiological (pH 7.4), early endosome (pH 6.6), and late endosome (pH 5.8) environments. The polymer (1-40 μg/mL) or 1% Triton X-100 was added to the erythrocyte suspensions and incubated for 1 hour at 37° C. Intact erythrocytes were pelleted via centrifugation, and the hemoglobin content within the supernatant was measured via absorbance at 541 nm. Percent hemolysis was determined relative to Triton X-100. Polymer hemolysis was quantified at concentrations ranging from 1-40 μg/mL relative to 1% v/v Triton X-100. This experiment was completed 2 times in triplicate, yielding similar results. The data shown represent a single experiment conducted in triplicate±standard deviation.

Red blood cell hemolysis measures pH-dependent membrane disruption properties of the diblock copolymer at pH values mimicking physiologic (7.4), early endosomal (6.6) and late endosomal (5.8) environments. At physiologic pH, no significant red blood cell membrane disruption was observed even at polymer concentrations as high as 40 μg/mL (FIG. 18). However, as the pH was lowered to endosomal values, a significant increase in hemolysis was detected, with greater membrane disruption at pH 5.8 compared to 6.6. The hemolytic behavior of the polymer correlated to polymer concentration, with nearly 70% erythrocyte lysis occurring at 40 μg/mL polymer in pH 5.8 buffer. This sharp "switch" to a membrane destabilizing conformation at endosomal pH combined with negligible membrane activity in the physiologic pH range indicates potential for this polymer as a non-toxic intracellular delivery vehicle.

Example 13

Characterization of Intracellular Delivery in HeLa Cells

HeLas, human cervical carcinoma cells (ATCC CCL-2), were maintained in minimum essential media (MEM) containing L-glutamine, 1% penicillin-streptomycin, and 10% FBS. Prior to experiments, HeLas were allowed to adhere overnight in 8-well chamber slides (20,000 cells/well) for microscopy or 96-well plates (10,000 cells/well) for other assays. Polymer-peptide conjugates and controls were added in MEM with 1% FBS.

Polymer intracellular delivery potential was evaluated following bioconjugation to the Bak-BH3 peptide fused with the Antp (penetratin) cell penetrating peptide. BH3 fusion to Antp has been extensively studied as a cell translocation domain and has previously been found to trigger apoptotic signaling (Li et al. Neoplasia (New York, N.Y. 2007; 9(10):801-811). However, it is believed that therapeutics delivered via peptidic transduction domains may suffer from hindered potency due to sequestration within intracellular vesicles (Sugita et al. British Journal of Pharmacology. 2008; 153(6):1143-1152). The following in vitro studies demonstrate that the combined Antp-BH3 peptide cytoplasmic delivery and pro-apoptotic functionality was enhanced by conjugation to the diblock polymer.

Microscopic Analysis of Conjugate Endosomal Escape. An amine reactive Alexa-488 succinimidyl ester was mixed at a 1 to 1 molar ratio with the Antp-BH3 peptide in anhydrous dimethyl formamide (DMF). Unreacted fluorophore and organic solvent were removed using a PD10 desalting column, and the fluorescently labeled peptide was lyophilized. Alexa-488 labeled Antp-BH3 was conjugated to the polymer as described above. Free peptide or polymer-peptide conjugate was applied to HeLas grown on chambered microscope slides at a concentration of 25 μM Antp-BH3. Cells were treated for 15 minutes, washed twice with PBS, and incubated in fresh media for an additional 30 minutes. The samples were washed again and fixed with 4% paraformaldehyde for 10 minutes at 37° C. Slides were mounted with ProLong Gold Antifade reagent containing DAPI and imaged using a fluorescent microscope.

Figure 19A:
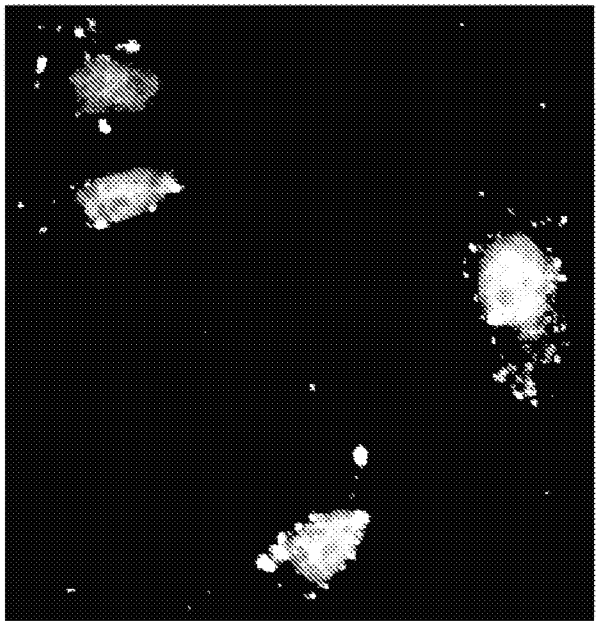
FIGS. 19A and 19B illustrate peptide intracellular localization following polymer conjugation.
Figure 19B:
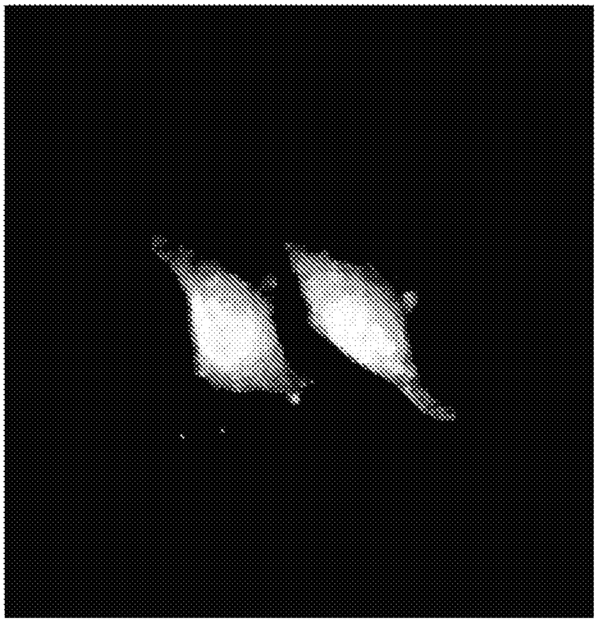

To study the effects of polymer conjugation on peptide endosomal escape, the Alexa-488 labeled peptide was analyzed by fluorescent microscopy. The fluorescently labeled peptide was delivered alone or as the polymer bioconjugate. Microscopic analysis revealed clear differences in peptide intracellular localization following polymer conjugation (FIG. 19). The peptide alone displayed punctate staining, indicative of endosomal compartmentalization. Samples delivered polymer-peptide conjugate exhibited a dispersed fluorescence pattern, consistent with peptide diffusion throughout the cytoplasm. Representative images illustrating (FIG. 19A) punctate peptide staining (green) in the samples delivered peptide alone and (FIG. 19B) dispersed peptide fluorescence within the cytosol following delivery of peptide-polymer conjugate. Samples were treated for 15 minutes with 25 μM peptide and prepared for microscopic examination following DAPI nuclear staining (blue).

Measurement of Conjugate Cytotoxicity. Bioconjugate efficacy for triggering tumor cell death was determined using a lactate dehydrogenase (LDH) cytotoxicity assay. At the end of each time point, cells were washed two times with PBS and then lysed with cell lysis buffer (100 μL/well, 20 mM Tris-HCl, pH 7.5, 150 mM NaCl, 1 mM Na2EDTA, 1 mM EGTA, 1% Triton, 2.5 mM sodium pyrophosphate, 1 mM β-glycerophosphate, 1 mM sodium orthovanadate) for 1 hour at 4° C. 20 μl of lysate from each sample was diluted into 80 μl PBS, and LDH was quantified by mixing with 100 μL of the LDH substrate solution. Following a 10 minute incubation, LDH was determined by measuring absorbance at 490 nm. Percent viability was expressed relative to samples receiving no treatment.

Figures 20A, 20B:
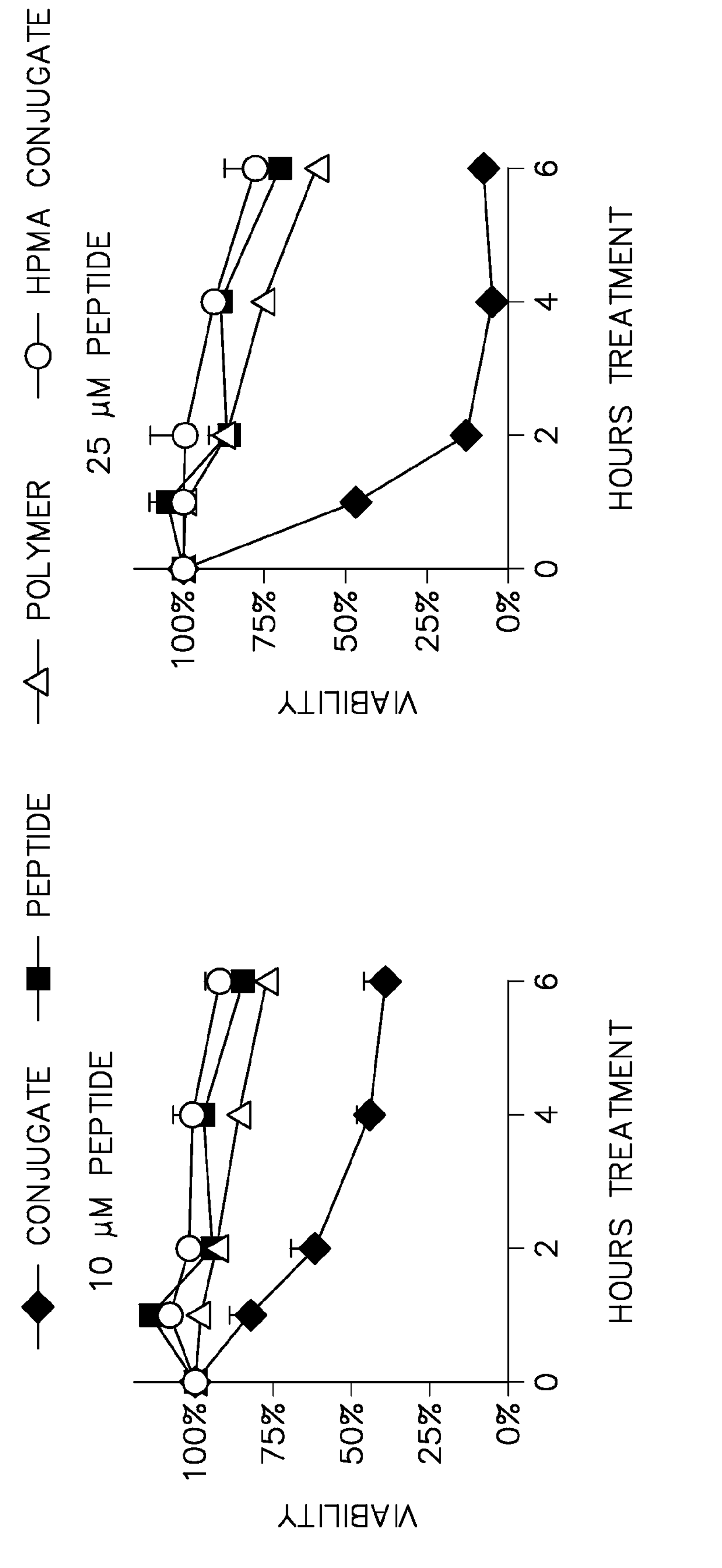
FIGS. 20A and 20B illustrate conjugates that lacked the pH-responsive block were similar to both control groups and did not result in significant toxicity.

To assess polymer-peptide conjugate bioactivity, a cytotoxicity study was conducted in HeLa cervical cancer cells. The Antp-BH3 polymer conjugate was found to potently trigger HeLa cell death in a dose dependent fashion. Less than 50% HeLa viability was detected after 6 hours of treatment with 10 μM peptide conjugate (FIG. 20A), and samples receiving 25 μM peptide conjugate (FIG. 20B) showed little if any viable cells following as little as 4 hours of exposure. Control samples receiving peptide or polymer alone displayed negligible treatment effect, and there was no difference between these control treatment groups. Importantly, Antp-BH3 poly(HPMA) conjugates that lacked the pH-responsive block were similar to both control groups and did not result in significant toxicity, further validating the functionality of the endosomolytic block (FIG. 20).

Figure 21B:
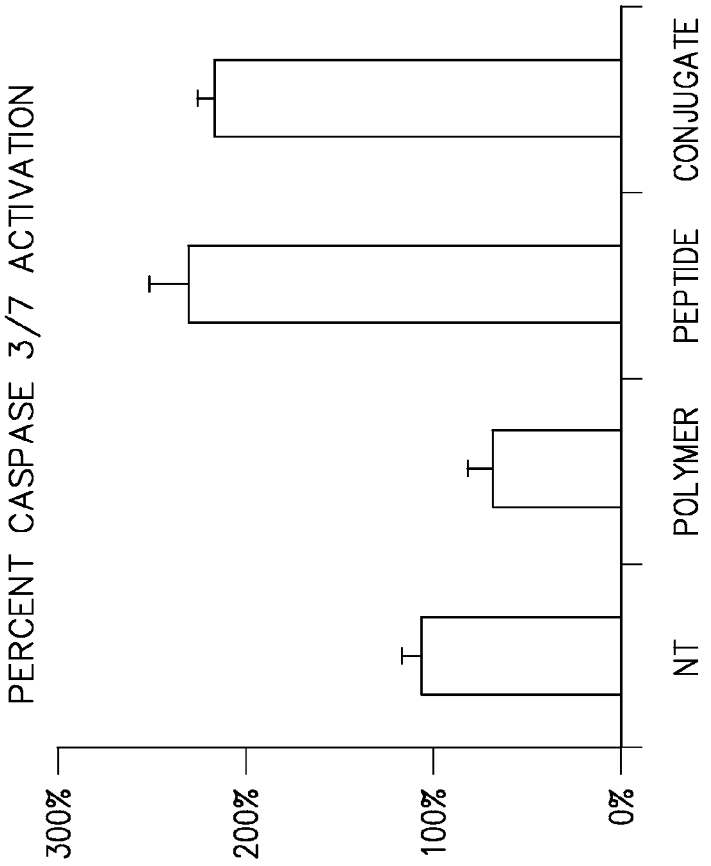
FIGS. 21A and 21B illustrate bioactivity of peptide conjugates.
Figure 21A:
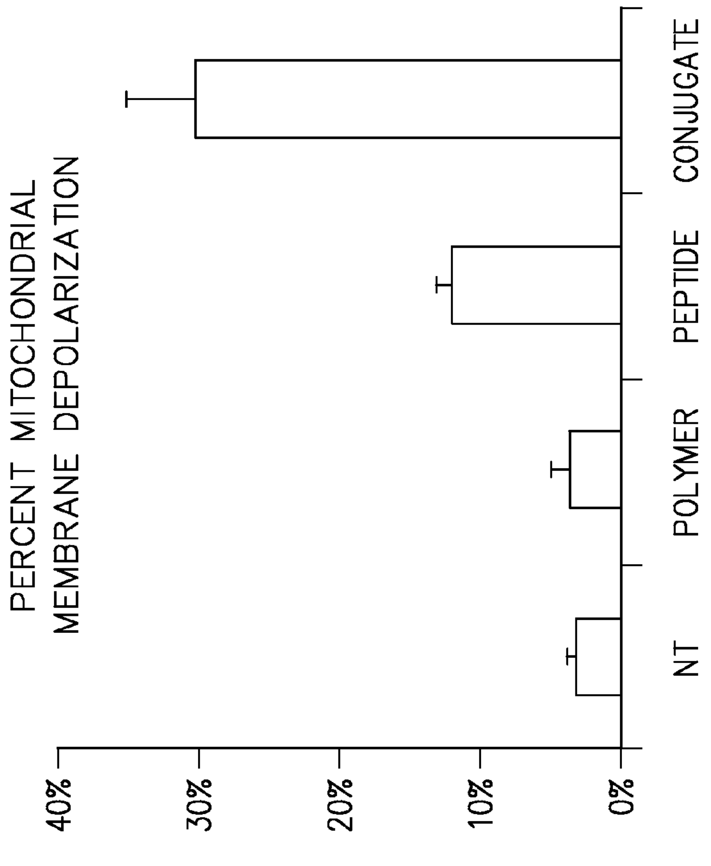

Flow Cytometry Evaluation of Mitochondrial Membrane Potential. Loss of mitochondrial membrane potential, a known indicator for apoptosis, was assessed using the JC-1 dye. JC-1 exhibits green fluorescence when dispersed in the cytosol, and in healthy cells, it forms red-fluorescent aggregates at the mitochondrial membrane (Cossarizza et al. Biochemical and biophysical research communications. 1993; 197(1):40-45). HeLas were incubated for 2 hours with 10 μM peptide or equivalent conjugate or polymer alone. JC-1 was added at a final concentration of 5 μg/mL and incubated for 15 minutes. Cells were washed 2 times with PBS, trypsinized, and resuspended in 0.5% BSA for flow cytometric analysis. Percent of cells displaying mitochondrial depolarization was quantified based on the number of green fluorescent cells that were negative for red fluorescence. Here, a significant loss of red fluorescent JC-1 aggregates and therefore a loss in mitochondrial polarization was detected following treatment with both the Antp-BH3 peptide and the polymer peptide conjugate (FIG. 21A). Polymer controls were similar to cells receiving no treatment while Antp-BH3 alone and in a polymer conjugate resulted in an approximately 4- and 10-fold increase, respectively, in percent of cells exhibiting loss of mitochondrial polarity.

Caspase 3/7 Activity Assay. Caspase 3/7 activation was measured using a commercially available assay kit. This assay utilizes a profluorescent caspase 3/7 substrate that once enzymatically cleaved becomes fluorescent allowing for determination of relative enzyme activity using a fluorescent plate reader. Here, HeLas were incubated for 30 minutes with 25 μM peptide (alone or as polymer conjugate) in addition to polymer alone in a quantity equivalent to the conjugate samples. Afterwards, a caspase 3/7 fluorogenic indicator was added directly to the culture media for each sample. Plates were shaken for 1 hour and then assayed using a fluorescent plate reader. Data were expressed as percent caspase activity relative to samples receiving no treatment.

Activation of caspases 3 and 7, which is indicative of pro-apoptotic signaling, can be measured using a profluorescent substrate specific to these proteases. FIG. 21B shows that controls containing the polymer alone displayed equivalent caspase activity relative to negative controls receiving no treatment. However, rapid caspase activation (approximately 2.5-fold) was detected following treatment with the Antp-BH3 peptide by itself or in the polymer conjugate form. The similar effects of Antp-BH3 alone or as a polymer conjugate could indicate that caspase signaling is saturated by treatment with the peptide alone or that other positive feedback mechanisms exist for amplification of perturbations in caspase activation state. Minimally, these results suggest that there was no steric hindrance or other reductions in peptide-induced caspase activity as a result of conjugation to the polymer.

What is claimed is:

1. A composition comprising:
(a) a copolymer comprising a diblock copolymer, the diblock copolymer having the chemical Formula I:

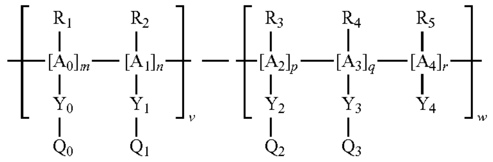

wherein
$A_0, A_1, A_2, A_3,$ and $A_4$ are independently selected from the group consisting of —C—, —C—C—, —C(O)(C)$_a$C(O)O—, —O(C)$_a$C(O)— and —O(C)$_b$O—; wherein,
a is 1-4;
b is 2-4;
$Y_4$ is selected from the group consisting of hydrogen, -(1C-10C)alkyl, -(3C-6C)cycloalkyl, —O(1C-10C)alkyl, —C(O)O(1C-10C)alkyl, —C(O)NR$_6$(1C-10C) and aryl, any of which is optionally substituted with one or more fluorine groups;
$Y_0, Y_1$ and $Y_2$ are independently selected from the group consisting of a covalent bond, —(1C-10C)alkyl-, —C(O)O(2C-10C) alkyl-, —OC(O)(1C-10C) alkyl-, —O(2C-10C)alkyl-, —S(2C-10C)alkyl-, and —C(O)NR$_6$(2C-10C) alkyl-;
$Y_3$ is selected from the group consisting of a covalent bond, -(1C-10C)alkyl- and -(6C-10C)aryl-; wherein tetravalent carbon atoms of $A_0$-$A_4$ that are not fully substituted with $R_1$-$R_5$ and $Y_0$-$Y_4$ are completed with an appropriate number of hydrogen atoms;
$R_1, R_2, R_3, R_4, R_5,$ and $R_6$ are independently selected from the group consisting of hydrogen, —CN, alkyl, alkynyl, heteroalkyl, cycloalkyl, heterocycloalkyl, aryl and heteroaryl, any of which is optionally substituted with one or more fluorine atoms;
$Q_0$ is a residue selected from the group consisting of residues which are hydrophilic at physiologic pH; conjugatable residues; functionalizable residues; and hydrogen;
$Q_1$ is a residue which is hydrophilic at normal physiological pH;
$Q_2$ is a residue which is positively charged at normal physiological pH;
$Q_3$ is a residue which is negatively charged at normal physiological pH, but undergoes protonation at lower pH;
m is a mole fraction of 0 to less than 1.0;
n is a mole fraction of greater than 0 to 1.0; wherein m+n=1;
p is a mole fraction of 0.1-0.9;
q is a mole fraction of 0.1 to 0.9;
r is present up to a mole fraction of 0.8; wherein p+q+r=1;
v is from 1 to 25 kDa; and
w is from 1 to 50 kDa; and
(b) a therapeutic agent.

2. The composition of claim 1, wherein $Q_1$ is a residue that is positively charged at normal physiological pH; negatively charged at normal physiological pH but undergoes protonation at lower pH; neutral at normal physiological pH; or zwitterionic at normal physiological pH.

3. The composition of claim 1, wherein the ratio of v:w is 1:1 to 1:3.

4. The composition of claim 1, wherein the therapeutic agent is associated with the copolymer.

5. The composition of claim 1, wherein the therapeutic agent siRNA.

6. The composition of claim 1, wherein the therapeutic agent is covalently attached to the copolymer.

7. The composition of claim 1, wherein the therapeutic agent is ionically associated with the copolymer.

8. A composition comprising:

(a) a copolymer comprising a diblock copolymer, the diblock copolymer having the chemical Formula I:

(I)

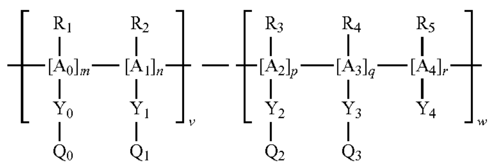

wherein $A_0$, $A_1$, $A_2$, $A_3$, and $A_4$ are independently selected from the group consisting of —C—C—, —C—, —C(O)$(C)_a$C(O)O—, —O$(C)_a$C(O)— and —O$(C)_b$O—; wherein, a is 1-4;

b is 2-4;

$Y_4$ is selected from the group consisting of hydrogen, -(1C-10C)alkyl, -(3C-6C)cycloalkyl, —O-(1C-10C) alkyl, —C(O)O(1C-10C)alkyl, —C(O)$NR_6$(1C-10C) and aryl, any of which is optionally substituted with one or more fluorine groups;

$Y_0$, $Y_1$, and $Y_2$ are independently selected from the group consisting of a covalent bond, -(1C-10C)alkyl-, —C(O)O(2C-10C) alkyl-, —OC(O)(1C-10C) alkyl-, —O(2C-10C)alkyl-, —S(2C-10C)alkyl-, and —C(O)$NR_6$(2C-10C) alkyl-;

$Y_3$ is selected from the group consisting of a covalent bond, -(1C-10C)alkyl and -(6C-10C)aryl; wherein tetravalent carbon atoms of $A_0$-$A_4$ that are not fully substituted with $R_1$-$R_5$ and $Y_0$-$Y_4$ are completed with an appropriate number of hydrogen atoms;

$R_1$, $R_2$, $R_3$, $R_4$, $R_5$, and $R_6$ are independently selected from the group consisting of hydrogen, —CN, alkynyl, heteroalkyl, cycloalkyl, heterocycloalkyl, aryl, and heteroaryl, any of which is optionally substituted with one or more fluorine atoms;

$Q_0$ is a residue selected from the group consisting of amino, alkylamino, ammonium, alkylammonium, guanidine, imidazolyl, pyridyl, carboxyl, sulfonamide, boronate, phosphonate, phosphate, hydroxy, polyoxylated alkyl, polyethylene glycol, polypropylene glycol, thiol, azide, alkyne, succinimide ester, tetrafluorophenyl ester pentafluorophenyl ester, p-nitrophenyl ester, pyridyl disulfide, and hydrogen;

$Q_1$ is a residue selected from the group consisting of amino, alkylamino, ammonium, alkylammonium, guanidine, imidazolyl, pyridyl, carboxyl, sulfonamide, boronate, phosphonate, phosphate, hydroxy, polyoxylated alkyl, polyethylene glycol, polypropylene glycol, and thiol;

$Q_2$ is a residue selected from the group consisting of amino, alkylamino, ammonium, alkylammonium, guanidine, imidazolyl, and pyridyl;

$Q_3$ is a residue selected from the group consisting of carboxyl, sulfonamide, boronate, phosphonate, and phosphate;

m is a mole fraction of 0 to less than 1.0;

n is a mole fraction of greater than 0 to 1.0, wherein m+n=1;

p is a mole fraction of 0.1 to 0.9;

q is a mole fraction of 0.1 to 0.9;

r is present up to a mole fraction of 0.8, wherein p+q+r=1;

v is from 1 to 25 kDa; and w is from 1 to 50 kDa; and (b) a therapeutic agent.

9. The composition of claim 8, wherein $Q_1$ is a polyethylene glycol residue.

10. The composition of claim 8, wherein $Q_2$ is an amino residue.

11. The composition of claim 8, wherein $Q_3$ is a carboxyl residue.

12. The composition of claim 8, wherein m is 0 and $Q_1$ is a polyethyleneglycol residue.

13. The composition of claim 8, wherein m is 0, $Q_1$ is a polyethylene glycol residue, $Q_2$ is an amino residue, and $Q_3$ is a carboxyl residue.

14. The composition of claim 8, wherein $A_1$ is —C—C—;

$Y_1$ is —C(O)$OCH_2CH_2$—; and $R_2$ is —$CH_3$.

15. The composition of claim 8, wherein $A_2$ is —C—C—;

$Y_2$ is —C(O)$OCH_2$—; and $R_3$ is —$CH_3$.

16. The composition of claim 8, wherein $A_3$ is —C—C—;

$R_4$ is $CH_3CH_2CH_2$—; and $Y_3$ is a covalent bond.

17. The composition of claim 8, wherein $A_4$ is —C—C—;

$R_5$ is selected from the group consisting of hydrogen and —$CH_3$; and, $Y_3$ is —C(O)$O(CH_2)_3CH_3$.

18. The composition of claim 8, wherein $A_0$ is —C—C—;

$R_1$ is selected from the group consisting of hydrogen and (1C-3C)alkyl; and $Y_0$ is selected from the group consisting of —C(O)O(2C-10C)alkyl-.

19. The composition of claim 8, wherein v is from 5 to 25 kDa.

20. The composition of claim 8, wherein m is 0.

21. The composition of claim 8, wherein $A_0$, $A_1$, $A_2$, $A_3$, and $A_4$ are —C—C—;

$Y_4$ is —C(O)O(1C-10C)alkyl:

$Y_0$, $Y_1$, and $Y_2$ are —C(O)O(2C-10C) alkyl-;

$Y_3$ is a covalent bond; wherein tetravalent carbon atoms of $A_0$-$A_4$ that are not fully substituted with $R_1$-$R_5$ and $Y_0$-$Y_4$ are completed with an appropriate number of hydrogen atoms;

$R_1$, $R_2$, $R_3$, $R_4$, and $R_5$ are independently selected from the group consisting of hydrogen and alkyl;

$Q_0$ is a pyridyl disulfide residue;

$Q_1$ is a residue selected from the group consisting of polyoxylated alkyl, polyethylene and polypropylene glycol;

$Q_2$ is a residue selected from the group consisting of amino and alkylamino;

$Q_3$ is a car bond residue;

m is a mole fraction of 0 to less than 1.0;

n is a mole fraction of greater than 0 to 1.0, wherein m+n=1;

p is a mole fraction of 0.1 to 0.9;

q is a mole fraction of 0.1 to 0.9;

r is present up to a mole fraction of 0.8, wherein p+q+r=1;

v is from 1 to 25 kDa; and w is from 1 to 50 kDa.

22. The composition of claim 8, wherein m is 0 and $Q_1$ is a polyethylene glycol residue.

23. The composition of claim 8, wherein m is 0, $Q_1$ is a polyethylene glycol residue, and $Q_2$ is an amino residue.

24. The composition of claim 8, wherein the diblock copolymer, having the chemical Formula I, is a diblock copolymer of the Formula IV2:

IV2

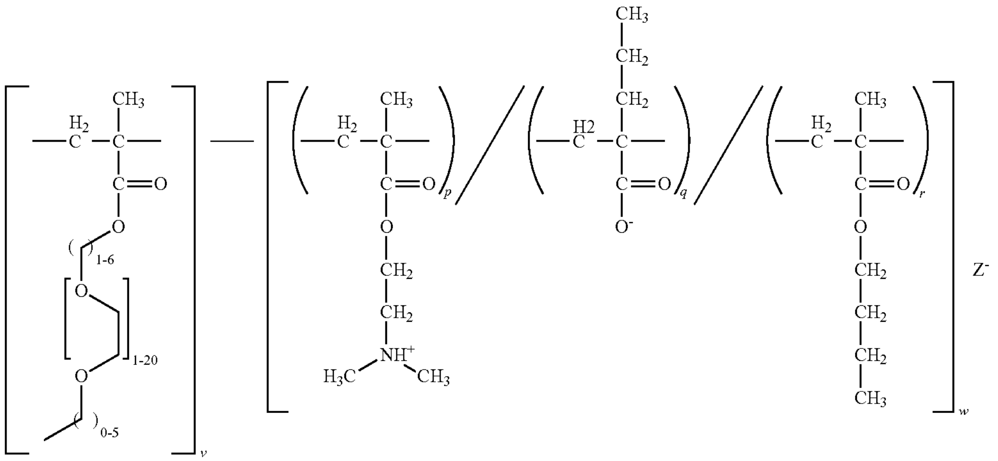

wherein p is a mole traction of 0.1 to 0.9;

q is a mole fraction of 0.1 to 0.9;

r is present up to a mole fraction of 0.8, wherein p+q+r=1;

v is from 1 to 25 kDa;

w is from 1 to 50 kDa; and $Z^-$ is a physiological acceptable counterion.

25. The composition of claim 24, wherein $Z^-$ is selected from the group consisting of hydroxide, chloride, phosphate, sulfate, sulfonate, acetate, propionate, butyrate, valerate, caproate, caprylate, caprate, laurate, myristate, palmate, stearate, palmitolate, oleate, linolate, arachidate, gadoleate, vaccinate, lactate, glycolate, salicylate, desaminophenylalanine, desaminoserine, desaminothreonine, ε-hydroxycaproate, 3-hydroxybutylrate, 4-hydroxybutyrate, and 3-hydroxyvalerate.

26. The composition of claim 24, wherein $Z^-$ is hydroxide.

27. The composition of claim 8, wherein the therapeutic agent is a polynucleotide, peptide, polypeptide, or other therapeutically effective biomolecule.

28. The composition of claim 8, wherein the therapeutic agent is a messenger RNA (mRNA), siRNA, microRNA (miRNA), short hairpin RNA (shRNA), asymmetrical interfering RNA (aiRNA), or dicer substrate.

29. The composition of claim 8, wherein the therapeutic agent is an siRNA.

30. The composition of claim 8, wherein the therapeutic agent is a polypeptide.

31. The composition of claim 8, wherein the therapeutic agent is covalently attached to the copolymer.

32. The composition of claim 8, wherein the composition comprises a plurality of the copolymers.

* * * * *

UNITED STATES PATENT AND TRADEMARK OFFICE

CERTIFICATE OF CORRECTION

PATENT NO. : 9,476,063 B2
APPLICATION NO. : 12/992517
DATED : October 25, 2016
INVENTOR(S) : Stayton et al.

It is certified that error appears in the above-identified patent and that said Letters Patent is hereby corrected as shown below:

In the Claims

| Column | Line | Error |
| --- | --- | --- |
| 49 (Claim 1) | 62 | "-O(1C-10C)alkyl," should be -- -O-(1C-10C)alkyl,-- |
| 50 (Claim 1) | 49 | "0.1-0.9" should read --0.1 to 0.9-- |
| 50 (Claim 5) | 65 | "agent siRNA" should read --agent is an siRNA-- |
| 51 (Claim 8) | 37 | "-CN, alkynyl," should read -- -CN, alkyl, alkynyl-- |
| 51 (Claim 8) | 45-46 | "tetrafluorophenyl ester" should read --tetrafluorophenyl ester,-- |
| 52 (Claim 12) | 8 | "polyethyleneglycol" should read --polyethylene glycol-- |
| 52 (Claim 17) | 28 | "$Y_3$" should read --$Y_4$-- |
| 52 (Claim 21) | 50 | "polyethylene" should read --polyethylene glycol,-- |
| 52 (Claim 21) | 54 | "car bond" should read --carboxyl-- |

Signed and Sealed this
Ninth Day of July, 2019

Andrei Iancu
*Director of the United States Patent and Trademark Office*

53 4 should read
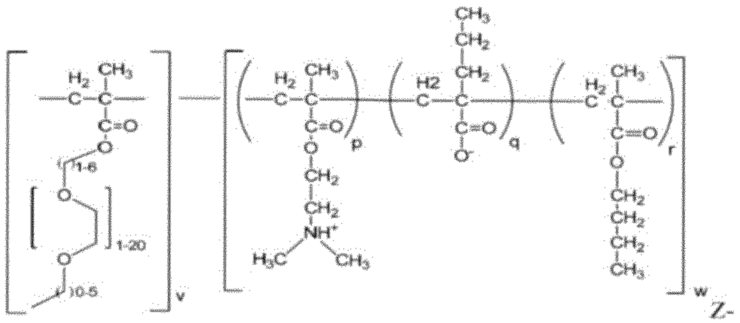
(Claim 24) -- --

SEQUENCE LISTING

<160> NUMBER OF SEQ ID NOS: 1

<210> SEQ ID NO 1
<211> LENGTH: 38
<212> TYPE: PRT
<213> ORGANISM: Artificial Sequence
<220> FEATURE:
<223> OTHER INFORMATION: Synthetic

<400> SEQUENCE: 1

Arg Gln Ile Lys Ile Trp Phe Gln Asn Arg Arg Met Lys Trp Lys Lys
1               5                   10                  15

Met Gly Gln Val Gly Arg Gln Leu Ala Ile Ile Gly Asp Asp Ile Asn
            20                  25                  30

Arg Arg Tyr Asp Ser Cys
        35